(12) United States Patent
Bommarius et al.

(10) Patent No.: US 8,835,136 B2
(45) Date of Patent: Sep. 16, 2014

(54) ENGINEERED AMINE DEHYDROGENASES AND METHODS OF USE THEREOF

(71) Applicant: Georgia Tech Research Corporation, Atlanta, GA (US)

(72) Inventors: Andreas Sebastain Bommarius, Atlanta, GA (US); Michael Justin Abrahamson, Atlanta, GA (US); Bettina Bommarius, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/895,173

(22) Filed: May 15, 2013

(65) Prior Publication Data
US 2013/0309734 A1 Nov. 21, 2013

Related U.S. Application Data

(60) Provisional application No. 61/647,098, filed on May 15, 2012, provisional application No. 61/682,369, filed on Aug. 13, 2012, provisional application No. 61/808,251, filed on Apr. 4, 2013.

(51) Int. Cl.
*C12N 9/06* (2006.01)
*C12N 9/96* (2006.01)
*G01N 33/535* (2006.01)

(52) U.S. Cl.
CPC ....... *C12N 9/0014* (2013.01); *C12Y 104/99003* (2013.01)
USPC ............................ 435/128; 435/188; 435/189

(58) Field of Classification Search
None
See application file for complete search history.

(56) References Cited

PUBLICATIONS

Yamada et al. "Nucleotide sequencing of phenylalanine dehydrogenase gene from *Bacillus badius* IAM 11059" Biosci. Biotech. Biochem. 1995 59, 1994-1995.*

* cited by examiner

*Primary Examiner* — Suzanne M Noakes
*Assistant Examiner* — Gerard Lacourciere
(74) *Attorney, Agent, or Firm* — Pabst Patent Group LLP

(57) ABSTRACT

Non-naturally occurring amine dehydrogenases (AmDH) and methods of use thereof the produce chiral amines are disclosed. The AmDH are variants of amino acid dehydrogenases. AmDH based on phenylalanine, leucine, and valine scaffolds are provided. The AmDH typically have one, two, three, four, or more amino acid alterations relative to the scaffold. The alterations to the scaffold result in an enzyme that accepts the analogous ketone, such as methyl isobutyl ketone (MIBK), instead of the wild-type α-keto acid. Chimeric AmDH are also disclosed. The chimeras are fusion proteins that include a substrate binding domain from a first AmDH and a cofactor binding domain from a second AmDH. In a preferred embodiment, one of the domains is from a PheDH-based AmDH and one of the domains is from a LeuDH-based AmDH.

12 Claims, 12 Drawing Sheets

ENGINEERED AMINE DEHYDROGENASES AND METHODS OF USE THEREOF

CROSS-REFERENCE TO RELATED APPLICATIONS

This application claims benefit of U.S. Provisional Application No. 61/647,098, filed May 15, 2012, U.S. Provisional Application No. 61/682,369 filed Aug. 13, 2012, and U.S. Provisional Application No. 61/808,251, filed Apr. 4, 2013, each of which are herein incorporated by reference in its entirety.

REFERENCE TO THE SEQUENCE LISTING

The Sequence Listing submitted May 15, 2013 as a text file named "GTRC_6062_ST25.txt," created on May 15, 2013 and have a size of 85,074 bytes is hereby incorporated by reference.

FIELD OF THE INVENTION

The invention is generally related to compositions and methods of making chiral amines.

BACKGROUND OF THE INVENTION

Enzymes are unique in their ability to significantly enhance reaction rates under mild conditions with high levels of efficiency and selectivity. After substrates have bound to an enzyme's active site, their half-life is usually only a fraction of a second (Wolfenden, et al., *Accounts of Chemical Research,* 34, (12): 938-945 (2001)). Some enzymes perform catalysis so well they border on the physical limitations of efficiency with encountering substrate in solution, and have been known to achieve rate enhancements ($k_{cat}/k_{uncat}$) in excess of 19 orders of magnitude. These outstanding examples of enzymatic catalysis establish their remarkable power, and demonstrate their potential use in chemical synthesis.

In addition to rate enhancement, many enzymes are selective in their catalysis and allow for the direct production of single enantiomers. Single enantiomers of target product molecules have a large importance in the pharmaceutical and agricultural industries. Therapeutic compounds often act as structurally optimized inhibitors of biological processes. Since the human body functions using chiral chemistry, these compounds almost always contain chiral centers. In 2006, 80% of small-molecule drugs approved by FDA were chiral and 75% were single enantiomers (Thayer, *Chemical and Engineering News,* 85, (32): 11-19 (2007). USA Food and Drug Administration (FDA) regulations require proof that any non-therapeutic isomer comprising over 1% of the total composition be non-teratogenic. Thus, a racemic drug would require separate toxicology studies of each enantiomer. Further, as the complexity of these compounds increases, molecules often require more than one chiral center (Pollard, et al., *Trends in Biotechnology,* 25, (2): 66-73 (2007)). It is common for pharmaceutical processes to require a minimum acceptable enantiomeric excess (e.e.) of 98% to circumvent these difficulties.

Chiral intermediates are classically prepared by three different routes Carey, et al., *Organic & Biomolecular Chemistry,* 4, (12): 2337-2347 (2006)). One method is to simply attain them through a naturally occurring chiral synthon. This allows for an inexpensive and readily available source of natural products, but this pool of compounds is limited. Alternatively, chirality can be achieved through the resolution of a racemic mixture, as seen in the kinetic resolution of alcohols and amines through the application of lipases or esterases (Heine, et al., *Protein Engineering Design and Selection,* 20, (3): 125-131 (2007); Reetz, et al., *CHIMIA International Journal for Chemistry,* 50, (12): 668-669 (1996); Schmidt, *Chembiochem,* 7, (5): 805-809 (2006)). The major disadvantage of kinetic resolution is an unfavorable equilibrium constant, usually near unity. The use of a second reaction is required to drive the reaction to completion. Lastly, the chiral centers can be synthesized directly using an asymmetric catalyst or enzyme. If the desired selectivity is not achieved initially, multiple enrichments, such as crystallization, can be required to achieve an increased selectivity. In comparison to other catalysts, enzymes usually offer superior enantio- and regioselectivity, commonly reporting enantiomeric excesses "e.e.'s" of >99.9% (Bommarius, et al., Wiley-VCH Verlag GmbH & Co., (2004). High initial selectivity eliminates the need for enrichment, significantly reducing the cost of production.

One of the short comings of biocatalysis is the limited number of reactions which have identified enzymatic routes. In 2005, the American Chemical Society's (ACS) Green Chemistry Institute (GCI) and several leading global pharmaceutical companies created the ACS GCI Pharmaceutical Roundtable. The goals of this center encompassed innovation in the discovery, development, and production of pharmaceuticals. Consequently, the Roundtable identified the most aspirational reactions currently challenging the pharmaceutical industry (Constable, et al., *Green Chemistry,* 9, (5): 411-420 (2007). The reductive amination of a prochiral ketone with free ammonia to produce chiral amines ranked second on this list, and had yet to be achieved.

Therefore, it is an object of the invention to provide compositions and methods for reductive amination of a prochiral ketone to produce chiral amines.

It is another object to provide recombinant enzymes for the production of chiral compounds.

SUMMARY OF THE INVENTION

Recombinant amine dehydrogenases (AmDHs) and methods of use thereof are disclosed. The AmDHs are genetically engineered amino acid dehydrogenases. AmDHs based on phenylalanine, leucine, and valine scaffolds are provided. The AmDHs typically have one, two, three, four, or more amino acid alterations relative to the amino dehydrogenase scaffold. The alterations to the amino dehydrogenase scaffold produce an enzyme that accepts the analogous ketone, such as methyl isobutyl ketone (MIBK) instead of the wild-type α-keto acid.

Chimeric AmDHs are also disclosed. The chimeras are fusion proteins that include a substrate binding domain from a first AmDH and a cofactor binding domain from a second AmDH. In a preferred embodiment, one of the domains is from an amine dehydrogenase based on a phenylalanine dehydrogenase scaffold (PheDH-AmDH) and one of the domains is from a occurring amine dehydrogenase based on a leucine dehydrogenase scaffold (LeuDH-AmDH).

Methods of making chiral amines using the AmDHs are also disclosed. The methods typically including reacting a substrate with an effective amount the amine dehydrogenase in a reaction mixture including a cofactor such as NADH to produce a chiral amine. In some embodiments, the reaction mixture includes glucose and glucose dehydrogenase (GDH) or formate and formate dehydrogenase (FDH) to recycle the cofactor. In some embodiments, the reaction mixture includes an organic solvent such as acetone. The reaction can be carried out by whole cell catalysis or in an enzyme membrane reactor. In some embodiments, the amine dehydrogenase is a LeuDH-based amine dehydrogenase or a chimera thereof and the substrate is selected from the group consisting of methyl benzyl amine (MBA), cyclohexylamine, cylcohexanone, ethyl pyruvate, methyl aceto acetate, ethyl-3-oxohexanoate, and acetophenone. In some embodiments, the amine dehydrogenase is a PheDH-based amine dehydrogenase or a chimera thereof and the substrate is methylketone such as para-fluoro phenyl acetone (PFPA), phenoxy-2-propanone, 2-hexanone, methyl isobutyl ketone and 3-methyl-2-butanone.

BRIEF DESCRIPTION OF THE DRAWINGS

FIG. 24A shows a chromatogram of adamantylethylamine product formed with C1-AmDH overlaid over a chromatogram for a racemic standard of adamantylethylamine. FIG. 24B shows a chromatogram for methylbenzylamine product formed with C1-AmDH overlaid over a chromatogram for a racemic standard of methylbenzylamine.

DETAILED DESCRIPTION OF THE INVENTION

I. Definitions

Figure 1:
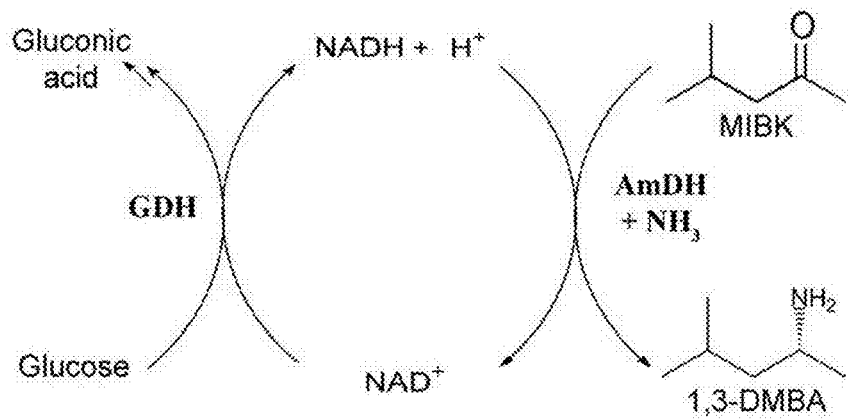
FIG. 1 is an asymmetric synthesis reaction scheme showing an amine dehydrogenase paired with a glucose dehydrogenase cofactor recycling system.

As used herein, a "LeuDH-AmDH" is a non-naturally occurring amine dehydrogenase based on a leucine dehydrogenase scaffold.

As used herein, a "PheDH-AmDH" is a non-naturally occurring amine dehydrogenase based on a phenylalanine dehydrogenase scaffold.

As used herein, a "ValDH-AmDH" is a non-naturally occurring amine dehydrogenase based on a valine dehydrogenase scaffold.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, a "variant" polypeptide contains at least one amino acid sequence alterations as compared to the amino acid sequence of the corresponding wild-type or reference polypeptide. An amino acid sequence alteration can be, for example, a substitution, a deletion, or an insertion of one or more amino acids, or combinations thereof.

A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides disclosed and still obtain a molecule desired characteristics (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein the term "isolated" is meant to describe a compound of interest (e.g., nucleic acids, polypeptides, etc.) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids or polypeptides are at least 60% free, preferably 75% free, and most preferably 90% free from other associated components.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man.

As used herein, "chiral" refers to a molecule that has a non-superposable mirror image. The feature that is most often the cause of chirality in molecules is the presence of an asymmetric carbon atom.

As used herein, "enantiomer" refers to one of two stereoisomers that are mirror images of each other that are non-superposable (not identical).

As used herein, "enantiomeric excess" or "e.e." refers to the absolute difference between the mole fraction of each enantiomer.

II. Recombinant Amine Dehydrogenases

Biocatalysts are increasingly prevalent in the large-scale synthesis of enantiomerically pure compounds (EPCs), which are mainly used as active pharmaceutical ingredients (APIs). Enantiomerically pure forms can lead to lower dosages and improved efficacy. However, many sought-after reactions lack a suitable enzymatic production route.

Although chiral amines can be produced both chemically and enzymatically, the large-scale production of chiral amines is still challenging and heavily reliant on traditional methods of chemical synthesis. Common methods include resolution though fractional crystallization and the hydrogenation of C=N bonds, particularly in enamines. Nonetheless, some chemoenzymatic routes, particularly with transaminases (Koszelewski, et al., *Trends in Biotechnology*, 28, (6): 324-332 (2010); Stewart, *Current Opinion in Chemical Biology*, 5, (2): 120-129 (2001); Taylor, et al., *Trends in Biotechnology*, 16, (10): 412-418 (1998); Truppo, et al., *Chem Comm*, 2009: 2127-2129 (2009); Tufvesson, et al., *Biotechnology and Bioengineering*, 108, (7): 1479-1493 (2011)), have shown promise in the dynamic kinetic resolution of racemic amines (Truppo, et al., *Chem Comm*, 2009: 2127-2129 (2009); Koszelewski, *Advanced Synthesis & Catalysis*, 350, (17): 2761-2766. (2008); Pellissier, 2011, *Tetrahedron*, 67, (21): 3769-3802 (2011)) and the direct asymmetric synthesis of amines with ω-transaminases (ω-TA), as used in the synthesis of sitagliptin (Koszelewski, et al., *Angewandte Chemie International Edition*, 47, (48): 9337-9340 (2008); Shin., et al., *Biotechnology and Bioengineering*, 65, (2): 206-211 (1999); Truppo, et al., *Organic Process Research & Development*, 14, (1): 234-237 (2009). This process eliminated the use and removal of a less-selective rhodium catalyst, yet requires the use of a sacrificial amine source. The undesired ketone by-product must also be removed to shift the reaction equilibrium beyond about 50% conversion.

Figure 2:
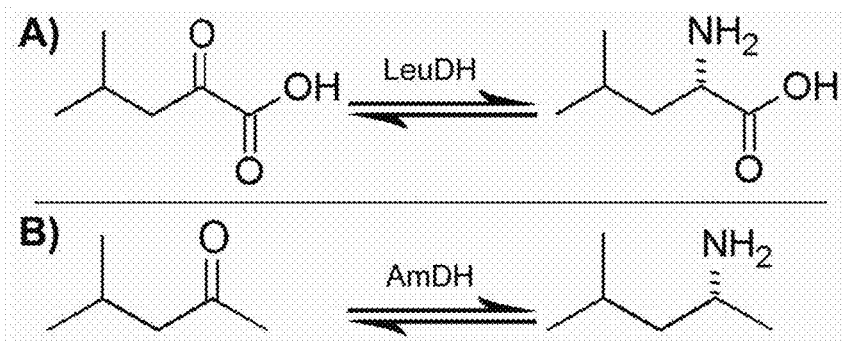
FIGS. 2A-2B are schemes showing the enzymatic reactions driven by wild type LeuDH (2A) and engineered LeuDH-AmDH (2B).

Non-naturally occurring amine dehydrogenases (AmDHs) also referred to as recombinant AmDH, and methods of use thereof are disclosed. The AmDHs are variants of amino acid dehydrogenases, or chimeric fusion proteins thereof. Instead of the wild-type α-keto acid, the amine dehydrogenases accept the analogous ketone, methyl isobutyl ketone (MIBK), which corresponds to replacement of the carboxyl moiety with a methyl group (FIG. 2). The amino dehydrogenases can be used without a rhodium catalyst and do not require the removal of ketone by-product. When paired with a cofactor recycling system, such as glucose/glucose dehydrogenase (GDH) or formate/formate dehydrogenase (FDH), the recombinant amine dehydrogenases allow for the direct production of chiral amines, with the consumption of only an inexpensive reducing agent, such as glucose or formate, and free ammonia (FIG. 1).

As discussed in more detail below, the disclosed recombinant amine dehydrogenases are based on an amino acid dehydrogenase scaffold. Therefore, the amine dehydrogenases are variants of the amino acid dehydrogenase scaffold. The variant typically has one or more alterations in amino acid sequence compared to the reference sequence. The amino acid alterations include, without limitation, insertions, substitutions, and deletions.

An amine dehydrogenase can have any combination of amino acid substitutions, deletions or insertions. In one embodiment, the AmDH has an integer number of amino acid alterations such that its amino acid sequence shares at least 60, 70, 80, 85, 90, 95, 97, 98, 99, or 99.5% identity with an amino acid sequence of a reference or scaffold sequence.

Amino acid substitutions in an AmDH may be conservative or non-conservative substitutions. It is understood that substitutions at the recited amino acid positions can be made using any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine).

While the substitutions described herein are with respect specific amino acid dehydrogenase scaffolds, it is noted that one of ordinary skill in the art could readily make equivalent alterations in the corresponding polypeptides from other species, for example by sequence alignment.

The disclosed AmDHs exhibit amine dehydrogenase activity, however, it will be appreciated that different AmDHs will have different amine dehydrogenase activities, and potentially different specificities and activity toward various substrate ketones. Methods of determining amine dehydrogenase activity, and methods for screening for active AmDH in a AmDH library are discussed in more detail below. The AmDH can also be characterized by substrate specificity, enantioselectivity, rate of conversion, and theromstability. In some embodiments the AmDH has an enantioselectivity of 50, 60, 70, 80, 90, 95, 96, 97, 98, 99, or greater than 99% (enantiomeric excess). In some embodiments the AmDH has a conversion of substrate to product of 50, 60, 70, 80, 90, 95, 97, 98, 99, or greater than 99%. In some embodiments, the AmDH can convert 50, 60, 70, 80, 90, 95, 96, 97, 98, 99, or greater than 99% of substrate to product in 10 or fewer days, preferable 5 or fewer days, more preferably 3 or fewer days, most preferably 2 or fewer days. In preferred embodiment the AmDH has both an enantioselectivity (enantiomeric excess) and a conversion of 50, 60, 70, 80, 90, 95, 96, 97, 98, 99, or greater than 99% in 10 or fewer days, preferable 5 or fewer days, more preferably 3 or fewer days, most preferably 2 or fewer days. Thermostabiliy can be determined based on, for example, melting temperature, temperature verse activity profile, or a combination thereof. Preferably, the enzyme is both stable (i.e., folded) and active at temperatures of 10, 20, 30, 40, 45, 50, 55, 60, 65, 70, 80, 85° C., or greater.

Active fragments are of the AmDHs are also disclosed. Fragments of a full-length enzyme can retain functional activity of the enzyme. Functionally active fragments of the disclosed AmDHs typically retain amine dehydrogenase activity. The fragment can be less the 50, 50, 60, 70, 80, 85, 90, 95, 97, 98, 99, or 99.5% of the length of the full-length AmDH, or its full-length reference or scaffold amino acid dehydrogenase.

Amino acid sequences for exemplary AmDH and domains and chimeras thereof are provided below. The exemplary sequences can have 1, 2, 3, 4, 5, 6, 7, 8, 9, 10, or more additional amino acids on the N-terminus or C-terminus. For example, the amino acid sequences for the AmDH, and N-terminal fragments and chimeras thereof are provided without an N-terminal methionine. Therefore, in some embodiments the disclosed amino acid sequences include an N-terminal methionine. The amino acid sequences can also include additional sequences to enhance expression or purification of expressed protein. For example, the amino acid sequences can optional include a leader sequence to enhance secretion, or a purification tag to facilitate purification. The additional sequences can be added to the N-terminal or C-terminal end of the amino acid sequences provided below.

A. PheDH-AmDH

In some embodiments, the AmDH is engineered using a phenylalanine dehydrogenase (PheDH) backbone or scaffold, referred to as a PheDH-AmDH and F-AmDH. The PheDH-AmDH is typically a modified version of a reference PheDH and has amine dehydrogenase activity. A reference PheDH typically has phenylalanine dehydrogenase activity, but little or no amine dehydrogenase activity. The reference PheDH can be a naturally occurring, or non-naturally occurring PheDH. In some embodiments, the phenylalanine dehydrogenase activity of the PheDH-AmDH is reduced or absent compared to a reference PheDH.

In some embodiments, the reference PheDH has the amino acid sequence:
SLVEKTSIIKDFTLFEKMSEHEQV-VFCNDPATGLRAIIAIHDTTLGPALGGCRM QPYNS-VEEALEDALRLSKGMTYKCAASDVD-FGGGKAVIIGDPQKDKSPELFRAF GQFVDSLGGRFYTGTDMGTNMEDFI-HAMKETNCIVGVPEAYGGGGDSSIPTAMG VLY-GIKATNKMLFGKDDLG-GVTYAIQGLGKVGYKVAEGLLEEGAHLFVTDINEQ TLEAIQEKAKTTSGSVTVVAS-DEIYSQEADVFVPCAFGGVVNDETMKQFKVKAI AGSANNQLLTEDHGRHLADKGILYAP-DYIVNSGGLIQVADELYEVNKERVLAKT KHIYDAI-LEVYQQAELDQITTMEAANRMCEQR-MAARGRRNSFFTSSVKPKWDIR N
(SEQ ID NO:1, PheDH from *Bacillus badius*). Therefore, a PheDH-AmDH can be a variant of SEQ ID NO:1 with one or more insertions, deletions, or substitutions relative to SEQ ID NO:1, that has amine dehydrogenase activity.

In some embodiments the PheDH-AmDH is a variant of a PheDH such as SEQ ID NO:1 that contains a substitution of the lysine at position 77, substitution of the threonine at position 123, a substitution of the asparagine at position 276, or a combination thereof. In some embodiments, a recombinant Phe-AmDH amine dehydrogenase includes and amino acid sequence having at least 75%, 80%, 85%, 90%, 95%, 96%, 97%, 98%, or 99% sequence identity to SEQ ID NO:1, wherein the lysine at position 77 of SEQ ID NO:1 is substituted with an alternative amino acid including, but not limited to, a methionine, a serine, or a tryptophan, and the asparagine at position 276 of SEQ ID NO:1 is substituted with an alternative amino acid including but, not limited to, a valine, a leucine, or a glutamic acid. For example, the PheDH-AmDH can be a variant of a PheDH, for example a variant of SEQ ID NO:1, that contains a K77M substitution, a K77S substitution, or a K77W substitution. The PheDH-AmDH can be a variant of a PheDH, for example a variant of SEQ ID NO:1, that contains a N276V substitution, a N276L substitution, or a N276E substitution.

In one preferred embodiment, the PheDH-AmDH is variant of SEQ ID NO:1 with a K77S substitution in combination with a N276L substitution (also referred to as a "K77S/N276L" variant).

Therefore, a K77S/N276L AmDH can have the amino acid sequence SLVEKTSIIKDFTLFEKMSEHEQV-VFCNDPATGLRAIIAIHDTTLGPALGGCRM QPYNS-VEEALEDALRLSKGMTYSCAASDVD-FGGGKAVIIGDPQKDKSPELFRAF GQFVDSLGGRFYTGTDMGTNMEDFI-HAMKETNCIVGVPEAYGGGGDSSIPTAMG VLY-GIKATNKMLFGKDDLG-GVTYAIQGLGKVGYKVAEGLLEEGAHLFVTDINEQ TLEAIQEKAKTTSGSVTVVAS-DEIYSQEADVFVPCAFGGVVNDETMKQFKVKAI AGSANLQLLTEDHGRHLADKGILYAP-DYIVNSGGLIQVADELYEVNKERVLAKT KHIYDAI-LEVYQQAELDQITTMEAANRMCEQR-MAARGRRNSFFTSSVKPKWDIR N
(SEQ ID NO:2), or a variant thereof with 75%, 80%, 85%, 90%, 95%, 96%, 97%, 98%, or 99% sequence identity to SEQ ID NO:2), a serine at position 77, a leucine at position 276, and amine dehydrogenase activity.

In an alternative embodiment, the PheDH-AmDH is a variant of SEQ ID NO:1 with a K77W substitution in combination with a N276E substitution (also referred to as a "K77W/N276E" variant). Mutations relative to SEQ ID NO:1 are shown in bold.

Therefore, the K77W/N276E AmDH can have the amino acid sequence SLVEKTSIIKDFTLFEKMSEHEQV-VFCNDPATGLRAIIAIHDTTLGPALGGCRM QPYNS-VEEALEDALRLSKGMTYWCAASDVD- FGGGKAVIIGDPQKDKSPELFRAF
GQFVDSLGGRFYTGTDMGTNMEDFI-
HAMKETNCIVGVPEAYGGGGDSSIPT AMGVLY-
GIKATNKMLFGKDDLG-
GVTYAIQGLGKVGYKVAEGLLEEGAHLFVTDI
NEQTLEAIQEKAKTTSGSVTVVAS-
DEIYSQEADVFVPCAFGGVVNDETMKQFKV KAIAG-
SANEQLLTEDHGRHLADKGILYAP-
DYIVNSGGLIQVADELYEVNKERVL
AKTKHIYDAILEVYQQAELDQITT-
MEAANRMCEQRMAARGRRNSFFTSSVKPKW DIRN
(SEQ ID NO:3), or a variant thereof with 75%, 80%, 85%, 90%, 95%, 96%, 97%, 98%, or 99% sequence identity to SEQ ID NO:3, a tryptophan at position 77, a glutamic acid at position 276, and amine dehydrogenase activity. Mutations relative to SEQ ID NO:1 are shown in bold.

Sekimoto et al., *J. Biol. Chem.*, 36:27039-27045 (1993) reported that residues Lys79 and Asp114 of leucine dehydrogenase from *Bacillus stereothermophilus* (SEQ ID NO:4) are needed for the enzyme's catalytic mechanism. These residues correspond to residues Lys89 and Asp124 of PheDH from *Bacillus badius*, therefore in some embodiments, the Lys89, the Asp 124, or a combination thereof are not mutated. Accordingly, in some embodiments, the PheDH-AmDH disclosed herein are variants of SEQ ID NO:1, 2, or 3 that have a lysine at position 89, an aspartic acid at position 124, or a combination thereof.

Phe-DH from *Bacillus sphaericus, Rhodococcus* sp. M4, and *Sporosarcina ureae*, are related by sequence identity and similarity to the Phe-DH *Bacillus badius* Bachelor (SEQ ID NO:1), and have well characterized activities and substrate profiles present in literature (Brunhuber, et al., *Biochemistry*, 39, (31): 9174-9187 (2000); Asano, et al., *Journal of Biological Chemistry*, 262, (21): 10346-54 (1987); Asano, et., al., *European Journal of Biochemistry*, 168, (1): 153-159 (1987); Cooper., et al., *Analytical Biochemistry*, 183, (2): 210-214 (1989); Hummel, et al., *Applied Microbiology and Biotechnology*, 26, (5): 409-416 (1987); Seah., et al, *FEBS Letters*, 370, (12): 93-96 (1995). Therefore, in some embodiments, the scaffold of a PheDH-AmDH is the PheDH of *Bacillus sphaericus, Rhodococcus* sp. M4, or *Sporosarcina ureae*. Amino acid sequence for the PheDH of *Bacillus sphaericus, Rhodococcus* sp. M4, or *Sporosarcina ureae* are known in the art, the residues in the PheDH of *Bacillus sphaericus, Rhodococcus* sp. M4, or *Sporosarcina ureae* corresponding to K77 and N276 PheDH in *Bacillus badius* (SEQ ID NO:1), can be identified by sequence alignment and altered using the mutational strategies disclosed herein, particularly those discussed above with respect to SEQ ID NO:2 and SEQ ID NO:3.

B. LeuDH-AmDH

In some embodiments, the AmDH is engineered from a leucine dehydrogenase (PheDH) scaffold, referred to as a LeuDH-AmDH and L-AmDH. The LeuDH-AmDH is typically a variant of a reference LeuDH and has amine dehydrogenase activity. A reference LeuDH typically has leucine dehydrogenase activity, but little or no amine dehydrogenase activity. The reference LeuDH can be a naturally occurring, or non-naturally occurring LeuDH. In some embodiments, the phenylalanine dehydrogenase activity of the LeuDH-AmDH is reduced or absent compared to a reference LeuDH.

In some embodiments, the reference LeuDH has the amino acid sequence:
ELFQYMEKYDYEQVLFCQDKESGLKAI-
IVIHDTTLGPALGGTRMWMYNSEEEAL EDALR-
LARGMTYKNAAAGLNLGGGKTVIIGD-
PRKDKNEAMFRAFGRFIQGLNGR
YITAEDVGTTVADMDIIYQETDYVT-
GISPEFGSSGNPSPATAYGVYRGMKA AAKEAFGSD-
SLEGKVVAVQGVGNVAYHLCRHLHEE-
GAKLIVTDINKEAVARAVE
EFGAKAVDPNDIYGVECDIFAPCALGGI-
INDQTIPQLKAKVIAGSADNQLKEPR HGDMIHEM-
GIVYAPDYVINAGGVINVADELYGYNR-
ERAMKKIEQIYDNIEKVFA
IAKRDNIPTYVAADRMAEERIETMRKAR-
SQFLQNGHHILSRRRAR (SEQ ID NO:4, LeuDH from *Bacillus stearothermophilus*). Therefore, a LeuDH-AmDH can be a variant of SEQ ID NO:4 with one or more insertions, deletions, or substitutions relative to SEQ ID NO:4, that has amine dehydrogenase activity.

In some embodiments the LeuDH-AmDH is a variant of a LeuDH such as SEQ ID NO:4 that contains a substitution of the lysine at position 67, substitution of the glutamic acid at position 113, a substitution of the asparagine at position 261, a substitution of the valine at position 290, or a combination thereof. For example, the LeuDH-AmDH can be a variant of a LeuDH, for example a variant of SEQ ID NO:4, that contains a K67M substitution or a K67S substitution. The LeuDH-AmDH can be a variant of a LeuDH, for example a variant of SEQ ID NO:4, that contains a E113V substitution. The LeuDH-AmDH can be a variant of a LeuDH, for example a variant of SEQ ID NO:4), that contains a N261C substitution, a N261V substitution, or a N261L substitution. The LeuDH-AmDH can be a variant of a LeuDH, for example a variant of SEQ ID NO:4, that contains a V290C substitution.

In some embodiments, the LeuDH-based amine dehydrogenase includes an amino acid sequence having at least 75%, 80%, 85%, 90%, 95%, 96%, 97%, 98%, or 99% sequence identity to SEQ ID NO:4, wherein the lysine at position 67 of SEQ ID NO:4 is substituted with an alternative amino acid including, but not limited to, a methionine or a serine, and the glutamic acid at position 113 of SEQ ID NO:4 is substituted with an alternative amino acid, including, but not limited to a valine. In some embodiments, the LeuDH-based amine dehydrogenase the asparagine at position 261 of SEQ ID NO:4 is substituted with an alternative amino acid, including, but not limited to, a valine, a leucine, or a cysteine. In some embodiments, the LeuDH-based amine dehydrogenase the valine at position 290 of SEQ ID NO:4 is substituted with an alternative amino acid including, but not limited to, a cysteine.

In one preferred embodiment, the LeuDH-AmDH is a variant of SEQ ID NO:4 with a K67M substitution in combination with a E113V substitution (also referred to as a "K67M/E113V" variant).

Therefore, a K67M/E113V AmDH can have the amino acid sequence ELFQYMEKYDYEQVLFCQDKESGLKAI-
IVIHDTTLGPALGGTRMWMYNSEEEAL EDALR-
LARGMTYMNAAAGLNLGGGKTVIIGD-
PRKDKNEAMFRAFGRFIQGLNGR
YITAVDVGTTVADMDIIYQETDYVT-
GISPEFGSSGNPSPATAYGVYRGMKA AAKEAFGSD-
SLEGKVVAVQGVGNVAYHLCRHLHEE-
GAKLIVTDINKEAVARAVE
EFGAKAVDPNDIYGVECDIFAPCALGGI-
INDQTIPQLKAKVIAGSADNQLKEPR HGDMIHEM-
GIVYAPDYVINAGGVINVADELYGYNR-
ERAMKKIEQIYDNIEKVFA
IAKRDNIPTYVAADRMAEERIETMRKAR-
SQFLQNGHHILSRRRAR (SEQ ID NO:5), or a variant thereof with 75%, 80%, 85%, 90%, 95%, 96%, 97%, 98%, or 99% sequence identity to SEQ ID NO:5, a methionine at position 67, a valine at position 113, and amine dehydrogenase activity. Mutations relative to SEQ ID NO:4 are shown in bold.

In some embodiments, the K67M/E113V AmDH also includes a substitution at position 261, position 290, or a combination thereof.

For example, the variant can be a K67M/E113V/N261V AmDH with the amino acid sequence
ELFQYMEKYDYEQVLFCQDKESGLKAI-
IVIHDTTLGPALGGTRMWMYNSEEEAL EDALR-
LARGMTYMNAAAGLNLGGGKTVIIGD-
PRKDKNEAMFRAFGRFIQGLNGR
YITAVDVGTTVADMDIIYQETDYVT-
GISPEFGSSGNPSPATAYGVYRGMKA AAKEAFGSD-
SLEGKVVAVQGVGNVAYHLCRHLEE-
GAKLIVTDINKEAVARAVE
EFGAKAVDPNDIYGVECDIFAPCALGGI-
INDQTIPQLKAKVIAGSADVQLKEPR HGDMIHEM-
GIVYAPDYVINAGGVINVADELYGYNR-
ERAMKKIEQIYDNIEKVFA
IAKRDNIPTYVAADRMAEERIETMRKAR-
SQFLQNGHHILSRRRAR (SEQ ID NO:6), or a variant thereof with 75%, 80%, 85%, 90%, 95%, 96%, 97%, 98%, or 99% sequence identity to SEQ ID NO:6, a methionine at position 67, a valine at position 113, a valine at position 261 and amine dehydrogenase activity. Mutations relative to SEQ ID NO:4 are shown in bold.

Alternatively, the variant can be a K67M/E113V/N261C AmDH with the amino acid sequence
ELFQYMEKYDYEQVLFCQDKESGLKAI-
IVIHDTTLGPALGGTRMWMYNSEEEAL EDALR-
LARGMTYMNAAAGLNLGGGKTVIIGD-
PRKDKNEAMFRAFGRFIQGLNGR
YITAVDVGTTVADMDIIYQETDYVT-
GISPEFGSSGNPSPATAYGVYRGMKA AAKEAFGSD-
SLEGKVVAVQGVGNVAYHLCRHLEE-
GAKLIVTDINKEAVARAVE
EFGAKAVDPNDIYGVECDIFAPCALGGI-
INDQTIPQLKAKVIAGSADCQLKEPR HGDMIHEM-
GIVYAPDYVINAGGVINVADELYGYNR-
ERAMKKIEQIYDNIEKVFA
IAKRDNIPTYVAADRMAEERIETMRKAR-
SQFLQNGHHILSRRRAR (SEQ ID NO:7), or a variant thereof with 75%, 80%, 85%, 90%, 95%, 96%, 97%, 98%, or 99% sequence identity to SEQ ID NO:7, a methionine at position 67, a valine at position 113, a cysteine at position 261 and amine dehydrogenase activity. Mutations relative to SEQ ID NO:4 are shown in bold.

The variant can be a K67M/E113V/N261V/V290C AmDH with the amino acid sequence
ELFQYMEKYDYEQVLFCQDKESGLKAI-
IVIHDTTLGPALGGTRMWMYNSEEEAL EDALR-
LARGMTYMNAAAGLNLGGGKTVIIGD-
PRKDKNEAMFRAFGRFIQGLNGR
YITAVDVGTTVADMDIIYQETDYVT-
GISPEFGSSGNPSPATAYGVYRGMKA AAKEAFGSD-
SLEGKVVAVQGVGNVAYHLCRHLEE-
GAKLIVTDINKEAVARAVE
EFGAKAVDPNDIYGVECDIFAPCALGGI-
INDQTIPQLKAKVIAGSADVQLKEPR HGDMIHEM-
GIVYAPDYVINAGGCINVADELYGYNR-
ERAMKKIEQIYDNIEKVFA
IAKRDNIPTYVAADRMAEERIETMRKAR-
SQFLQNGHHILSRRRAR
(SEQ ID NO:8), or a variant thereof with 75%, 80%, 85%, 90%, 95%, 96%, 97%, 98%, or 99% sequence identity to SEQ ID NO:8, a methionine at position 67, a valine at position 113, a valine at position 261, a cysteine at position 290 and amine dehydrogenase activity. Mutations relative to SEQ ID NO:4 are shown in bold.

Alternatively, the variant can be a K67M/E113V/N261C/V290C AmDH with the amino acid sequence
ELFQYMEKYDYEQVLFCQDKESGLKAI-
IVIHDTTLGPALGGTRMWMYNSEEEAL EDALR-
LARGMTYMNAAAGLNLGGGKTVIIGD-
PRKDKNEAMFRAFGRFIQGLNGR
YITAVDVGTTVADMDIIYQETDYVT-
GISPEFGSSGNPSPATAYGVYRGMKA AAKEAFGSD-
SLEGKVVAVQGVGNVAYHLCRHLEE-
GAKLIVTDINKEAVARAVE
EFGAKAVDPNDIYGVECDIFAPCALGGI-
INDQTIPQLKAKVIAGSADCQLKEPR HGDMIHEM-
GIVYAPDYVINAGGCINVADELYGYNR-
ERAMKKIEQIYDNIEKVFA
IAKRDNIPTYVAADRMAEERIETMRKAR-
SQFLQNGHHILSRRRAR
(SEQ ID NO:9), or a variant thereof with 75%, 80%, 85%, 90%, 95%, 96%, 97%, 98%, or 99% sequence identity to SEQ ID NO:9, a methionine at position 67, a valine at position 113, a cysteine at position 261, and cysteine at position 290 and amine dehydrogenase activity. Mutations relative to SEQ ID NO:4 are shown in bold.

In some embodiments, the alteration at position 67 is substitution of lysine for serine. For example, a LeuDH-AmDH can be a be a LeuDH variant with K67S substitution such as in the K67S/E113V/N261L/V290C AmDH with the amino acid sequence
ELFQYMEKYDYEQVLFCQDKESGLKAI-
IVIHDTTLGPALGGTRMWMYNSEEEAL EDALR-
LARGSTYMNAAAGLNLGGGKTVIIGD-
PRKDKNEAMFRAFGRFIQGLNGR
YITAVDVGTTVADMDIIYQETDYVT-
GISPEFGSSGNPSPATAYGVYRGMKA AAKEAFGSD-
SLEGKVVAVQGVGNVAYHLCRHLEE-
GAKLIVTDINKEAVARAVE
EFGAKAVDPNDIYGVECDIFAPCALGGI-
INDQTIPQLKAKVIAGSADLQLKEPR HGDMIHEM-
GIVYAPDYVINAGGCINVADELYGYNR-
ERAMKKIEQIYDNIEKVFA
IAKRDNIPTYVAADRMAEERIETMRKAR-
SQFLQNGHHILSRRRAR
(SEQ ID NO:10), or a variant thereof with 75%, 80%, 85%, 90%, 95%, 96%, 97%, 98%, or 99% sequence identity to SEQ ID NO:10, a serine at position 67, a valine at position 113, a leucine at position 261, a cysteine at position 290, and amine dehydrogenase activity. Mutations relative to SEQ ID NO:4 are shown in bold.

In some embodiments, the aspartic acid at position 260 of SEQ ID NO:4 is a substituted with an alternative amino acid, including, but not limited to, an leucine. Therefore, a LeuDH-AmDH has an amino acid sequence of SEQ ID NO:4, 5, 6, 7, 8, 9, or 10, or functional fragment or variant thereof, with the aspartic acid at position 260 is substituted with an alternative amino acid. In some embodiments, the alternative amino acid is a leucine.

For example, in some embodiments, the C-terminal 227 amino acids of SEQ ID NO:4, 5, 6, 7, 8, 9, or 10, or functional fragment or variant thereof, is substituted with
GSSGNPSPATAYGVYRGMKAAAKEAFGS-
DSLEGKVVAVQGVGNVAYHLCRHLHE EGAKLIVT-
DINKEAVARAVEEFGAKAVDPNDIYGV-
ECDIFAPCALGGIINDQTI
PQLKAKVIAGSALNQLKEPRHGDMIHEM-
GIVYAPDYVINAGGCINVADELYGYN RERAMKKIE-
QIYDNIEKVFAIAKRDNIPTY-
VAADRMAEERIETMRKARSQFLQN GHHILSRRRAR (SEQ ID NO:17), which contains a D260L substitution relative to the corresponding 227 C-terminal amino acids of SEQ ID NO:4. The mutation relative to SEQ ID NO:4 are shown in bold.

In some embodiments, the amino acid of the LeuDH-AmDH at position 260 is an asparagine.

Sekimoto et al., *J. Biol. Chem.*, 36:27039-27045 (1993) reported that residues Lys79 and Asp114 of leucine dehydrogenase from *Bacillus stereothermophilus* (SEQ ID NO:4) are needed for the enzyme's catalytic mechanism. Therefore in some embodiments, the Lys79, the Asp114, or a combination thereof are not mutated. Accordingly, in some embodiments, the LeuDH-AmDH disclosed herein are variants of SEQ ID NO:4, 5, 6, 7, 8, 9, or 10, have lysine at position 79, aspartic acid at position 114, or a combination thereof.

C. Alternative Scaffolds

Leucine dehydrogenase from *Bacillus stearothermophilus* (SEQ ID NO:4), the scaffold of the LeuDH-AmDH disclosed above, belongs to the Glu-Leu-Phe-Val dehydrogenase sub-family (NCBI Accession number: cd05211) of proteins. Other members of this family of enzymes can be used as scaffolds for the variant amino acid dehydrogenases with amine dehydrogenase activity disclosed herein.

The enzymes of this family are closely related in structure and function. Each enzyme similarly catalyzes the reversible amination and deamination of their respective keto- and amino acids with free ammonia, and is facilitated by the hydride transfer of an NAD(P)H cofactor. These enzymes consist of two domains separated by a deep cleft. One domain is responsible for binding the substrate and contains residues involved in catalysis (Brunhuber, et. Al., *Critical Reviews in Biochemistry and Molecular Biology*, 29, (6): 415-467 (1984); Kataoka, et al., *Journal of Biochemistry*, 116, (4): 931-936 (1994)). The other domain is responsible for binding the cofactor containing a characteristic βαβ structure, known as the Rossmann fold, and is highly conserved among these dehydrogenases (Liu, et al., *Nat Struct Mol Biol*, 4, (4): 317-326 (1997). This conserved structure and functionality makes the Glu-Leu-Phe-Val dehydrogenase sub-family part of the larger domain superfamily NADB_Rossmann (Accession number: cl09931); identifiable through the NCBI's Conserved Domain Database (Marchler-Bauer, et al., *Nucleic Acids Research*, 2010).

The Examples below show that K67 substitution (i.e., K67M or K67S) and N261 substitution (i.e, N261V, N261C, or N261L) (LeuDH nomenclature and equivalent PheDH residues) are important for amination activity. The mutation of these residues is believed to be broadly applicable across the Glu-Leu-Phe-Val dehydrogenase sub-family of enzymes.

The Glu-Leu-Phe-Val dehydrogenase sub-family (NCBI Accession number: cd05211) contains a large number of characterized proteins which are further divided into smaller sub-families. The *B. stearothermophilus* LeuDH, *Rhodococcus* sp. M4 PheDH and *B. badius* PheDH all exist within this large sub-family, and are even further grouped in a smaller sub-family NAD_bind_Leu_Phe_Val_DH (Accession number: cd01075). This smaller sub-family grouping is a result of their highly conserved binding motifs of the NADH cofactor. Glutamate dehydrogenases (GluDH) are not a part of this smaller family, but are grouped into two separate GluDH subfamilies (Accession number: cd01076 and cd05313) within the greater Glu-Leu-Phe-Val dehydrogenase sub-family. Consequently, ValDH exhibits a much higher sequence identity to PheDH and LeuDH (typically greater than 60%), and GluDHs are more distant relatives (typically near 30% identity).

Accordingly, in some embodiments the scaffold is a GluDH, or more preferably a ValDH scaffold.

Figure 19:
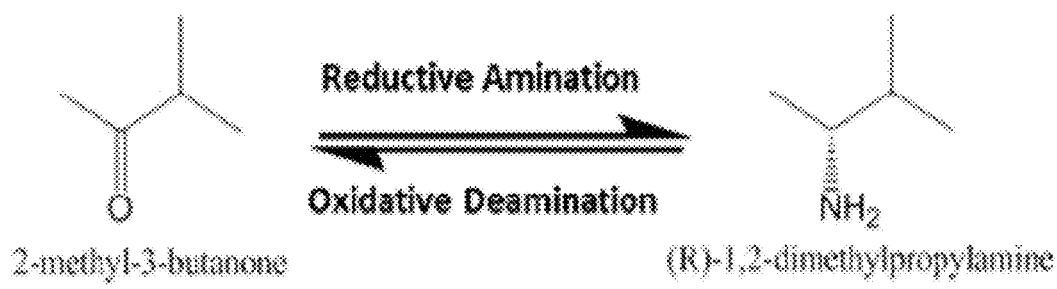
FIG. 19 is a reaction scheme the desired reductive amination activity of ValDH-AmDH converting 2-methyl-3-butanone to (R)-1,2-dimethylpropylamine.

Three exemplary ValDH scaffolds are from the *Streptomyces* genus of Actinobacteria: *Streptomyces coelicolor* (Navarrete, et al., *Journal of General Microbiology*, 136, (2): 273-281 (1990); Tang, et al., *Journal of Bacteriology*, 175, (13): 4176-4185 (1993); Turnbull, et al., *Journal of Biological Chemistry*, 272, (40): 25105-25111 (1997)), *Streptomyces fradiae* (Nguyen, et al., *Microbiology*, 141, (5): 1139-1145 (1995); Tang, et al., *Journal of Bacteriology*, 176, (19): 6107-6119 (1994); Vancura, et al., *Journal of General Microbiology*, 134, (12): 3213-3219 (1998)), and *Streptomyces cinnamonensis* (Turnbull, et al., *Journal of Biological Chemistry*, 272, (40): 25105-25111 (1997); Leiser, et al., *Gene*, 177, (12): 217-222 (1996); Priestley, et al., *The Biochemical Journal*, 261, (3): 853-861 (1989)). A resulting ValDH-based AmDH (ValDH-AmDH) would convert 2-methyl-3-butanone to chiral 1,2-dimethylpropylamine (FIG. 19).

For example, the ValDH scaffold can have the amino acid sequence TEADNGVLHTLFHSDQGGHEQVVLCQ-DRASGLKAVIAIHSTALGPALGGTRFYP YATEEEAV-ADVLNLSRGMSYKNAMAGLDHGGGKAVI-IGDPEQIKSEDLLLAFGR
FVASLGGRYVTACDVGTYVADMDVVARE-CRWTTGRSPENGGAGDSSVLTAF GVFQGMRASAE-HLWGDPSLRGRKVGVAGVGKVGHHLVE-HLLEDGADVVITDVRE
ESVNRSTHKHPSVTAVADTEALIRTEG-LDIYAPCALGGALDDDSVPVLTAKVVC GAAN-NQLAHPGVEKDLADRSILYAPDYVVNAG-GVIQVADELRGFDFDRCKAKAS
KIFDTTLAIFARAKEDGIPPAAAADRIAEQRMSDAR
(SEQ ID NO:11, ValDH from *Streptomyces cinnamonensis*).

A ValDH-AmDH can be a variant of ValDH from *S. cinnamonensis*, having a substitution of the lysine at position 75, substitution of the asparagine at position 272, or a combination thereof. In some embodiments, a ValDH-based amine dehydrogenase includes an amino acid sequence having 75%, 80%, 85%, 90%, 95%, 96%, 97%, 98%, or 99% sequence identity to SEQ ID NO:11, wherein the lysine at position 75 of SEQ ID NO:11 is substituted with an alternative amino acid including, but not limited to, a methionine or a serine and the asparagine at position 272 of SEQ ID NO:11 is substituted with an alternative amino acid including, but not limited to, a valine, a leucine, or a cysteine. In some embodiments, the variant has a K75S or a K75M substitution; a N272V, a N272C, or a N272L substitution; or a combination thereof.

For example, the ValDH-AmDH is a K75S/N272L variant with the amino acid sequence
TEADNGVLHTLFHSDQGGHEQVVLCQ-DRASGLKAVIAIHSTALGPALGGTRFYP YATEEEAV-ADVLNLSRGMSYSNAMAGLDHGGGKAVI-IGDPEQIKSEDLLLAFGR
FVASLGGRYVTACDVGTYVADMDVVARE-CRWTTGRSPENGGAGDSSVLTAFGVF QGMRASAE-HLWGDPSLRGRKVGVAGVGKVGHHLVE-HLLEDGADVVITDVREESV
NRSTHKHPSVTAVADTEALIRTEG-LDIYAPCALGGALDDDSVPVLTAKVVCGAA NLQLAHPGVEKDLADRSILYAPDYV-VNAGGVIQVADELRGFDFDRCKAKASKIF DTTLAI-FARAKEDGIPPAAAADRIAEQRMSDAR
(SEQ ID NO:12), or a variant thereof with 75%, 80%, 85%, 90%, 95%, 96%, 97%, 98%, or 99% sequence identity to SEQ ID NO:12, a serine at position 75, leucine at position 272, and amine dehydrogenase activity. Mutations relative to SEQ ID NO:11 are shown in bold.

D. Chimeric Amine Dehydrogenases

The AmDH can be a chimeric amine dehydrogenase that includes at least one domain derived from at least two different amino acid dehydrogenase scaffolds. The AmDH disclosed herein can be characterized as having at least two functional domains, a substrate binding domain (i.e., a ketone binding domain) and a co-factor binding (i.e., NADH) domain. Therefore, in some embodiments, the chimeric AmDH is a fusion protein that includes a substrate binding domain from a first AmDH and a cofactor binding domain from a second AmDH.

Fusion proteins disclosed herein can have the formula I:

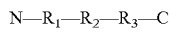

wherein "N" represents the N-terminus of the fusion protein, "C" represents the C-terminus of the fusion protein, "$R_1$" is a substrate binding domain from a first AmDH, "$R_2$" is an optional peptide/polypeptide linker domain, and "$R_3$" is a co-factor binding domain from a second AmDH. Alternatively, $R_3$ can be the substrate binding domain from a first AmDH and $R_1$ can be the co-factor binding domain from a second AmDH.

In some embodiments, 10, 20, 30, 40, 50, 60, 70, 80, 90, or more than 90% of the fusion protein is derived from the first AmDH and the remainder of the fusion protein is derived from the second AmDH alone, or in combination with an option linker, or other domain(s) such as a purification tag that are not derived from the first or second AmDH. In some embodiments, 10, 20, 30, 40, 50, 60, 70, 80, 90, or more than 90% of the fusion protein is derived from the second AmDH and the remainder of the fusion protein is derived from the first AmDH alone, or in combination with an optional linker, or other domain(s) such as a purification tag that are not derived from the first or second AmDH.

In some embodiments between about 25% and 75%, between about 30% and 70%, or between about 40% and 60% of the fusion protein is derived from the first AmDH and the remainder of the fusion protein is derived from the second AmDH alone, or in combination with an option linker, or other domain(s) that are not derived from the first or second AmDH. In some embodiments between about 25% and 75%, between about 30% and 70%, or between about 40% and 60% of the fusion protein is derived from the second AmDH and the remainder of the fusion protein is derived from the first AmDH alone, or in combination with an option linker, or other domain(s) that are not derived from the first or second AmDH.

In preferred embodiments, the first and second AmDHs are selected from the PheDH-AmDH, LeuDH-AmDH, and ValDH-AmDH disclosed herein. For example, in some embodiments, the first AmDH is a PheDH-AmDH and the second AmDH is a LeuDH-AmDH or a ValDH-AmDH. In some embodiments, the first AmDH is a LeuDH-AmDH and the second AmDH is a PheDH-AmDH or a ValDH-AmDH. In some embodiments, the first AmDH is a ValDH-AmDH and the second AmDH is a PheDH-AmDH or a LeuDH-AmDH. In some embodiments, the first and second AmDH are two different PheDH-AmDHs, two different LeuDH-AmDHs, or two different ValDH-AmDHs.

Exemplary substrate binding domains and co-factor binding domains for chimeric AmDH are provided below. The exemplary domains can have 1, 2, 3, 4, 5, 6, 7, 8, 9, 10, or more additional amino acids on the N-terminus or C-terminus. For example, the co-factor or substrate binding domains can be 1, 2, 3, 4, 5, 6, 7, 8, 9, 10, or more amino acids shorter, or longer than the exemplary domains provided below. The additional amino acids can be the corresponding amino acids from the wildtype amino acid dehydrogenase scaffold (for example, SEQ ID NO:1 (PheDH), SEQ ID NO:4 (LeuDH), or SEQ ID NO:11 (ValDH)).

a. Exemplary PheDH-AmDH Domains

The substrate binding domain of a PheDH-AmDH can be the N-terminal 149 amino acids of a PheDH-AmDH, or a functional fragment or variant thereof. Therefore, in some embodiments, the substrate binding domain of a PheDH-AmDH includes the N-terminal 149 amino acids of SEQ ID NO:2 or SEQ ID NO:3, or is a functional fragment or variant thereof.

For example, the substrate binding domain of a PheDH-AmDH can be SLVEKTSIIKDFTLFEKMSEHEQV-VFCNDPATGLRAIIAIHDTTLGPALGGCRM QPYNS-VEEALEDALRLSKGMTYSCAASDVDFGGGKAVIIGD PQKDKSPELFRAF GQFVDSLGGRFYTGTDMGT-NMEDFIHAMKETNCIVGVPEAY (SEQ ID NO:13), or a functional fragment or variant thereof.

The co-factor binding domain of a PheDH-AmDH can be the C-terminal 230 amino acids of a PheDH-AmDH, or a functional fragment or variant thereof. Therefore, in some embodiments, the substrate binding domain of a PheDH-AmDH includes the C-terminal 230 amino acids of SEQ ID NO:2 or SEQ ID NO:3, or is a functional fragment or variant thereof.

For example, the cofactor binding domain of a PheDH-AmDH can be GGGGDSSIPTAMGVLYGIKATNKMLF-GKDDLGGVTYAIQGLGKVGYKVAEGLLE EGAHL-FVTDINEQTLEAIQEKAKTTSGSVTVVASDEIYSQEA DVFVPCAFGGVV NDETMKQFKVKAIAGSANLQLLT-EDHGRHLADKGILYAPDYIVNSGGLIQVADE LYEVNKERVLAKTKHIYDAI-LEVYQQAELDQITTMEAANRMCEQRMAARGRRNS FFTSSVKPKWDIRN (SEQ ID NO:14), or a functional fragment or variant thereof.

b. Exemplary LeuDH-AmDH Domains

The substrate binding domain of a LeuDH-AmDH can be the N-terminal 139 amino acids of a LeuDH-AmDH, or a functional fragment or variant thereof. Therefore, in some embodiments, the substrate binding domain of a LeuDH-AmDH includes the N-terminal 139 amino acids of SEQ ID NO:5, 6, 7, 8, 9, or 10, or is a functional fragment or variant thereof.

For example, the substrate binding domain of a LeuDH-AmDH can be ELFQYMEKYDYEQVLFCQDKESGLKAI-IVIHDTTLGPALGGTRMWMYNSEEEAL EDALR-LARGSTYMNAAAGLNLGGGKTVIIGDPRKDKNEAM FRAFGRFIQGLNGR YITAVDVGTTVADMDIIYQET-DYVTGISPEF (SEQ ID NO:15), or a functional fragment or variant thereof.

The co-factor binding domain of a LeuDH-AmDH includes the C-terminal 227 amino acids of a LeuDH-AmDH, or a functional fragment or variant thereof. Therefore, in some embodiments, the substrate binding domain of a LeuDH-AmDH includes the C-terminal 227 amino acids of SEQ ID NO:5, 6, 7, 8, 9, or 10, or is a functional fragment or variant thereof.

For example, the cofactor binding domain of a LeuDH-AmDH can be GSSGNPSPATAYGVYRGM-KAAAKEAFGSDSLEGKVVAVQGVGN-VAYHLCRHLHE EGAKLIVTDINKEAVARAVEEFGAKAVD-PNDIYGVECDIFAPCALGGIINDQTI PQLKAKVIAG-SADLQLKEPRHGDMIHEMGIVYAPDYVI-NAGGCINVADELYGYN RERAMKKIEQIYDNIEKVFAIAKRDNIPTYVAADRMAEERIETMRKARSQFLQN GHHILSRRRAR
(SEQ ID NO:16) or a functional fragment or variant thereof;
or GSSGNPSPATAYGVYRGMKAAAKEAFGSDSLEGKVVAVQGVGNVAYHLCRHLHE EGAKLIVTDINKEAVARAVEEFGAKAVDPNDIYGVECDIFAPCALGGIINDQTIPQLKAKVIAGSALNQLKEPRHGDMIHEMGIVYAPDYVINAGGCINVADELYGYN RERAMKKIEQIYDNIEKVFAIAKRDNIPTYVAADRMAEERIETMRKARSQFLQN GHHILSRRRAR
(SEQ ID NO:17) or a functional fragment or variant thereof. Mutations relative to the corresponding 227 C-terminal amino acids in SEQ ID NO:4 are in bold.

c. Exemplary ValDH-AmDH Domains

In some embodiments, the substrate binding domain of a ValDH-AmDH includes the N-terminal 139 amino acids of a LeuDH-AmDH, or is a functional fragment or variant thereof. Therefore, in some embodiments, the substrate binding domain of a ValDH-AmDH includes the N-terminal 147 amino acids of SEQ ID NO:12, or is a functional fragment or variant thereof.

For example, the substrate binding domain of a ValDH-AmDH can be amino acids
TEADNGVLHTLFHSDQGGHEQVVLCQDRASGLKAVIAIHSTALGPALGGTRFYP YATEEEAVADVLNLSRGMSYSNAMAGLDHGGGKAVIIGDPEQIKSEDLLLAFGR FVASLGGRYVTACDVGTYVADMDVVARECRWTTGRSPEN
(SEQ ID NO:18), or a functional fragment or variant thereof.

The co-factor binding domain of a ValDH-AmDH includes the C-terminal 210 amino acids of a ValDH-AmDH, or a functional fragment or variant thereof. Therefore, in some embodiments, the substrate binding domain of a ValDH-AmDH includes the C-terminal 210 amino acids of SEQ ID NO:12 or is a functional fragment or variant thereof.

For example, the cofactor binding domain of a ValDH-AmDH can be amino acids
GGAGDSSVLTAFGVFQGMRASAEHLWGDPSLRGRKVGVAGVGKVGHHLVEHLLE DGADVVITDVREESVNRSTHKHPSVTAVADTEALIRTEGLDIYAPCALGGALDD DSVPVLTAKVVCGAANLQLAHPGVEKDLADRSILYAPDYVVNAGGVIQVADELR GFDFDRCKAKASKIFDTTLAIFARAKEDGIPPAAAADRIAEQRMSDAR
(SEQ ID NO:19), or a functional fragment or variant thereof.

d. Exemplary Chimeric AmDH

An exemplary chimeric AmDH is a fusion protein including a substrate binding domain from a PheDH-AmDH and a co-factor binding domain of a LeuDH-AmDH. The chimeric AmDH can have the amino acid sequence, SLVEKTSIIKDFTLFEKMSEHEQVVFCNDPATGLRAIIAIHDTTLGPALGGCRM QPYNSVEEALEDALRLSKGMTYSCAASDVDFGGGKAVIIGDPQKDKSPELFRAF GQFVDSLGGRFYTGTDMGTNMEDFIHAMKETNCIVGVPEAYGSSGNPSPATAYG VYRGMKAAAKEAFGSDSLEGKVVAVQGVGNVAYHLCRHLHEEGAKLIVTDINKE AVARAVEEFGAKAVDPNDIYGVECDIFAPCALGGIINDQTIPQLKAKVIAGSAL NQLKEPRHGDMIHEMGIVYAPDYVINAGGCINVADELYGYNRERAMKKIEQIYD NIEKVFAIAKRDNIPTYVAADRMAEERIETMRKARSQFLQNGHHILSRRRAR (SEQ ID NO:20), or
SLVEKTSIIKDFTLFEKMSEHEQVVFCNDPATGLRAIIAIHDTTLGPALGGCRM QPYNSVEEALEDALRLSKGMTYSCAASDVDFGGGKAVIIGDPQKDKSPELFRAF GQFVDSLGGRFYTGTDMGTNMEDFIHAMKETNCIVGVPEAYGSSGNPSPATAYG VYRGMKAAAKEAFGSDSLEGKVVAVQGVGNVAYHLCRHLHEEGAKLIVTDINKE AVARAVEEFGAKAVDPNDIYGVECDIFAPCALGGIINDQTIPQLKAKVIAGSAD LQLKEPRHGDMIHEMGIVYAPDYVINAGGCINVADELYGYNRERAMKKIEQIYD NIEKVFAIAKRDNIPTYVAADRMAEERIETMRKARSQFLQNGHHILSRRRAR (SEQ ID NO:21), or
SLVEKTSIIKDFTLFEKMSEHEQVVFCNDPATGLRAIIAIHDTTLGPALGGCRM QPYNSVEEALEDALRLSKGMTYSCAASDVDFGGGKAVIIGDPQKDKSPELFRAF GQFVDSLGGRFYTGTDMGTNMEDFIHAMKETNCIVGVPEAYGSSGNPSPATAYG VYRGMKAAAKEAFGSDSLEGKVVAVQGVGNVAYHLCRHLHEEGAKLIVTDINKE AVARAVEEFGAKAVDPNDIYGVECDIFAPCALGGIINDQTIPQLKAKVIAGSAL LQLKEPRHGDMIHEMGIVYAPDYVINAGGCINVADELYGYNRERAMKKIEQIYD NIEKVFAIAKRDNIPTYVAADRMAEERIETMRKARSQFLQNGHHILSRRRAR
(SEQ ID NO:22),
or a variant of SEQ ID NO:20, 21, or 22 with 75%, 80%, 85%, 90%, 95%, 96%, 97%, 98%, or 99% sequence identity to SEQ ID NO:20, 21, or 22, and amine dehydrogenase activity.

In some embodiments, the amino acid of the LeuDH-AmDH at position 270 of SEQ ID NO:20, 21, 22, or a functional fragment or variant thereof is an asparagine.

A second exemplary chimeric AmDH is a fusion protein including a substrate binding domain from a PheDH-AmDH and a co-factor binding domain of a ValDH-AmDH. The chimeric can have the amino acid sequence,
SLVEKTSIIKDFTLFEKMSEHEQVVFCNDPATGLRAIIAIHDTTLGPALGGCRM QPYNSVEEALEDALRLSKGMTYSCAASDVDFGGGKAVIIGDPQKDKSPELFRAF GQFVDSLGGRFYTGTDMGTNMEDFIHAMKETNCIVGVPEAYGGAGDSSVLTAFG VFQGMRASAEHLWGDPSLRGRKVGVAGVGKVGHHLVEHLLEDGADVVITDVREE SVNRSTHKHPSVTAVADTEALIRTEGLDIYAPCALGGALDDDSVPVLTAKVVCG AANLQLAHPGVEKDLADRSILYAPDYVVNAGGVIQVADELRGFDFDRCKAKASK IFDTTLAIFARAKEDGIPPAAAADRIAEQRMSDAR
(SEQ ID NO:23), or
MSLVEKTSIIKDFTLFEKMSEHEQVVFCNDPATGLRAIIAIHDTTLGPALGGCR MQPYNSVEEALEDALRLSKGMTYSCAASDVDFGGGKAVIIGDPQKDKSPELFRA FGQFVDSLGGRFYTGTDMGTNMEDFIHAMKETNCIVGVPEAYGGAGDSSVLTAF GVFQGMRASAEHLWGDPSLRGRKVGVAGVGKVGHHLVEHLLEDGADVVITDVRE ESVNRSTHKHPSVTAVADTEALIRTEGLDIYAPCALGGALDDDSVPVLTAKVVC GAANLQLAHPGVEKDLADRSILYAPDYVVNAGGVIQVADELRGFDFDRCKAKAS KIFDTTLAIFARAKEDGIPPAAAADRIAEQRMSDAR, (SEQ ID NO:24), or a variant of SEQ ID NO:23 or 24 with 75%, 80%, 85%, 90%, 95%, 96%, 97%, 98%, or 99% sequence identity to SEQ ID NO:23 or 24, and amine dehydrogenase activity.

Methods of using domain shuffling to create chimeric, enzymatic fusion proteins are known in the art and include those discussed in Kataoka, et al., *J. Biochem.*, 116:931-936 (1994), which is specifically incorporated by reference herein in its entirety.

E. Additional Modifications

1. Mutation Strategies

In some embodiments, the disclosed PheDH-AmDH, LeuDH-AmDH, ValDH-AmDH, or fragments or chimeras thereof include one or more additional amino acid alterations relative to the reference scaffold sequence that improves the catalytic constant $k_{cat}$, lowers the $K_M$ value, increases amine dehydrogenase activity, increases substrate binding, increases stability, for example, theromstability, or combinations thereof for the enzyme.

The first-shell residues of the active AmDHs, such as those identified in Table 1, are responsible for both direct interactions with active-site residues and binding of the substrate. In some embodiments, these residues are altered to improve protein-substrate interacts and resulting in increased catalytic constant $k_{cat}$ and a lower $K_M$ value.

High thermostability and activity of the enzyme catalyst are advantageous for achieving a robust industrial enzyme process. Numerous enzymes have been evolved to improve thermostability and tolerance to normative process conditions through a variety of strategies. These strategies include introduction of disulfide bonds (Mansfeld, et al., *Journal of Biological Chemistry*, 272, (17): 11152-11156 (1987)), improved core packing (Filikov, et. al., Protein Science, 11, (6): 1452-1461 (2002); Korkegian, et al., *Science*, 308, (5723): 857-860 (2005); Sheffler, et al., *Protein Science*, 18, (1): 229-239 (2009); Sheffler, et al., *Protein Science*, 19, (10): 1991-1995 (2010), increased rigidity (Reetz., et al., *Chemical Communications*, 46, (45): 8657-8658 (2010); Matthews, et al., *Proceedings of the National Academy of Sciences*, 84, (19): 6663-6667 (1987), and optimized surface charges (Strickler, et al., *Biochemistry*, 45, (9): 2761-2766 (2006); Wunderlich, et al., *Journal of Molecular Biology*, 347, (5): 1063-1076 (2005)).

Several online tools allow for the prediction of potential disulfide bond pairs, i.e. SS-BOND or GDAP (Hazes, et al., *Protein Engineering*, 2, (2): 119-125 (1988); O'Connor, et al., *Nucleic Acids Research*, 32, (Web Server Issue): W360-W364 (2004)). An example analysis of the *Rhodococcus* sp. M4 PheDH using SS-BOND can be found in Table 2.

TABLE 1

Alignment of binding pocket residues for *B. stearothermophilus* LeuDH, *Rhodococcus* sp. M4 PheDH, *B. badius* PheDH, and *S. cinnamonensis* VlDH.

| LeuDH | PheDH | | ValDH | |
| --- | --- | --- | --- | --- |
| *B. stearothermophilus* | *Rhodococcus* M4 | *Bacillus badius* | *Strep. Cinnamonensis* | Rationale for mutation |
| L39 | A38 | L49 | L47 | Residues interact with the para- |
| G40 | G39 | G50 | G48 | substituted region of the Phe substrate |
| G41 | G40 | G51 | G49 | |
| M64 | M63 | M74 | M72 | Side chain interactions with neighboring Lysine |
| K67 | K66 | K77 | K75 | Direct interaction with the carboxyl of the keto-acid substrate, along with Asn. |
| A112 | G116 | G122 | A120 | Residues interact with the posterior |
| E113 | P117 | T123 | C121 | portion of the substrate, opposite the |
| D114 | D118 | D124 | D122 | reacting ketone/amine. |
| V115 | V119 | M125 | V123 | |
| T133 | F137 | V143 | T141 | Residues interact with the para-substituted region of the Phe substrate |
| D260 Or N260 | N262 | N275 | N271 | |
| N261 | N263 | N276 | N272 | Direct interaction with the carboxyl of the keto-acid substrate, along with Lys. |
| V290 | A292 | L305 | V301 | Residues shape substrate binding |
| V293 | L295 | V308 | V304 | pocket |

For example, the residues A38 and F137 (Rh. sp. M4 PheDH) are of particular interest due to their interactions with the para-substituted region of the PheDH substrate. The para-fluoro substitution of phenyl acetone creates not only a larger, but more polar moiety at this position. Substituting the A38 with a more polar side chain, or decreasing the size of the F137 may lead to more favorable substrate binding. Accordingly, in some embodiments, the amino acid residues of the AmDH corresponding to A38 of Rh. sp. M4 PheDH, F137 of Rh. sp. M4 PheDH, or a combination thereof are altered. In some embodiments, residues corresponding to A38 and F138 are substituted with a polar amino acid, for example, serine, threonine, asparagine, or glutamine.

TABLE 2

Example output of SS-BOND in *Rhodococcus* sp. M4, PDB: 1C1D

| NR | RES1--RES2 | NAME1 | NAME2 | CB DIST | CA DIST |
| --- | --- | --- | --- | --- | --- |
| 1 | 5--50 | ALA | ALA | 4.454 | 5.915 |
| 2 | 5--53 | ALA | LEU | 3.961 | 6.224 |
| 3 | 10--30 | GLY | ASP | 4.314 | 4.301 |
| 4 | 12--29 | MET | LEU | 4.446 | 5.162 |
| 5 | 14--27 | VAL | ILE | 3.989 | 4.922 |
| 6 | 16--25 | ARG | PHE | 4.269 | 5.065 |
| 7 | 22--84 | GLY | PRO | 3.442 | 5.439 |
| 8 | 24--82 | HIS | ALA | 3.885 | 5.026 |

TABLE 2-continued

Example output of SS-BOND in *Rhodococcus* sp. M4, PDB: 1C1D

| NR | RES1--RES2 | NAME1 | NAME2 | CB DIST | CA DIST |
|---|---|---|---|---|---|
| 9  | 26--56   | VAL | ALA | 4.493 | 7.057 |
| 10 | 26--80   | VAL | VAL | 4.384 | 5.083 |
| 11 | 28--56   | ARG | ALA | 4.139 | 5.979 |
| 12 | 28--60   | ARG | ALA | 4.155 | 6.223 |
| 13 | 29--37   | LEU | ALA | 4.275 | 6.067 |
| 14 | 29--77   | LEU | GLY | 4.431 | 4.211 |
| 15 | 30--60   | ASP | ALA | 3.856 | 5.409 |
| 16 | 30--76   | ASP | GLY | 4.479 | 5.522 |
| 17 | 31--64   | SER | THR | 4.408 | 6.310 |
| 18 | 32--75   | THR | GLY | 4.076 | 4.389 |
| 19 | 35--74   | GLY | MET | 4.301 | 4.082 |
| 20 | 37--75   | ALA | GLY | 4.030 | 3.908 |
| 21 | 37--77   | ALA | GLY | 3.193 | 4.927 |
| 22 | 38--74   | ALA | MET | 4.353 | 6.422 |
| 23 | 38--114  | ALA | TRP | 4.489 | 4.724 |
| 24 | 39--63   | GLY | MET | 4.107 | 6.319 |
| 25 | 39--77   | GLY | GLY | 4.310 | 4.861 |
| 26 | 39--78   | GLY | LYS | 3.870 | 4.516 |
| 27 | 40--116  | GLY | GLY | 4.294 | 4.118 |
| 28 | 40--118  | GLY | ASP | 3.178 | 5.051 |
| 29 | 41--79   | THR | SER | 4.151 | 4.515 |
| 30 | 42--118  | ARG | ASP | 4.153 | 4.880 |
| 31 | 43--81   | ALA | ILE | 4.143 | 4.587 |
| 32 | 43--120  | ALA | ASN | 3.860 | 5.390 |
| 33 | 46--51   | TYR | ASP | 4.315 | 6.247 |
| 34 | 46--52   | TYR | ALA | 4.364 | 6.125 |
| 35 | 52--82   | ALA | ALA | 4.161 | 6.391 |

This algorithm approximates the location of β-carbon atoms from the position of the backbone, and screens this set for suitable β-carbon to β-carbon distances and bond angles favorable for a disulfide bond. The final confirmations are energy minimized and reported in the output. Accordingly, in some embodiments, one or more of the residues in an AmDH corresponding to the residues in Table 2 are altered to improve protein stabilization. For example, in some embodiments, the paired residues are substituted with cysteines, selenocysteines, or a combination thereof to introduce a disulfide or diselenide bond into the enzyme.

The tight packing of the protein's core can be important for stability, and the elimination of voids in the protein structure results in a decreased free energy. Software such as Rosetta-Holes2 and Rosetta$_{VIP}$ can be used for quantitative and visual assessment of the packing in the protein core. These flaws in core packing can then be improved by altering the amino acid sequence of the AmDH to create more energetically-favored folded protein states. Therefore, in some embodiments, amino acid sequence alterations are introduced into the amine dehydrogenase to increase packing, eliminate voids, improve stability, decrease free energy, or a combination thereof.

In one embodiment, AmDH can be modified to increase its stability in organic solvents by making conservative substations with amino acids having non-polar side chains.

2. Methods of Making Mutations

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

Methods of creating libraries of mutants for screening are known in the art, and described in the Examples below.

F. Nucleic Acid Molecules and Vectors

1. Isolated Nucleic Acids

Isolated nucleic acid sequences encoding AmDH are disclosed herein. As used herein, "isolated nucleic acid" refers to a nucleic acid that is separated from other nucleic acid molecules that are present in a mammalian genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids can be in sense or antisense orientation, or can be complementary to a reference sequence encoding an AmDH polypeptide.

Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoramidite, or an alkyl phosphotriester backbone.

The coding sequence can be genetically engineered by altering the coding sequence for optimal expression in the host of interest.

2. Vectors

Nucleic acids, such as those described above, can be inserted into vectors for expression in cells. As used herein, a "vector" is a replicon, such as a plasmid, phage, or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A.

II. Methods of Making Recombinant Amine Dehydrogenases

A. Expression of Encoded Proteins

The cDNA species encoding the disclosed AmDH can be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the disclosed enzymes.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene.

Recombinant cells include those having an introduced cDNA or genomic DNA, and also include genes positioned adjacent to a promoter not naturally associated with the particular introduced gene.

To express a recombinant encoded protein or peptide, whether mutant or wild-type, one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is often transformed using pBR322, a plasmid derived from an E. coli species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as E. coli LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, Autograph californica nuclear polyhidrosis virus (AcNPV) is used as a vector to express foreign genes. The virus grows in Spodoptera frugiperda cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect Spodoptera frugiperda cells in which the inserted gene is expressed.

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HinDIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides downstream of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited to, the herpes simplex virus thymidine kinase, hypoxanthine-guanine phosphoribosyltransferase and adenine phosphoribosyltransferase genes, in tk⁻, hgprt⁻ or aprt⁻ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

The AmDH can optionally include additional sequences or moieties, including, but not limited to linkers and purification tags.

In a preferred embodiment the purification tag is a polypeptide. Polypeptide purification tags are known in the art and include, but are not limited to His tags which typically include six or more, typically consecutive, histidine residues; FLAG tags, which typically include the sequence DYKDDDDK (SEQ ID NO:25); haemagglutinin (HA) for example, YPYDVP (SEQ ID NO:26); MYC tag for example ILKKATAYIL (SEQ ID NO:27) or EQKLISEEDL (SEQ ID NO:28). Methods of using purification tags to facilitate protein purification are known in the art and include, for example, a chromatography step wherein the tag reversibly binds to a chromatography resin.

Purifications tags can be N-terminal or C-terminal to the fusion protein. The purification tags N-terminal to the fusion protein are typically separated from the polypeptide of interest at the time of the cleavage in vivo. Therefore, purification tags N-terminal to the fusion protein can be used to remove the fusion protein from a cellular lysate following expression and extraction of the expression or solubility enhancing amino acid sequence, but cannot be used to remove the polypeptide of interest. Purification tags C-terminal to the fusion protein can be used to remove the polypeptide of interest from a cellular lysate following expression of the fusion protein, but cannot be used to remove the expression or solubility enhancing amino acid sequence. Purification tags that are C-terminal to the expression or solubility enhancing amino acid sequence can be N-terminal to, C-terminal to, or incorporated within the sequence of the polypeptide of interest.

In some embodiments, to fusion protein includes one or more linkers or spacers. In some embodiments linker or spacer is one or more polypeptides. In some embodiments, the linker includes a glycine-glutamic acid di-amino acid sequence. The linkers can be used to link or connect two domains, regions, or sequences of the fusion protein.

It is contemplated that the isolated nucleic acids of the invention may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

Although many proteins with therapeutic or commercial uses can be produced by recombinant organisms, the yield and quality of the expressed protein are variable due to many factors. For example, heterologous protein expression by genetically engineered organisms can be affected by the size and source of the protein to be expressed, the presence of an affinity tag linked to the protein to be expressed, codon biasing, the strain of the microorganism, the culture conditions of microorganism, and the in vivo degradation of the expressed protein. Some of these problems can be mitigated by fusing the protein of interest to an expression or solubility enhancing amino acid sequence. Exemplary expression or solubility enhancing amino acid sequences include maltose-binding protein (MBP), glutathione S-transferase (GST), thioredoxin (TRX), NUS A, ubiquitin (Ub), and a small ubiquitin-related modifier (SUMO).

In some embodiments, the compositions disclosed herein include expression or solubility enhancing amino acid sequence. In some embodiments, the expression or solubility enhancing amino acid sequence is cleaved prior administration of the composition to a subject in need thereof. The expression or solubility enhancing amino acid sequence can be cleaved in the recombinant expression system, or after the expressed protein in purified. In some embodiments, the expression or solubility enhancing is a ULP1 or SUMO sequence. Recombinant protein expression systems that incorporate the SUMO protein ("SUMO fusion systems") have been shown to increase efficiency and reduce defective expression of recombinant proteins in *E. coli.*, see for example Malakhov, et al., *J. Struct. Funct. Genomics,* 5: 75-86 (2004), U.S. Pat. No. 7,060,461, and U.S. Pat. No. 6,872,551. SUMO fusion systems enhance expression and solubility of certain proteins, including severe acute respiratory syndrome coronavirus (SARS-CoV) 3CL protease, nucleocapsid, and membrane proteins (Zuo et al., *J. Struct. Funct. Genomics,* 6:103-111 (2005)).

B. Purification of Expressed Proteins

Composition and methods for purification, or the substantial purification, of an encoded protein or peptide are also disclosed. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or p-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

III. Methods of Identifying and Testing Activity of Amine Dehydrogenases

Compositions and methods of screening a library of amino acid dehydrogenase variants for amine dehydrogenase activity and characterizing the amine dehydrogenase activity of an AmDH are disclosed.

A. Methods of Screening for Amine Dehydrogenase Activity

Methods of screening for amino acid dehydrogenase variants with amine dehydrogenase activity are known in the art and describe in the Examples below. For example, in some embodiments, AmDHs are identified as having amine dehydrogenase activity using a NAD+ auto-fluorescence assay, a formazan-based assay, a deamination of 1,3 DMBA assay, or a combination thereof.

1. NAD+Auto-fluorescence Assay

NAD+ auto-fluorescence assay are known in the art, see, for example, (Kaplan, et al., *Journal of Biological Chemistry,* 191, (2): 461-472 (1951); Lowry, et al., *J. Biol. Chem.,* 224: 1047-1064 (1957); Tsotsou, et al., *Biosensors and Bioelectronics,* 17, (12): 119-131 (2002)). In an optimal system, sensitivities as low as 0.01 µM NAD(P)+ fluorophore were observed (Seidemann, New York, N.Y. Academic Press (1973)). Generally, expression plates containing cell culture pellets are resuspended in Cell Lysing agent. The resulting cell lysate divided into two separate plates, one reaction plate and one background plate. For the background plate, reaction buffer only is added. No substrate is added to the background plate. A buffer can be, for example, 1.1 mM NADH in 500 mM $NH_4Cl/NH_4OH$ buffer pH 9.6 which will only result in background conversion rates. Reaction buffer containing a ketone substrate, such as MIBK, is added reaction plates. The plates are incubated for period of time to allow for conversion.

After reaction, the fluorophore is generated through a pH shift. First the residual NADH is removed by adjusting the pH to 1.0 through the addition of an acid, such as 6N HCl, and incubated for a suitable period of time, for example about 30 minutes. At this pH value, the NADH will rapidly degrade while leaving the stable NAD+. To create the NAD+ fluorescence, the pH value was re-adjust to >13.0 by adding a base, for example, 10 N NaOH and incubated in the dark for a suitable period of time, for example about 2.5 hours. Fluorescence can be measured using a spectrofluorometer at an excitation wavelength of 360 nm and emission wavelength of 455 nm.

Wells containing lysates from different AmDH can be ranked based upon the differential increase in fluorescence over the background plate. NAD+ concentrations can be distinguished as low as 1-2 µmol to above 100 µmol. This allows for the identification of very slight improvements in AmDH activity.

2. Formazan-Based Assay

Figure 4:
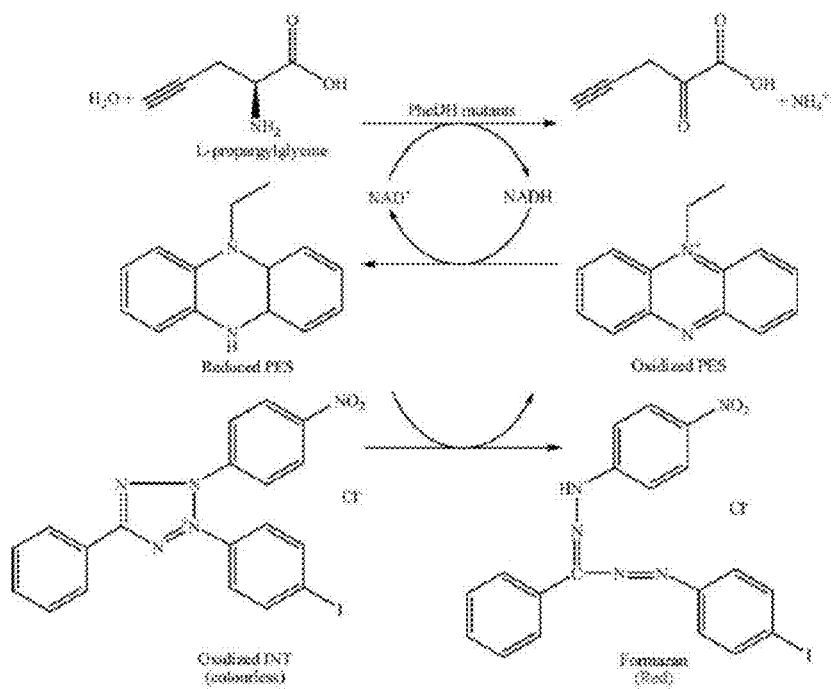
FIG. 4 is a diagram showing a formazan-based assay used for screening libraries 6 and 7 for active PheDH-AmDH mutants.

Formazan-based assays are known in the art, see, for example, (Chen, et al., *Journal of Biotechnology,* 142, (2): 127-134 (2009)). This assay takes advantage of the elevated activity in the deamination direction, giving the assay a good signal-to-noise ratio. The reaction scheme is represented in FIG. 4. The enzymatic deamination activity is related to conversion of NAD+ cofactor to produce NADH, which is re-oxidized back to NAD+ by phenazine ethosulfate. The resulting reduced PES subsequently reduces 2-(4-iodophenyl)-3-(4-nitrophenyl)-5-phenyltetrazolium chloride hydrate (INT, Sigma Aldrich) to create formazan. Formazan creates a deep red color which can be characterized by absorbance at 495 nm. Cell lysate are prepared as discussed above for the NAD+ auto-fluorescence assay. Deamination buffer, for example, 1 mM NAD+, a catalytic amount of PES, and 0.1 M glycine buffer at pH 10.0 is added to the background plate. The reaction plate buffer also contains a substrate, for example, 80 mM 1,3-DMBA. Plates are allowed to incubate for a suitable period, for example, 30 min at room temperature, and absorbance readings are taken.

3. Assay Measuring the Deamination of 1,3-DMBA

A third assay involves measuring the absorbencies at two wavelengths, 340 nm and 600 nm. The increased absorbance at 340 nm corresponds to the production of NADH in the deamination of 1,3-DMBA, while the 600 nm reading roughly estimates the biomass present in the well. The absorbance at 600 nm correlates strongly the background absorbance at 340 nm (see, for example, FIG. 6).

The absorbance at 340 nm is normalized by the 600 nm absorbance reading for both the reaction and background plates. Variants are scored by their proportional increase over the background observed in each well (Equation 1, below). This method reduces background noise of the assay by accounting for differences in expression levels, resulting in more accurate determination of enzymatic activity and decreasing false positives. The resulting quantity roughly estimates the specific activity of the overexpressed mutant protein.

$$\frac{340 \; nm R/B}{600 \; nm R/B} = \frac{\text{Ratio of activity} \; \frac{\text{Reaction}}{\text{Background}}}{\text{Ratio of biomass} \; \frac{\text{Reaction}}{\text{Background}}} \quad \text{Equation 1}$$

B. Methods of Characterizing Amine Dehydrogenase Activity

The activity of the AmDH can be characterized using assays that measure, for example, deamination, amination, substrate selectivity, conversion of the substrate to product, enantioselectivity, thermostability, or combinations thereof. Methods for determining such characteristics are known in the art, and exemplary methods are provided in the Examples below.

1. Amination and Deamination

Amination and deamination activity and substrate specificity can be tested over a range of concentrations for different ketones and amines. For example, MIBK and 1,3-DMBA can be used to determine $k_{cat}$ and $K_M$ of the amination and deamination reactions, respectively.

2. Conversion

Initial rate kinetic measurements are used primarily in the determination of kinetic parameters to avoid second-order effects and product inhibition. The enzyme's ability to reach complete substrate conversion cannot be determined from these initial rate experiments, but can instead be evaluated by chiral GC of conversion with a GDH recycle system. The GDH regenerates the expensive NADH by redox reaction of NAD+ and inexpensive glucose (FIG. 1). For example, in 1.5 mL reactions, replicates containing substrate (for example, 10 mM MIBK or 20 mM PFPA) can be mixed with an excess of glucose (i.e., 12 mM), GDH (i.e., 10 U), and a catalytic amount of NADH (200 µM); mixed with AmDH and allowed to react, for example, for 1, 2, 3, 4, 5, 6, 7, 8, 9, 10, 11, 12, 13, 14, 15, 16, 17, 18, 24, 36, 48 or more hours. In some embodiments, the reaction is treated with addition AmDH and allowed to react for an additional 1, 2, 3, 4, 5, 6, 7, 8, 9, 10, 11, 12, 13, 14, 15, 16, 17, 18, 24, 36, 48 or more hours. The replicates can then be compared against a calibration curve derived by the same procedure with simulated levels of conversion to determine the rate of conversion.

The product amine can also be identified through $^1$H NMR.

3. Enantioselectivity

The enantioselectivity can be estimated for the disclosed AmDH. For example, enantioselectivity can be estimated by measuring the deamination activity toward individual enantiomers of methylbenzylamine (MBA).

Derivatization with trifluoroacetic anhydride (TFAA) and chiral gas chromatography can also be used to separate and quantify individual enantiomers (Supelco, Sigma-Aldrich: Bellefonte, Pa., (1997)).

Enantiomers can also be identified by optical rotation.

4. Thermostability

The thermostability of AmDH can be compared to the scaffold amino acid dehydrogenase, for example, by circular dichroism. Each protein can be analyzed over a range of temperatures, for example from 25° C. to 95° C., to determine melting temperature and characterize stability. In some embodiments, the AmDH is analyzed using a temperature verse activity assay such as those described in the Examples below.

IV. Methods of Using Recombinant Amine Dehydrogenases

Compositions including AmDHs and methods of use thereof are also disclosed. Asymmetric synthesis by amine dehydrogenases (AmDHs) is a preferred method of making chiral amines. Chiral amines have found widespread application in asymmetric synthesis serving, for instance, as chiral bases in enantioselective deprotonation reactions or being valuable substances for resolving racemic mixtures of acids. Additionally, chiral amines are prevalent, important parts of many drugs and drug candidates. For example, chiral amines are utilized when designing alkaloids, and are preferred for drug development because they hold greater diversification potential verses secondary or tertiary chiral amine building blocks.

Generally, methods of making chiral amines include reacting or contacting a suitable substrate with an effective amount of AmDH or a fragment thereof in combination with a cofactor such as NADH to produce a chiral amine. The reaction is typically carried out in a reaction mixture, which typically includes a suitable buffer.

In some embodiments, the buffer contains $NH_4COO$ (ammonium formate) in a range from about 200 mM to about 5 M. The buffer can have a pH range from between about 9.5 and about 10.0. For example the pH can be 9.6. Suitable salts include, but are not limited to, NaCl, $NH_4Cl$, $(NH_4)_2SO_4$, and $NH_4CH_3COO$.

An exemplary buffer is a $NH_4Cl/NH_4OH$ buffer, for example, 225 mM $NH_4Cl/NH_4OH$ buffer at pH 9.6.

The aqueous phase containing the enzyme and cofactor can contact an organic phase of a solvent or solvent mixture with limited miscibility with water, which contains part of the ketone substrate. Examples of suitable organic solvents can contain hydrocarbons, such as heptane, hexane, or octane, ethers, such as methyl-tert.-butyl ether (MTBE), diisopropylether (DIPE), di-n-butylether, esters, such as ethyl acetate, butyl acetate, isoamyl acetate, or isopropyl acetate, and (hetero)aromatics, such as toluene.

Once the compound having a chiral amine is produced, it can be isolated, concentrated, or reacted with at least a second reagent to produce a desired enantiomeric product.

Compositions and methods for attaching an AmDH on a solid support through adsorption, electrostatic interactions, covalent bonding, or entrapment are also disclosed. Such a solid support can be employed as a single bead or in a packed-bed reactor.

In some embodiments, the AmDH in a gel, such as those created with aqueous buffer, hydrocarbon, and surfactant molecules, such as alkyl-ethoxyalcohols of structure $(C_nH_{2n+1})_m(EO)_p$—OH, where m, n, and p each are greater than or equal to 2. Such gels are useful for preserving activity and stability, allowing use in liquid media, and in uses requiring applications of the enzyme-gel system in a layer, such as in coating or personal care applications.

Another embodiment provides a method for using AmDH as a biosensor for NADH-specific events in unknown probes, such as aqueous solutions, tissues, or fermentation samples.

A. Cofactor Recycling

When paired with a cofactor recycling system, such as glucose/glucose dehydrogenase (GDH) or formate/formate dehydrogenase (FDH), amine dehydrogenases, such as those disclosed herein, allow for the direct production of chiral amines, with the consumption of only an inexpensive reducing agent, such as glucose or formate, and free ammonia (FIG. 1) (Vaquez-Figueroa, *Chembiochem*, 8, (18): 2295-2301 (2007); Ma, et al., *Green Chemistry*, 12, (1): 81-86 (2010); Popov, et al., *The Biochemical Journal*, 301 (Pt 3): 625-643 (1994); Van Der Donk, et al., *Current Opinion in Biotechnology*, 14, (4): 421-426 (2003)). The regeneration of the cofactor significantly reduces the substrate cost by requiring only catalytic amounts of the expensive cofactor, instead of large stoichiometric quantities. The Examples below illustrate that glucose dehydrogenase (GDH) can be used to regenerate NADH. Accordingly, in some embodiments, the AmDH are used in combination with a glucose dehydrogenase for synthesizing chiral amines.

A second cofactor recycle system is formate dehydrogenase (FDH). FDH allows for the same regeneration of cofactor, and simultaneously allow for improved atom economy relative to GDH. Instead of supplying the additional glucose substrate for the GDH system, the formate dehydrogenase could rely on formate present in an ammonium formate buffer system. Formate dehydrogenases offer the additional advantage of having specific activities more closely to that of the AmDHs, approximately 10 U mg$^{-1}$ simplifying the use of co-expression (Slusarczyk, et al., *European Journal of Biochemistry*, 267, (5): 1280-1289 (2000)).

B. Methods of Making Chiral Amines

The AmDH disclosed herein can be used in enzymatic reactions, including industrial scale enzymatic reactions, to produce chiral amines. Methods of using enzymes, such as AmDH, to produce chiral amines are known in the art. Two exemplary enzymatic schemes include i) whole-cell catalysis containing a suitable co-expression system capable of cofactor recycle, and ii) an enzyme membrane reactor capable of continuous production of chiral amine and co-factor recycle.

1. Whole Cell Catalysis

With nearly equivalent specific activities, the AmDH (1-10 U mg$^{-1}$) and formate dehydrogenase (FDH), such as formate dehydrogenase from *Candida boidinii* (6 U mg$^{-1}$), can be expressed on separate plasmids, or a dual gene plasmid, such as pETduet-1 (Merck Millipore, Billerica, Mass.) in expression competent cells such as *E. coli* BL21 (DE3). The resulting co-expression should give similar specific activities per gram of soluble protein allowing for successful catalysis. A two plasmid system is preferred for AmDH with high specific activity.

This approach was applied to the whole-cell asymmetric reductive amination of α-keto acids which represents a useful methodology for the synthesis of α-amino acid L-leucine (Bommarius, Wiley-VCH. p. 1047-1063 (2002)). LeuDH from *B. cereus* was chosen for the reductive amination and FDH from *C. boidinii* for the cofactor regeneration. The main challenge for successful co-expression of this system was the large discrepancy of specific activity between the two enzymes; ~400 U/mg for LeuDH and only 6 U/mg for FDH. This obstacle was overcome by creating a co-expression system based on the same inducible promoter, but locating the genes on two *E. coli* plasmids with different copy numbers. To compensate for its low activity, FDH was expressed in plasmid pAM3-25 which has a higher copy number. Conversely, LeuDH was expressed in plasmid pAM10-1, a medium copy number plasmid (Menzel, et al., *Eng. Life Sci.*, 4:573-576 (2004)). The two plasmids were transformed into BW3110, an *E. coli* strain suitable for high-density fermentation (Wilms, et al., *Biotechnology and Bioengineering*, 73, (2): 95-103 (2001)). The resulting combination gave similar specific activities per gram of soluble protein and in specific cases achieved nearly 100% conversion to L-leucine. Similar strategies can be applied can be used in a co-expression system utilizing the disclosed AmDH and a cofactor such as GDH or FDH.

2. Enzyme Membrane Reactor

An alternative option to whole-cell catalysis is an enzyme membrane reactor (EMR); which have been successful in the industrial application of enzymatic processes. In these systems, enzymes do not require simultaneous expression and instead can be combined at the appropriate ratio within the reactor. EMR reactors do however require purification of the desired enzymes, which can be achieved through various purification techniques known in the art (Bommarius, et al., Wiley-VCH Verlag GmbH & Co., (2004)). This system would utilize the same AmDH and FDH enzymes as the whole-cell system discussed above. Each enzyme is independently expressed and loaded to the reactor to yield similar specific activities per gram of protein. Reaction conditions such as flow rate, temperature, substrate concentration, and enzyme loading are optimized to increase conversion. Enzymes can easily be contained within the reactor by restriction of the membrane pore size. To keep the cofactor from penetrating the membrane, it may be enlarged with polyethylene glycol (PEG) (Wolfgang, et al., *Biotechnology and Bioengineering*, 32, (2): 130-139 (1988)). Otherwise, it can simply be recharged along with substrate. Lastly, this finalized reaction process would be used to isolate the reaction product (~10 g) for analysis of chemical and enantiomeric purity.

3. Organic Co-Solvent Systems

Enzymatic synthesis in non-aqueous media is a suitable alternative to traditional chemical synthesis. Many target active pharmaceutical intermediates, such as tetralones or diketones (i.e., 1-phenyl-1,2-propanedione, alpha-tetralone, beta-tetralone, etc.), have limited solubility in aqueous media. An organic cosolvent can be used increase the solubility of these substrates. Solvent selection is important and can greatly impact the hazard, environmental-friendliness, and cost of synthesis. Preferably, the organic solvent would comply with ACS GCI Pharmaceutical Roundtable Solvent Selection Guide to maintain the green benefits of an enzymatic reaction. Amino acid dehydrogenases have been studied in organic solvents (Cainelli, et al., *Organic & Biomo-* lecular Chemistry, 3, (24): 4316-4320 (2005)). It is believed that strategies developed for co-solvent system utilizing amino acid dehydrogenases can also be utilized with the AmDH disclosed herein (see Example 5 below).

Therefore, in some embodiments, the AmDH is stable in a solution including an organic solvent. Stable refers to retaining amine dehydrogenase activity in the presence of organic solvents. Representative organic solvents include, but are not limited to acetone, acetonitrile, HEPES, triethanolamine, dioxane, and tetrahydrofuran. In certain embodiments, the AmDH is stable in from about 1.0% to about 60% organic solvent or more than 10%, 20%, 30%, 40% or 50% organic solvent.

In some embodiments, an AmDH that retains amine dehydrogenase activity in solutions including about 60% organic solvent compared to the AmDH in the absence of organic solvents. In certain embodiments, the AmDH retains at least 30% amine dehydrogenase activity in the presence of about 15% organic solvent, or at least 15% activity in about 30% organic solvent, or at least about 5% activity in 40% organic solvent.

Still another embodiment provides a vector comprising a nucleic acid of encoding an AmDH operably linked to a promoter. The vector expresses the encoded polypeptide in a form that retains amine dehydrogenase activity in the presence of about 1% to about 60% organic solvent.

C. Substrates and Products a. Substrates

The AmDHs disclosed herein can be used in combination with a variety of substrates to produce chiral amines. Substrates can be selected by one of skill in the art based on the specificity and activity of the AmDH. Instead of the wild-type alpha-keto acid, the amine dehydrogenases disclosed herein accept the analogous ketone, methyl isobutyl ketone (MIBK), corresponding to removal of the carboxyl moiety in a reductive amination reaction (FIG. 1).

The Examples below illustrate the LeuDH-AmDH disclosed herein have activity toward a number of different substrates including, MBA, cyclohexylamine, cylcohexanone, ethyl pyruvate, methyl aceto acetate, ethyl-3-oxohexanoate, and acetophenone.

The Examples below also illustrate that the PheDH-AmDH disclosed herein typically have increased specific activity and broader substrate scope than the LeuDH-AmDH counterparts. The substrate scope of Phe-DH-AmDH include amination of diverse ketones, including aromatic ketones. The ranges of ketone substrates varies in structure from small aliphatic ketones such as 3-methyl-2-butanone, to larger aromatic ketones with additional functionality, such as phenoxy-2-propanone.

The Examples below illustrate that a preferred PheDH-AmDH, K77S/N276L, exhibits elevated activity toward methylketones versus ethylketones or cyclic ketones. The top five most active ketones; PFPA, phenoxy-2-propanone, 2-hexanone, methyl isobutyl ketone and 3-methyl-2-butanone are all methyl-ketones. This specificity is also observed in the large differences in activity toward 2-hexanone (155.7 mU/mg) versus 3-hexanone (1.6 mU/mg): despite their structural similarities, the methylketone 2-hexanone exhibited approximately 100-fold higher activity. 1,3 Phenylbutanedione exhibits an activity level of 30 mU/mg.

b. Products

AmDH can be used in the synthesis of a number of compounds. In preferred embodiments, the AmDH is used to prepare amine-based compounds, such as amine-based pharmaceutical drugs. Exemplary pharmaceutical drugs have chiral amine moieties. Exemplary drugs include, but are not limited to, codeine (3-methylmorphine), ZOLOFT® (sertraline), PRANDIN® (repaglinide), methadone, FLOMAX® (tamsulosin), JANUVIA® (sitagliptin), TAMIFLU® (oseltamivir phosphate), sibutramine, cinacalcet, EXELON® (rivastigmine), lariam, ethambutol, and lopinavir.

EXAMPLES

Example 1

Preparation of Leucine dehydrogenase Variants with Amine Dehydrogenase Activity

Materials and Methods gDNA Preparation, Gene Isolation and Overexpression

Leucine dehydrogenase (E.C. 1.4.1.9) from *Bacillus stearothermophilus* was donated by Assistant Professor Bert C. Lampson from East Tennessee State University, followed by isolation of the genomic DNA through application of method B described by Mehling et al. (Mehling, et al., *FEMS Microbiology Letters*, 128, (2): 119-125 (1995)). The isolated gene (1104 bp) was inserted into pET17b vector (Life Technologies-Invitrogen, Grand Island, N.Y., USA) at the restriction sites NdeI and HindIII (New England Biolabs) using T4 DNA Ligase (Roche, South San Francisco, Calif., USA) at 16° C., 8 hours. This allowed for overexpression upon transformation into *E. coli* BL21 DE3 competent cells (Life Technologies). Cultures were expressed at 37° C. in LB media for 24 hours. Cultures were induced with IPTG at and $OD_{600}$ between 0.4 and 0.6 absorbance. Overexpression was evident by SDS-PAGE identifying a high protein concentration at 40.5 kDa.

Protein Purification

For purification, proteins were expressed in pET28a vector (Life Technologies) in BL21 (DE3) with an N-terminal Histag. The gene was inserted in the vector at restriction sites NdeI and HindIII. His-tagged proteins were expressed in a similar manor as (Section 3.2.1) at 37° C. for 24 hours. His-tagged proteins were subsequently purified using immobilized metal ion affinity chromatography (IMAC) with a Ni-NTA resin (Thermo Scientific, Rockford, Ill., USA). Cell culture pellets were made by centrifugation (4000 rpm, 30 min, 4° C.) in 50 mL aliquots. Cell pellets were resuspended in 50 mM phosphate buffer (6 mL) at pH 8.0 containing 20 mM imidazole and 300 mM NaCl. This was followed by sonication and centrifugation to remove cell debris. The clarified cell lysate was bound to the Ni-NTA resin by shaking on ice for 1 hour, and subsequently purified by column affinity chromatography. Protein-bound resin and clarified cell extract was poured over a column, and washed twice with 50 mm phosphate buffer (5 mL) at pH 8.0 containing 50 mM imidazole and 300 mM NaCl. Purified protein was eluted with the same buffer solution containing 250 mM imidazole (2 mL). An SDS-PAGE gel of a representative purification can be seen below. The leucine dehydrogenase protein can be seen at 42.5 kDa with his-tag attached.

Spectrophotometric Assay

Activity of purified proteins was measured using a spectrophotometric assay at 340 nm, corresponding to the cofactor nicotinamide adenine dinucleotide (NADH, $\epsilon_{340}$=6220 $M^{-1}$ $cm^{-1}$) (Dawson, et al., Clarendon Press, (1989). For reductive amination, reactions took place in 500 mM $NH_4Cl/NH_4OH$ at pH 9.6, with 200 µM NADH and 20 mM of the ketone substrate, unless otherwise specified. For oxidative deamination, reactions took place in 0.1 M $NaHCO_3/Na_2CO_3$ buffer at pH 10.0, with 1 mM NAD+ with 10 mM of the amine substrate of interest. All reactions were performed at 25° C.

unless otherwise specified. Enzyme was added in 10 μL aliquots in dilute concentrations. Enzyme concentrations varied upon activity levels with the substrate present, but were dilute enough to ensure linear conversion kinetics over the analytical time period (10 min to 30 min). Specific activities were then calculated from the stoichiometric conversion of cofactor as determine by the change in absorbance at 340 nm over time.

Mutagenesis and Library Generation

Mutant libraries were generated using overlap extension PCR. After identification of mutational sites, primers were designed according to the guidelines of the QUIKCHANGE® Site Directed Mutagenesis Protocol (Agilent Technologies, Santa Clara, Calif., USA). These primers were then used in the overlap extension protocol described in Molecular Cloning: A Laboratory Manual. The overlap extension method has several advantages. It requires the successive amplification of DNA segments, making it easier to troubleshoot than the blind success or failure of the QUIKCHANGE® protocol. Additionally, the overlap extension method does not potentially carry over whole plasmid from the parent DNA into the final transformation. This significantly decreases the amount of non-mutated colonies present in the screened library. After mutation, the resulting mutated gene was digested using NdeI and HindIII, ligated into pET17b, and expressed as described below. A listing of the primers used in amplification of each library is provided in Table 3.

Figure 3:
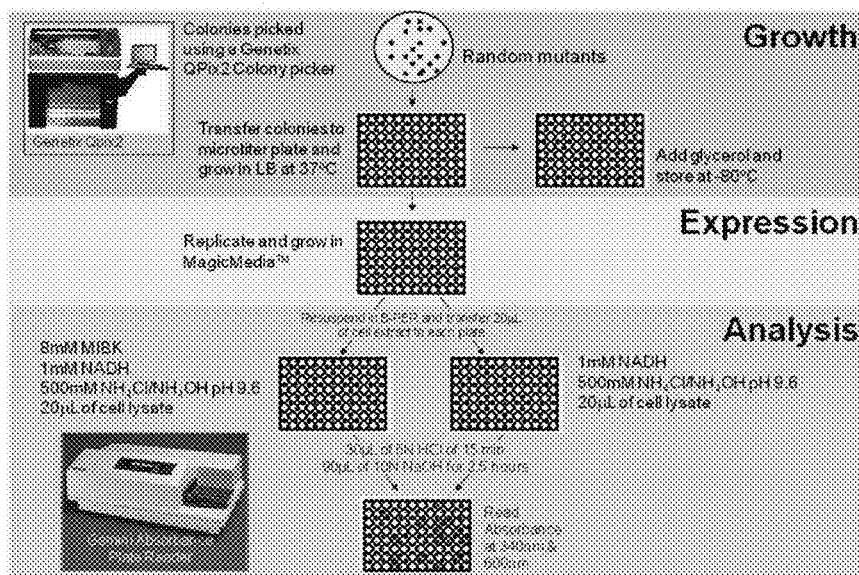
FIG. 3 is a diagram showing a NAD+ auto-fluorescence assay used for screening libraries 2 through 5 for active LeuDH-AmDH mutants.

The randomized libraries were plated on Genetix 10"×10" in. agar plates (Molecular Devices, Sunnyvale, Calif., USA) containing 200 mL of LB-agar with 50 μg/mL ampicillin, and allow to grow for 18-24 hours at 37° C. The resulting colonies were autonomously picked using a Genetix QPix2 Colony Picker (Molecular Devices), and inoculated in 96-well microtiter plates containing 200 μL of LB media with 50 μg/mL ampicillin (LB-AMP). The plates were covered in Parafilm M (Bremis, Neenah, Wis., USA) to prevent cross contamination between wells, and incubated at 37° C., 200 rpm for 24 hours. The plates were then replicated into expression plates containing 250 μL of auto-inducing MAGICMEDIA™ (Life Technologies) containing 50 μg/mL ampicillin. Glycerol (100 μL) was added to the LB-AMP 'master' plate, and stored at −80° C. for later sequence resurrection and identification. The expression plates were covered with Parafilm M and incubated at 37° C. for 24 hours, resulting in the overexpression of protein variants (FIG. 3.5). The expression plates were centrifuged (1,000 rpm, 30 min, 4° C.), decanted, and stored at −80° C. until screened.

TABLE 3

Table of forward (Fwd) and reverse (Rev) primers used in the generation of LeuDH mutant libraries.

| Library | Primer | | |
|---|---|---|---|
| 3 | Fwd | 5'AGGGCTGAACGGCCGCTACATTACGGBGNNTRABRTKGGCACGACCGTTGCCGATATGGA 3' | (SEQ ID NO: 29) |
|   | Rev | 5'ATCCATATCGGCAACGGTCGTGCCMAYVTYANNCVCCGTAATGTAGCGGCCGTTCAGCCCT 3' | (SEQ ID NO: 30) |
| 4 | Fwd | 5'ATTCATGACACGACGCTCGGCCCGGCGDBWGBCDBWACGCGCATGTGGATGTACAATTC 3' | (SEQ ID NO: 31) |
|   | Rev | 5'GAATTGTACATCCACATGCGCGTWVHGVCWVHCGCCGGGCCGAGCGTCGTGTCATGAAT 3' | (SEQ ID NO: 32) |
| 5 | Fwd | 5'GATTATGTGATCAACNNKGGCGGCGTCATCAACG 3' | (SEQ ID NO: 33) |
|   | Rev | 5'CGTTGATGACGCCGCCMNNGTTGATCACATAATC 3' | (SEQ ID NO: 34) |
| 6 | Fwd | 5'CAACGCCGGCGGCDBSATCAACDBSGCCGATGAGCTGTACGGC 3' | (SEQ ID NO: 35) |
|   | Rev | 5'GCCGTACAGCTCATCGGCSVHGTTGATSVHGCCGCCGGCGTTG 3' | (SEQ ID NO: 36) |
| 7 | Fwd | 5'CTGAACGGCCGCTACATTACGNNKGTTGACGTTGGCACGACCG 3' | (SEQ ID NO: 37) |
|   | Rev | 5'CGGTCGTGCCAACGTCAACMNNCGTAATGTAGCGGCCGTTCAG 3' | (SEQ ID NO: 38) |
| 8 | Fwd | 5'CGCCGGCGGCGTCNNKAACGTCGCCGATGAGCTGTA 3' | (SEQ ID NO: 39) |
|   | Rev | 5'TACAGCTCATCGGCGACGTTMNNGACGCCGCCGGCG 3' | (SEQ ID NO: 40) |
| 9 | Fwd | 5'CGTCATCAACGTCGCCGATNNKCTGTACGGCTACAACCGTGAACG 3' | (SEQ ID NO: 41) |
|   | Rev | 5'CGTTCACGGTTGTAGCCGTACAGMNNATCGGCGACGTTGATGACG 3' | (SEQ ID NO: 42) |
| 10 | Fwd | 5'CGCCGGCTCGGCGNNKAATCAGCTGAAAGAGCCGCG 3' | (SEQ ID NO: 43) |
|   | Rev | 5'CGCGGCTCTTTCAGCTGATTMNNCGCCGAGCCGGCG 3' | (SEQ ID NO: 44) |
| 11 | Fwd | 5'CCCGCGGCATGACGTACDDKAACGCGGCCGCCG 3' | (SEQ ID NO: 45) |
|   | Rev | 5'CGGCGGCCGCGTTMHHGTACGTCATGCCGCGGG 3' | (SEQ ID NO: 46) |
|   | Fwd | 5'CGCCGGCTCGGCGDDKAATCAGCTGAAAGAGCCGCG 3' | (SEQ ID NO: 47) |
|   | Rev | 5'CGCGGCTCTTTCAGCTGATTMHHCGCCGAGCCGGCG 3' | (SEQ ID NO: 48) |

Results

Previously characterized amine dehydrogenases were incapable of effecting the reductive amination of ketones and lacked stereoselectivity (Itoh, et al., *Journal of Molecular Catalysis B: Enzymatic*, 10, (13): 281-290 (2000)). Therefore, as discussed in more detail below, beginning with an existing amino acid dehydrogenase scaffold, the substrate specificity of the enzyme was altered through several rounds of protein engineering to create an amine dehydrogenase. Instead of the wild-type α-keto acid, the amine dehydrogenase now accepts the analogous ketone, methyl isobutyl ketone (MIBK), which corresponds to replacement of the carboxyl moiety with a methyl group (FIG. 2).

Leucine dehydrogenase from *Bacillus stereothermophilus* served as the initial protein scaffold. The wild-type leucine dehydrogenase exhibited no measurable activity toward the reductive amination of MIBK.

Residue Lys67 of LeuDH directly interacts with the carbonyl moiety of the amino acid substrate through favorable charge interactions, and was chosen as the initial point of mutation (Brunhuber, et al., *Biochemistry*, 39, (31): 9174-9187 (2000); Sekimoto, et al., *Journal of Biological Chemistry*, 268, (36): 27039-27045 (1993)). Library 1 included mutation to each of the remaining 19 amino acids. The resulting variants were cloned into pET28a vector and BL21 (DE3) competent cells for subsequent expression and His-tag purification. Each purified variant was analyzed spectrophotometrically at 340 nm to correlate the NADH/NAD+ cofactor conversion with the amination and deamination activity (93).

TABLE 4

Grouping of active-site residues in *B. stearothermophilus* LeuDH.

| Library | PheDH | LeuDH with degenerate codons | Library screening size[a] |
|---|---|---|---|
| 1 | K66 | K67[b] | 20 |
| 2 | M63 | M64 NNK | 3066 |
|  | K66 | K67 NNK |  |
| 3 | G116 | A112 GBC | 3450 |
|  | P117 | E113 NNT |  |
|  | D118 | D114 RAB |  |
|  | V119 | V115 RTK |  |
| 4 | A38 | L39 DBW | 2910 |
|  | G39 | G40 GBC |  |
|  | G40 | G41 DBW |  |
| 5 | S189 | H187 NNK | 94 |
| 6 | A292 | V290 DBS | 969 |
|  | L295 | V293 DBS |  |
| 7 | G116 | A112 NNK | 94 |
| 8 | I293 | I291 NNK | 94 |
| 9 | E299 | E296 NNK | 94 |
| 10 | N263 | N261 NNK | 94 |
| 11 | K66 | K67 DDK | 969 |
|  | N263 | N261 DDK |  |

[a]Required screening for 95% statistical coverage of library sequence space.
[b]Analyzed as individual mutants using purified protein The remaining binding pocket residues were broken into groups on the basis of CASTing principles to create libraries 2, 3, 4, and 6 (Table 4) (Reetz, et al., *Angewandte Chemie-International Edition*, 44, (27): 4192-4196 (2005)). Regions of the binding pocket were grouped based upon their primary structure. The breadth of mutation at each position was then narrowed by their interactions based upon secondary structure. For example, every other amino acid side chain interacts with one another in a β-sheet, while only every fourth amino acid of an α-helix does the same. Interacting residues within each group were mutated simultaneously to capture any synergistic effects with neighboring residues. The mutational breadth at each position was constrained through degenerate codons to avoid amino acid substitutions which were likely detrimental to substrate binding (such as clear steric hindrance or unfavorable charge interactions). Removing a subset of detrimental amino acids limits the library size, so as to improve screening efficiency, while maintaining an increased chance of altering the substrate specificity. The number of colonies required to achieve 95% statistical coverage was calculated using Equation 2.

$$N = \frac{\ln(1 - P)}{\ln\left(1 - \frac{1}{n}\right)}; \quad \text{Equation 2}$$

$N$ = number of colonies required in screening, $P$ = statistical percent of coverage of library, $\frac{1}{n}$ = proportion of the least represented codon An example set of the degenerate codons applied in library 3 demonstrates the breadth of mutation over the four residues; Ala112, Glu113, Asp114, and Val115 (Table 5). These four residues create a loop region along the binding pocket. The side chains of residues 113 and 115 face toward the binding pocket, while 112 and 114 are directed outward. Residues 113 and 115 are believed to have strong interactions in stabilizing the imine intermediate, and for this reason will be widely mutated excluding only mutations which create unfavorable charge interactions or drastic steric hindrance. Conversely, residues 113 and 115 are likely to have less interaction. These residues' mutations will be restricted to amino acids similar to the wild type residues, limiting mutational breadth to greatly reduce the required screening effort.

TABLE 5

LeuDH library 3 distribution of degenerate codon amino acids at positions 113 through 116

| Residue | A112 | E113 | D114 | V115 |
|---|---|---|---|---|
| Codon | GBG | NNT | RAB | RTK |
| Ala [A] | 1 | 1 | 0 | 0 |
| Arg [R] | 0 | 1 | 0 | 0 |
| Asn [N] | 0 | 1 | 2 | 0 |
| Asp [D] | 0 | 1 | 2 | 0 |
| Cys [C] | 0 | 1 | 0 | 0 |
| Gln [Q] | 0 | 0 | 0 | 0 |
| Glu [E] | 0 | 0 | 1 | 0 |
| Gly [G] | 1 | 1 | 0 | 0 |
| His [H] | 0 | 1 | 0 | 0 |
| Ile [I] | 0 | 1 | 0 | 1 |
| Leu [L] | 0 | 1 | 0 | 0 |
| Lys [K] | 0 | 0 | 1 | 0 |
| Met [M] | 0 | 0 | 0 | 1 |
| Phe [F] | 0 | 1 | 0 | 0 |
| Pro [P] | 0 | 1 | 0 | 0 |
| Ser [S] | 0 | 2 | 0 | 0 |
| Thr [T] | 0 | 1 | 0 | 0 |
| Trp [W] | 0 | 0 | 0 | 0 |
| Tyr [Y] | 0 | 1 | 0 | 0 |
| Val [V] | 1 | 1 | 0 | 2 |
| Stop | 0 | 0 | 0 | 0 |
| Codons | 3 | 16 | 6 | 4 |
| AA | 3 | 15 | 4 | 3 |

Single residue libraries (5, 7, 8, and 9) were broadly mutated to all 20 amino acids (codon: NNK), because of their small size and the insignificant decrease in the required screening effort by applying a more restrictive degenerate codon.

Library 10 included mutation of binding pocket residue N261. This position was not initially considered for mutation, despite its interaction with the carboxy moiety of the wild-type ligand, because of its involvement in binding the cofactor. However, as only the backbone amino group of the residue interacts with the cofactor, an exception was made for mutation at this position. The desired protein interactions with the cofactor will be mostly preserved after substitution of the side chain due to the universal peptide backbone structure. Being a single residue library, N261 was broadly mutated to all 20 amino acids (codon: NNK)

Lastly, residues K67 and N261 were mutated simultaneously to create library 11. These residues have a synergistic effect with respect to binding the wild-type substrate's carboxyl moiety, and interact directly with one another.

Example 2

Variant K67S/E113V/N261L/V290C is an Amine Dehydrogenase

Materials and Methods

Three different assays were used over the course of evaluating the mutant libraries. Each subsequent assay method improved the quality of screening over previous methods.

NAD+ Auto-Fluorescence Assay

Libraries 2-5 were screened using an NAD+ auto-fluorescence assay (84-86). In an optimal system, sensitivities as low as 0.01 μM NAD(P)+ fluorophore were observed (Seidemann, New York, N.Y. Academic Press (1973)). Expression plates containing cell culture pellets were resuspended in 50 μL of B-Per Cell Lysing agent (Thermo Scientific). The resulting cell lysate was split into 20 μL aliquots in two separate plates, one reaction plate and one background plate. For the background plate, 180 μL of 1.1 mM NADH in 500 mM $NH_4Cl/NH_4OH$ buffer pH 9.6 was added to each well. This plate lacks the ketone substrate and will only result in background conversion rates. Similarly, 180 μL of the same buffer was added to the reaction plates, containing an additional 80 mM MIBK substrate. The plates were incubated at room temperature for 2 hours to allow for conversion.

After reaction, the fluorophore was generated through a pH shift. First the residual NADH was removed by adjusting the pH to 1.0 through the addition of 30 μL, of 6N HCl and incubated for 25 minutes. At this pH value, the NADH will rapidly degrade while leaving the stable NAD+. To create the NAD+ fluorescence, the pH value was re-adjust to >13.0 by adding 80 μL, of 10 N NaOH and incubated in the dark for 2.5 hours. Fluorescence was measured using a Gemini Spectramax Microplate Spectrofluorometer (Molecular Devices, Downingtown, Pa., USA) at an excitation wavelength of 360 nm and emission wavelength of 455 nm (FIG. 3) (Tsotsou, et al., *Biosensors and Bioelectronics*, 17, (12): 119-131 (2002)).

Wells were ranked based upon the differential increase in fluorescence over the background plate. NAD+ concentrations can be distinguished as low as 1-2 μmol to above 100 mmol. This allows for the identification of very slight improvements in AmDH activity. The control experiment however, did not account for variations in expression levels between wells. This variation significantly reduced the sensitivity of the assay, and increased the identification of false positives. While the assay did yield successful mutants, its long reaction time and low signal to noise ratio were not ideal.

Formazan-Based Assay

Libraries 6 and 7 were analyzed using a formazan-based assay developed by Chen et. al. (Chen, et al., *Journal of Biotechnology*, 142, (2): 127-134 (2009)). This assay takes advantage of the elevated activity in the deamination direction, giving the assay a better signal-to-noise ratio. The reaction scheme is represented in FIG. 4. The enzymatic deamination activity is related to conversion of NAD+ cofactor to produce NADH, which is re-oxidized back to NAD+ by phenazine ethosulfate (PES, Sigma Aldrich). The resulting reduced PES subsequently reduces 2-(4-iodophenyl)-3-(4-nitrophenyl)-5-phenyltetrazolium chloride hydrate (INT, Sigma Aldrich) to create formazan. Formazan creates a deep red color which can be characterized by absorbance at 495 nm. Cell lysate was split in the same way as the previous assay. Deamination buffer (180 μL) containing 1 mM NAD+, a catalytic amount of PES, and 0.1 M glycine buffer at pH 10.0 was added to the background plate. The reaction plate buffer also contained 80 mM 1,3-DMBA substrate. Plates were allowed to incubate for 30 min at room temperature before absorbance readings.

Production of NADH in the Deamination of 1,3-DMBA Assay

Figure 5:
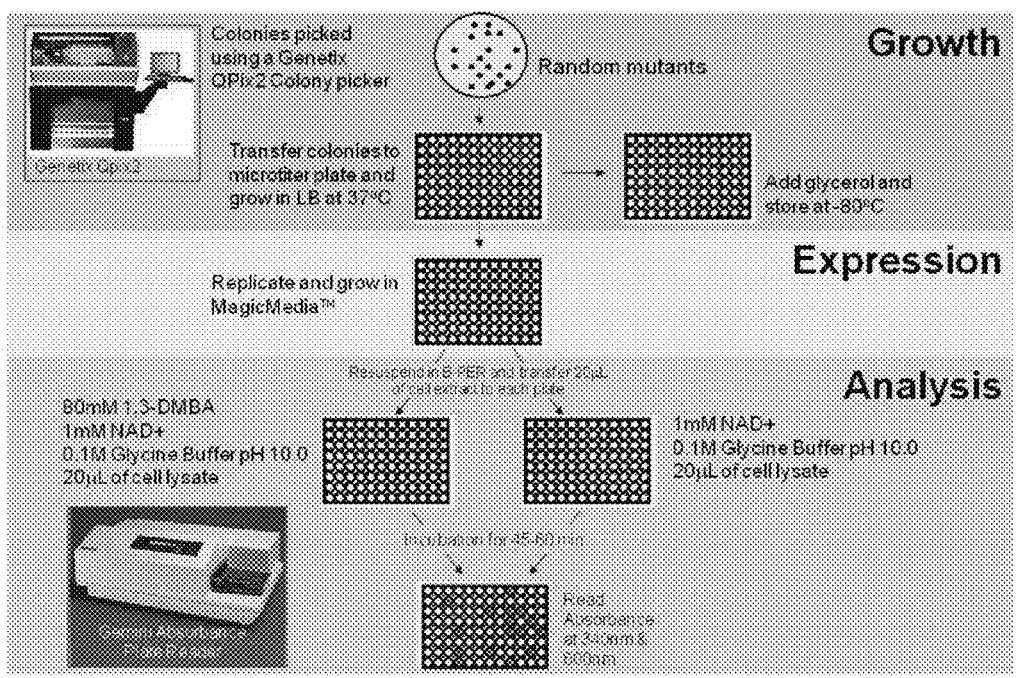
FIG. 5 is a diagram showing a 1,3-DMBA deamination assay used for screening libraries 8-11 for active LeuDH-AmDH mutants.
Figure 6:
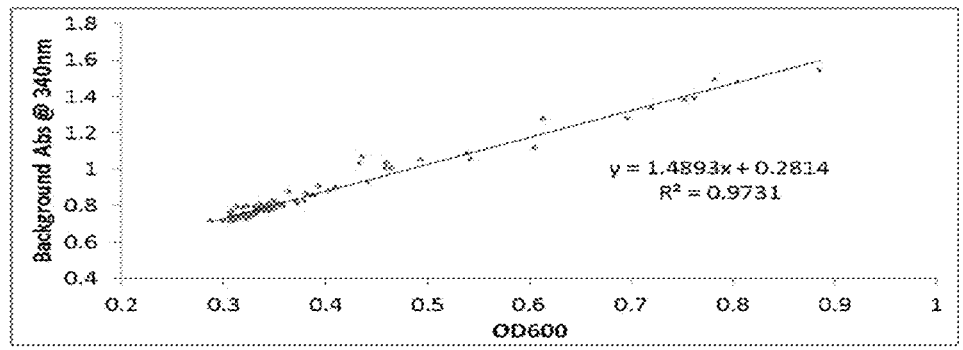
FIG. 6 is scatter plot showing correlation of LeuDH variants' OD600 absorbance to background absorbance of 340 nm in the 1,3-DMBA deamination assay depicted in FIG. 4.

The final assay (FIG. 5) was used in the analysis of libraries 8 through 11. The assay involved reading the wells' absorbences at two wavelengths, 340 nm and 600 nm. The increased absorbance at 340 nm corresponds to the production of NADH in the deamination of 1,3-DMBA, while the 600 nm reading roughly estimates the biomass present in the well. The absorbance at 600 nm correlates strongly the background absorbance at 340 nm (FIG. 6)

The absorbance at 340 nm was normalized by the 600 nm absorbance reading for both the reaction and background plates. Variants were then scored by their proportional increase over the background observed in each well (Equation 1, below). This method significantly reduces the background noise of the assay by accounting for differences in expression levels, causing more accurate determination of enzymatic activity and decreasing false positives. The resulting quantity roughly estimates the specific activity of the overexpressed mutant protein.

$$\frac{340 \text{ nm} R/B}{600 \text{ nm} R/B} = \frac{\text{Ratio of activity} \frac{\text{Reaction}}{\text{Background}}}{\text{Ratio of biomass} \frac{\text{Reaction}}{\text{Background}}} \quad \text{Equation 1}$$

Results

Library Diversity Verification and Assay Characterization

Prior to screening, each library was checked for diversity at the target residues by sequencing randomly selected colonies (10-20 colonies), and comparing their distribution to the applied degenerate codon. Table 6 gives an example of 20 randomly selected wells from library. The diversity at positions 39-41 indicates successful application of the mutagenesis protocol. Similar diversity was observed for all libraries.

The NAD+ auto-fluorescence assay (libraries 2-5) typically indicated a net negative value for non-beneficial mutations; the net relative fluorescence units (RFU) ranged from 0 to −500. Beneficial mutations gave net positive RFU, and were easily identifiable over background.

Figure 7:
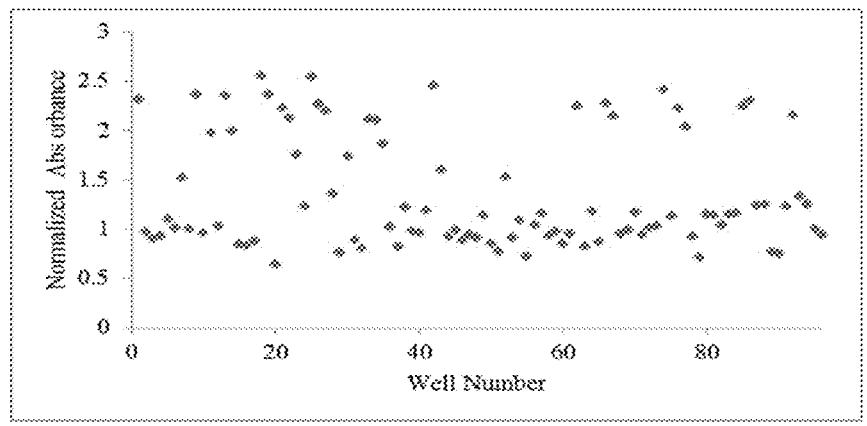
FIG. 7 is a scatter plot showing an example of a typical well plate analyzed using the high-throughput absorbance-based assay with readings at 340 nm and 600 nm (library 11, plate 9).

FIG. 7 contains an example of a typical well plate analyzed using the absorbance-based assay with readings at 340 nm and 600 nm. Normalized absorbance values were calculated using Equation 2. Unsuccessful mutants show a normalized absorbance of approximately unity indicating no enhancement over background, while the successful mutants indicated the desired catalytic activity with normalized absorbance beyond 1.5.

TABLE 6

Sequencing results of random LeuDH library 4 colonies to confirm diversity after the application of degenerate codons

| Residue | 39 | 40 | 41 |
|---|---|---|---|
| WT | Leu | Gly | Gly |
| 1 | Ala | Val | Ala |
| 2 | STP | Val | Ser |
| 3 | Phe | Ala | Ile |
| 4 | Ala | Val | Ala |
| 5 | Val | Gly | Thr |
| 6 | Ala | Val | Ser |
| 7 | Arg | Ala | Ser |
| 8 | Val | Gly | Thr |
| 9 | Cys | Gly | Thr |
| 10 | Arg | Val | Ser |
| 11 | Thr | Gly | Ile |
| 12 | Thr | Val | Val |
| 13 | Cys | Val | Ile |
| 14 | Val | Gly | Ser |
| 15 | Ala | Arg | Thr |
| 16 | Thr | Leu | Ser |
| 17 | Ile | Gly | STP |
| 18 | Gly | Gly | Phe |
| 19 | Val | Ala | Val |
| 20 | Ala | Gly | Ser |

Identification of Active Mutants

The individual analysis of library 1 variants yielded a single beneficial mutation, Lys67Met that exhibited low, yet unprecedented activity for reductive amination (0.2 mU mg$^{-1}$). A higher activity of 3.4 mU mg$^{-1}$ was observed in the oxidative deamination of racemic 1,3-dimethyl butyl amine (1,3-DMBA). This mutation was carried over into the subsequent libraries.

The top performers of each high-throughput library (libraries 2-11) were sent for sequencing. The resulting sequences resulted in either the identification of beneficial mutations, or a large presence of parental variants. When beneficial mutations were identified, they often appeared multiple times in the sequenced hits. (Table 7) The assay accurately and repeatedly identified beneficial mutations. When all or mostly parental variants were identified as the best performing mutants, these libraries failed to identify further mutations. The enrichment of parental variants from a random library further supports the accuracy and robustness of the successful high-throughput screen. To get a more detailed determination of activity, each hit was further evaluated as purified protein. The hits were expressed and purified as described in the materials and methods. The purified protein's activity was measured over a range of MIBK and 1,3-DMBA concentrations to determine $k_{cat}$ and $K_M$ of the amination and deamination reactions, respectively. An example of these results can be seen in Table 7 for the analysis of library 11.

TABLE 8

LeuDH library 3 hit sequencing. These sequences represent the top 10 performing colonies as indicated by the high-throughput assay. Repeat identifications of beneficial mutations are grouped at the top of the table. The top variants also returned the wild type sequence (italics).

| Residue | | | |
|---|---|---|---|
| A112 | E113 | D114 | V115 |
| Ala | Val | Asp | Val |
| Ala | Val | Asp | Val |
| Ala | Val | Asp | Val |
| Ala | Leu | Asp | Val |
| Ala | Leu | Asp | Val |
| Val | Ala | Asp | Met |
| Gly | Phe | Asn | Ile |
| Ala | Phe | Asn | Val |
| *Ala* | *Glu* | *Asp* | *Val* |
| Ala | Cys | Asp | Val |

TABLE 8

Characterization of LeuDH library 11 hits and comparison to previous best preforming variants from library 10 (n.m. = not measurable (<0.1 mU mg$^{-1}$).

| | Residue | | Amination of MIBK | | Deamination of 1,3-DMBA | |
|---|---|---|---|---|---|---|
| Well | K67 | N261 | $V_{max}$ | $K_M$ | $V_{max}$ | $K_M$ |
| | | | Previous Top Variants | | | |
| Lib10 B2 | Met | Cys | 0.236 ± 0.04 | 21.6 ± 11.5 | 1.76 ± 0.20 | 14.8 ± 6.1 |
| Lib10 H3 | Met | Val | 0.084 ± 0.01 | 21.01 ± 8.5 | 2.894 ± 0.44 | 33.1 ± 13.0 |
| | | | Library 11 Hits | | | |
| 2B1 | Ser | Leu | 0.331 ± 0.07 | 18.7 ± 11.7 | 2.350 ± 0.26 | 41.9 ± 9.7 |
| 1C9 | Ser | Met | 0.326 ± 0.02 | 61.1 ± 6.2 | 1.381 ± 0.17 | 28.3 ± 8.3 |
| 1H4 | Val | Met | 0.240 ± 0.04 | 37.6 ± 14.4 | 4.841 ± 3.44 | 251.7 ± 224 |
| 2B11 | Gly | Leu | 0.211 ± 0.07 | 37.7 ± 27.2 | 1.710 ± 0.17 | 111.4 ± 17.7 |
| 1G2 | Leu | Leu | 0.159 ± 0.04 | 27.2 ± 19.0 | 6.688 ± 18 | 498.0 ± 1551 |
| 1A2 | Leu | Val | 0.022 ± 0.00 | 16.7 ± 8.0 | 0.976 | 33.8 |
| 2E12 | Gly | Gly | 2.4E+09 | 3.8E+13 | n.m. | n.m. |
| 2G8 | Gly | Cys | 7.2E+15 | 8.2E+18 | 5.1E+11 | 7.0E+13 |

After the screening of 11 libraries, four beneficial mutations were identified. Early rounds of mutation (libraries 1-9) identified either the wild-type sequence or single variants which improved the activity simultaneously in both the amination and deamination directions, thus allowing for the straightforward selection of the top variant. Library 10 identified distinct mutations for the most-active amination and deamination variants (Table 9). The most active amination and deamination mutations were with position Asn261 exchanged by Cys and Val, respectively. Library 11 further improved the amination activity by identifying synergistic mutations at positions 67 and 261, with these positions mutated from those identified in libraries 1 and 10. Libraries 2, 4, 5, and 7-9 were unsuccessful in identifying beneficial mutations, returning the parental sequence as hits. The final amine dehydrogenase contained four mutations, which are summarized in Table 9.

TABLE 9

Accumulated mutations and resulting improvements to the specific activity and $K_M$ of LeuDH. Error values represent 95% confidence intervals of nonlinear fit parameters.

| Library | Mutations | Reductive amination specific activity[a] | $K_M$[b] | | Oxidative deamination specific activity[a] | $K_M$[b] | |
|---|---|---|---|---|---|---|---|
| WT | — | n.m.[c] | n.m. | | n.m. | n.m. | |
| 1 | K67M | 0.0002 | n.m. | | 0.0034 | n.m. | |
| 3 | K67M, E113V | 0.015 | n.m. | | 0.65 | 48 | |
| 6 | K67M, E113V, V290C | 0.016 ±0.004 | 70.2 | ±35 | 1.02 ±0.41 | 77.1 | ±66 |
| 10[d] | K67M, E113V, N261V, V290C | 0.089 ±0.007 | 10.3 | ±3.6 | 2.81 ±0.44 | 30.9 | ±13 |
| | K67M, E113V, N261C, V290C | 0.236 ±0.04 | 21.6 | ±12 | 1.76 ±0.20 | 14.8 | ±6.0 |
| 11 | K67S, E113V, N261L, V290C | 0.690 ±0.07 | 15.1 | ±5.1 | 2.64 ±0.28 | 57.5 | ±12.5 |

[a]Maximum specific activity (U mg$^{-1}$ protein).
[b]MIBK or 1,3-DMBA substrate (mM).
[c]n.m. = not measurable (<0.1 mU mg$^{-1}$).
[d]Separate variants gave maximum amination and deamination activity.

Figure 8:
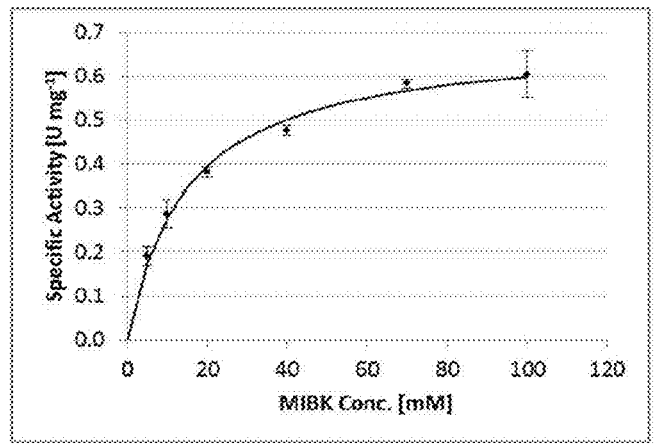
FIG. 8 is best fit curve showing non-linear Michaelis-Menten fit of MIBK amination activity by LeuDH-AmDH quadruple variant K67S/E113V/N261L/V290C.

The resulting quadruple variant (K67S/E113V/N261L/V290C) gave the highest amination activity of 0.69 U mg$^{-1}$ with a corresponding $k_{cat}$ value of 0.46 s$^{-1}$, as determined by a non-linear fit (FIG. 8) of the Michaelis-Menten equation (Equation 3) using MATLAB.

$$v = \frac{d[P]}{dt} = \frac{V_{max}[S]}{K_M + [S]};\qquad \text{Equation 3}$$

v=reaction rate,
[P]=product concentration,
[S]=substrate concentration,
$V_{max}$=maximum rate under saturated conditions
Characterization of Variant K67S/E113V/N261L/V290C The most-active variants showed amination and deamination activity toward a number of ketones and amines, respectively (Table 10). Since MIBK most closely mimics the wild-type keto-acid, 3-oxo-2-pentanoate, it was not surprisingly the most activity of the ketones tested. The detailed measurements of the final variant (K67S/E113V/N261L/V290C) kinetics showed enhanced amination activity over the previous library 10 mutant toward all the ketones investigated, except methyl acetoacetate.

TABLE 10

Substrate profile of top amination and deamination variants.

| Substrate[a] | K67M/E113V/N261V/N290C[b] | | K67S/E113V/N261L/V290C[b] | |
|---|---|---|---|---|
| (R)-MBA | 476.5 | ±1.4 | 586.3 | ±4.1 |
| (S)-MBA | 5.0 | ±0.0 | 1.6 | ±0.0 |
| (R/S)-MBA[c] | 484.0 | ±3.5 | 784.6 | ±13.4 |
| cyclohexylamine | — | | 56.0 | ±0.0 |
| cyclohexanone | 18.8 | ±0.0 | 123.4 | ±3.5 |
| ethyl pyruvate | 19.8 | ±7.0 | 13.2 | ±5.8 |
| methyl acetoacetate | 4.5 | ±0.7 | 4.5 | ±0.6 |
| ethyl-3-oxohexanoate | 6.4 | ±4.9 | 14.0 | ±1.2 |
| acetophenone | 3.5 | ±0.7 | 58.8 | ±1.7 |

[a]Activity measured with 20 mM substrate.
[b]Specific activity in mU mg$^{-1}$ protein, with the error representing one standard deviation.
[c]Activity measured with 40 mM racemic methyl benzyl amine (MBA), 20 mM of each enantiomer.

Conversion and GDH Cofactor Recycle System

Figure 9:
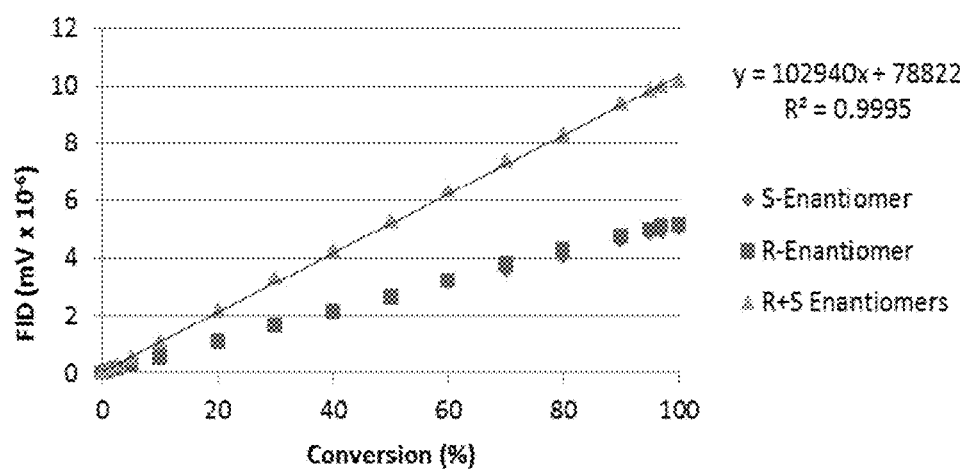
FIG. 9 is a scatter plot showing the conversion calibration curve of MIBK to 1,3-DMBA by LeuDH-AmDH quadruple variant K67S/E113V/N261L/V290C.

Initial rate kinetic measurements are used primarily in the determination of kinetic parameters to avoid second-order effects and product inhibition. The enzyme's ability to reach complete substrate conversion cannot be determined from these initial rate experiments, and was instead evaluated by chiral GC of overnight conversion with a GDH recycle system. The GDH regenerates the expensive NADH by redox reaction of NAD+ and inexpensive glucose (FIG. 1). In 1.5 mL reactions, replicates containing 10 mM MIBK substrate was mixed with an excess of 12 mM glucose, 10 U GDH, and a catalytic amount of NADH (200 μM). Histag purified K67S/E113V/N261L/V290C LeuDH-AmDH (0.13 mg) was added to each reaction and allowed to convert for 18 hours. An additional 0.13 mg of enzyme was then added and allowed to react for 10 hours to achieve the maximum conversion. One mL aliquots of the final reaction media were adjusted to pH>13 by the addition of 100 μL of 10 N NaOH and derivatized in toluene according to the TFAA protocol. The replicates were then compared against a calibration curve derived by the same procedure with simulated levels of conversion (FIG. 9), and an average substrate conversion of 92.5%±2.6 was achieved.

3.4.3 $^1$H NMR Product Confirmation

The product amine was additionally confirmed through $^1$H NMR. A 175 mL-scale amination reaction with GDH cofactor recycle was performed similar to previous conversion experiments. The reaction media was a 500 mM NH$_4$Cl/NH$_4$OH buffer at pH 9.6 containing; 10 mM MIBK, 12 mM glucose, 1 mM NADH, 2 mg GDH (85 U/mg). The histag purified quadruple variant (K67S/E113V/N261L/V290C @ 1314 μg/mL) was added in two 10 mL aliquots, initially and after 24 hrs. After 48 hours, the pH was increased (>12) with the addition 25 mL 10 N NaOH. The deprotonated amine product was then extracted with 40 mL methyl tert-butyl ether. Following separation, the solvent was removed through rotovap distillation, and the purified product was analyzed by $^1$H NMR. The reaction showed 84.7% conversion, yielding 29.5 mg (R)-1,3-DMBA (>99.3% e.e.) with spectra matching the standard. [$^1$H NMR (400 MHz, CDCl$_3$) δ 2.94 (sex, 1H, J=6.4 Hz), 1.65 (sep, 1H, 6.8 Hz), 1.24-1.02 (m, 2H), 1.04 (d, 3H, 6.4 Hz), 0.89 (d, 6H, 6.8 Hz)].

Enantioselectivity

The enantioselectivity was initially estimated by measuring the deamination activity toward individual enantiomers of methylbenzylamine (MBA). MBA was used in place of 1,3-DMBA for selectivity experiments since it had a reasonable level of activity and individual enantiomers of MBA were commercially available (Sigma Aldrich). A preference towards (R)-MBA over the corresponding (S)-enantiomer was evident in the discrepancies between the deamination activities of 0.586 U mg$^{-1}$ and 0.002 U mg$^{-1}$, respectively. These preliminary results were corroborated through direct measurement of the enantioselectivity of the MIBK amination in producing chiral 1,3-DMBA.

Figure 10:
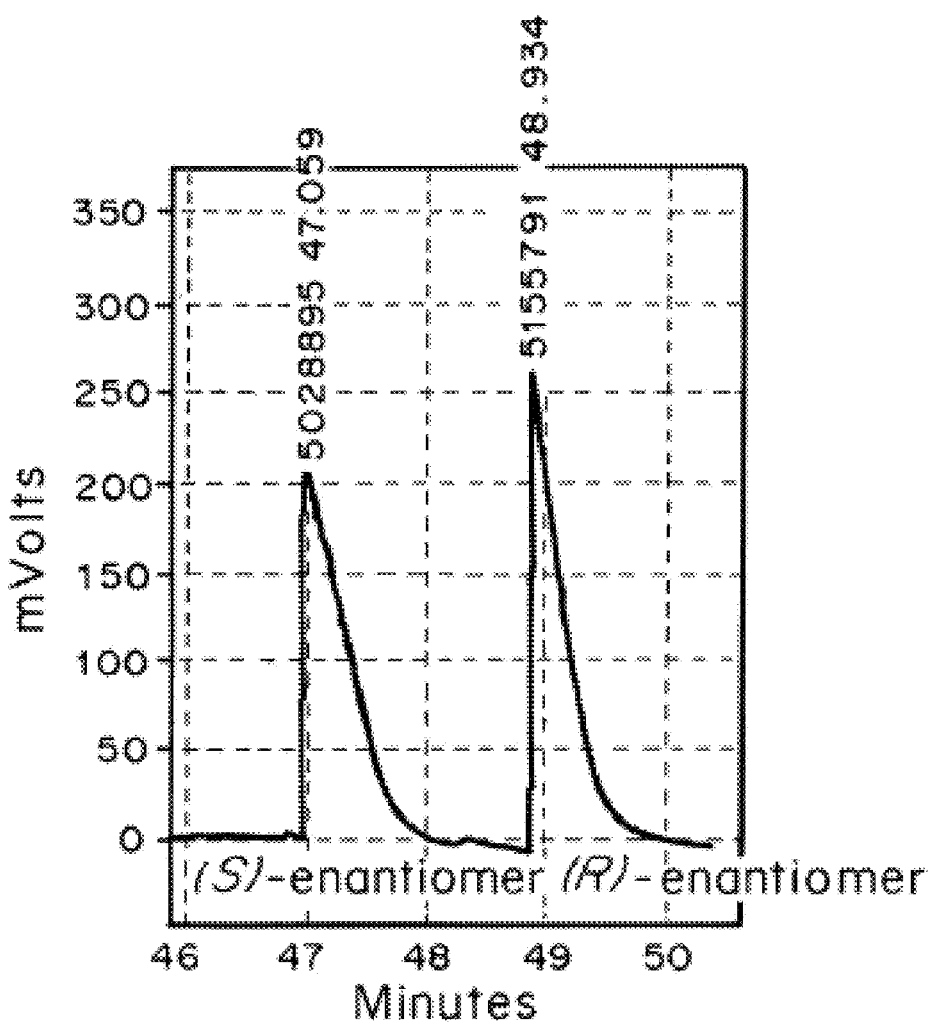
FIG. 10 is chromatogram showing chiral gas chromatography (FID) separation of derivatized racemic 1,3-DMBA standard.

Derivatization with trifluoroacetic anhydride (TFAA) and chiral gas chromatography allowed for the separation and quantification of individual enantiomers. The derivatized 1,3-DMBA enantiomers gave adequate baseline separation of the peaks, with elution times of 47.5 and 48.9 min for the (S)- and (R)-enantiomers, respectively. (FIG. 10) Overnight reactions were pH adjusted to 13 with 10 N NaOH and extracted from the aqueous phase into benzene. The amine was derivatized and concentrated through evaporation of benzene. The product was composed of the single (R)-enantiomer of DMBA. The product amine was injected in increasing concentrations until the (S)-enantiomer could be observed. The quadruple variant exhibited an e.e. of 99.8%. Pure enantiomers of 1,3-DMBA are not available commerically. Therefore, the product enantiomer was identified by optical rotation. Optical rotations of each enantiomer are represented in Table 11. The extracted product amine in methanol gave an optical rotation of −0.0039°, indicating the production of the (R)-enantiomer. This level of enantioselectivity was maintained even beyond 90% substrate conversion.

TABLE 11

Optical rotations of 1,3-DMBA enantiomers, neat, at 589 nm.

| Enantiomer of 1,3-DMBA | Optical rotation @ 589 nm (neat) |
|---|---|
| (R)-enantiomer | −11.2° |
| (S)-enantiomer | +11.2° |

Thermostability

Figure 11:
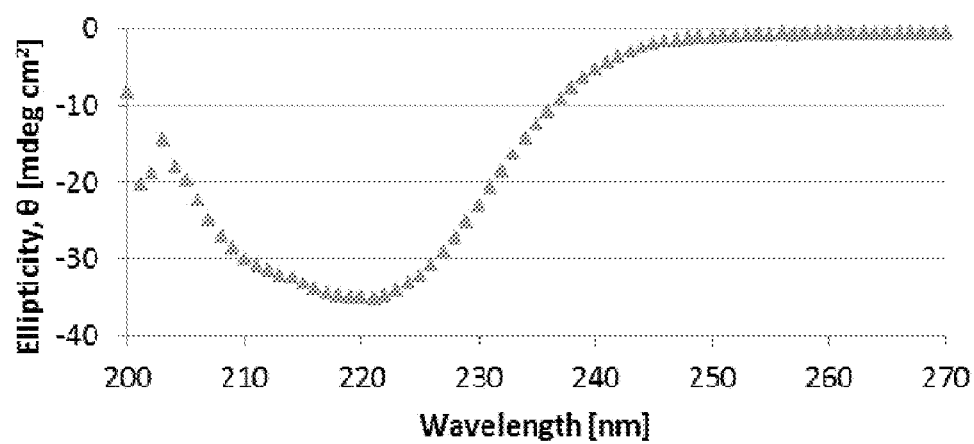
FIG. 11 is a scatter plot showing circular dichroism wavelength scans of wild type LeuDH to determine the maximum ellipicity of the protein (Ellipicity, θ [mdeg cm$^2$] vs. Wavelength [nm]).
Figure 12:
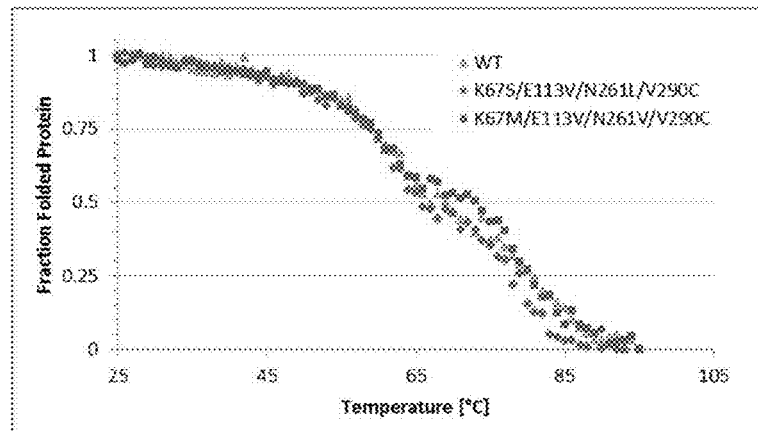
FIG. 12 is a scatter plot showing the fraction of folded LeuDH/AmDH as measured by circular dichroism spectroscopy of wild type LeuDH and top LeuDH-AmDH variants with normalized ellipticity, representing the percentage of folded protein (Fraction Fold Protein vs. Temperature [° C.]).

The thermostability of the top LeuDH-AmDH variants was compared to the wild type LeuDH by circular dichroism. Each protein was histag purified and dialyzed in 50 mM sodium phosphate buffer pH 8.0, 300 mM NaCl, removing the imidazole from the purification procedure. Each protein was diluted to 50 μg mL$^{-1}$ in a 0.1 cm quartz cuvette for analysis. Ellipticity was measured at 222 nm, corresponding to the maximum ellipticity of the protein as indicated by the wavelength scan (FIG. 11). Each protein was analyzed from 25° C. to 95° C. with a ramp rate of 1° C. min$^{-1}$. All three proteins exhibited nearly identical unfolding with melting temperatures (T$_M$) between 65° C. and 68° C., making any differences in stability difficult to characterize (FIG. 12). The four mutations within the LeuDH binding pocket did not destabilize the protein scaffold compared to the wild type.

Summary

An amine dehydrogenase was successfully developed from an existing amino acid dehydrogenase template by active-site targeted protein engineering. Eleven rounds of directed evolution have completely altered the enzyme's specificity and created amination activity. Each round of mutagenesis focused on a region of the binding pocket, including simultaneous mutation of neighboring residues to capture synergistic effects. These variants were screened by various high-throughput assays identifying minute increases in amination activity, and successful mutations were carried into future rounds of mutagenesis.

The largest improvements in activity were achieved by the cooperative mutation of residues K67 and N261. Their simultaneous mutation ultimately identified the most active quadruple mutant, K67S/E113V/N261L/V290C with novel reductive amination activity of 0.69 U mg$^{-1}$ with a corresponding k$_{cat}$ value of 0.46 s$^{-1}$. Within the first round of mutation, the native activity toward 1-Leu of 112 U mg$^{-1}$ was greatly decreased to less than 2 mU mg$^{-1}$; completely inverting the enzyme's specificity. The enantioselectivity of the wild-type enzyme was maintained despite the drastic changes to the binding pocket and yielded (R)-1,3-DMBA with an e.e. value of 99.8% at 92.5% conversion. This amine dehydrogenase exhibited activity toward a number of different substrates. The enzyme has also maintained its wild type stability making it an attractive catalyst in the synthesis of chiral amines. This is an example of a cofactor-dependent amine dehydrogenase capable of selectively synthesizing chiral amines from a prochiral ketone and free ammonia.

Example 3

Preparation of Phenylalanine Dehydrogenase Variants with Amine Dehydrogenase Activity Materials and Methods gDNA Preparation, Gene Isolation and Overexpression Genomic DNA from *Bacillus badius* Bachelor (ATCC#14574) was purchased from the American Type Culture Collection (ATCC, Manassas, Va.). The PheDH gene could not be successfully amplified out of the fully intact genome. The genome had to instead be digested prior to amplification using restriction sites; BamHI, BglII, EcoRI, and NdeI. These restriction sites are known not to cut within the PheDH gene, but would cut at several instances within the organism's genomic DNA. This allowed for a more manageable DNA template to amplify the PheDH gene. The gene was amplified using a standard PCR protocol with the forward primer, 5'-GGAATTCCATATGAGCTTAGTA-GAAAAAACATCCATCA-3' (SEQ ID NO:49) and reverse primer, 5'-CCGCTCGAGTATTAGTTGCGAATATC-CCATTTTG-3' (SEQ ID NO:50). These primers simultaneously inserted the restriction sites NdeI and XhoI prior to and following the gene, respectively. The locations of the restriction sites are indicated by bold font with each primer. This made for simple digestion and ligation into either pET17b or pET28a plasmids.

Protein Purification

PheDH from *Bacillus badius* was expressed and purified in a manner analogous to that described in Example 1, above.

Mutants and libraries were generated using an analogous protocol to that described in Example 1, above, with the only difference that the restriction site XhoI was used in place of HindIII Single and multiple variants containing mutations analogous to those found in 'LeuDH-AmDH library 10' were created using combinations of the primers in Table 12. LeuDH-AmDH library 11 had not yet been screened at the time of this experiment. The final variants were amplified from the respective mutational portions to yield the complete gene as described in the overlap extension protocol, and ligated into pET28a for subsequent expression and purification as detailed in Example 1, above.

The first library of PheDH-AmDH variants contained mutations at both positions K77 and N276. The directly substituted mutations from LeuDH-AmDH did not necessarily identify the optimal combination of mutations at these positions.

TABLE 12

Mutational primers applied to *B. badius* PheDH to create mutations analogous to those observed in LeuDH-AmDH

| LeuDH Mutant | PheDH Mutant | Primer |
|---|---|---|
| K67M | K77M | Fwd 5' GCCTTTCCAAAGGAATGACTTACATGTGCGCGGCG 3' TCCG (SEQ ID NO: 51) |
| | | Rev 5' CGGACGCCGCGCACATGTAAGTCATTCCTTTGGAA 3' AGGC (SEQ ID NO: 52) |
| E13V | T123V | Fwd 5' GGCGGCCGTTTCTATACAGGTGTGGATATGGGAAC 3' GAATATGGAAGATTTC (SEQ ID NO: 53) |
| | | Rev 5' GAAATCTTCCATATTCGTTCCCATATCCACACCTGT 3' ATAGAAACGGCCGCC (SEQ ID NO: 54) |
| N261V | N276V | Fwd 5' GCAATCGCCGGTTCAGCCGTGAATCAGCTGCTTAC 3' GGAGGATCAC (SEQ ID NO: 55) |
| | | Rev 5' GTGATCCTCCGTAAGCAGCTGATTCACGGCTGAAC 3' CGGCGATTGC (SEQ ID NO: 56) |

Successful IMAC purification with the histag was confirmed through SDS-PAGE of the purification fractions. Overexpression of the enzyme is indicated by a heavy band at 44 kDa in the clarified cell lysate and protein fractions. The removal of cellular proteins can be seen in the wash fractions. Faint bands of these proteins are observable in the purified fraction only after overloading. Under normal loading conditions, only the purified PheDH band is visible.

Spectrophotometric Assay

The activity of the purified protein was evaluated using a spectrophotometric assay at 340 nm as described in Section 3.2.3 at 25° C. in various concentrations of $NH_4Cl/NH_4OH$ buffer pH 9.6.

Mutagenesis and Library Generation

After eleven rounds of mutagenesis, three mutations were previously identified to be most influential in creating reductive amination activity in a LeuDH-based scaffold; Lys67Met, Glu113Val, and Asn261Val (Examples 1-2, above). Analogous mutations to these were identified through sequence alignment and applied to a similar amino acid dehydrogenase scaffold, phenylalanine dehydrogenase (PheDH) from *Bacillus badius* (48% identity, 66% similarity). Each of the point mutations, as well as combinations of these mutations, was evaluated for amination activity.

Simultaneous mutation of these residues can be used to identify any synergistic effects between their side chains. Since previous libraries had identified LeuDH K67M as a beneficial mutation, it was essential that the degenerate codon at that position contain methionine to ensure the identification of the best variant. The efficient NDT codon was excluded for this reason. With a two site library, codon selection must also be efficient to reduce the screening effort. A two site NNK library would require the screening of 3066 colonies, which is near the maximum screening capacity of the high throughput assay. The DDK codon greatly reduced the screening requirement to 969 colonies, while still including methionine and maintaining a broad range of mutation (Table 13).

TABLE 13

Comparison of degenerate codon distributions of PheDH library 1.

| Amino Acid | Codon DDK | Codon NDT | Codon NNK |
|---|---|---|---|
| Ala [A] | | | 2 |
| Arg [R] | 1 | 1 | 3 |
| Asn [N] | 1 | 1 | 1 |
| Asp [D] | 1 | 1 | 1 |

TABLE 13-continued

Comparison of degenerate codon distributions of PheDH library 1.

| Amino Acid | Codon DDK | Codon NDT | Codon NNK |
|---|---|---|---|
| Cys [C] | 1 | 1 | 1 |
| Gln [Q] |  |  | 1 |
| Glu [E] | 1 |  | 1 |
| Gly [G] | 2 | 1 | 2 |
| His [H] |  | 1 | 1 |
| Ile [I] | 1 | 1 | 1 |
| Leu [L] | 1 | 1 | 3 |
| Lys [K] | 1 |  | 1 |
| Met [M] | 1 |  | 1 |
| Phe [F] | 1 | 1 | 1 |
| Pro [P] |  |  | 2 |
| Ser [S] | 1 | 1 | 3 |
| Thr [T] |  |  | 2 |
| Trp [W] | 1 |  | 1 |
| Tyr [Y] | 1 | 1 | 1 |
| Val [V] | 2 | 1 | 2 |
| Stop | 1 |  | 1 |
| Codons | 18 | 12 | 32 |
| AA | 15 | 12 | 20 |

Screening of LeuDH Mutants and Libraries

Each of the single mutants and combinations of these mutations were individually expressed and purified. Each variant was evaluated for activity toward 20 mM 1,3-DMBA using the 340 nm spectrophotometric assay. The best combination of mutations was determined by the specific activity.

Figure 13:
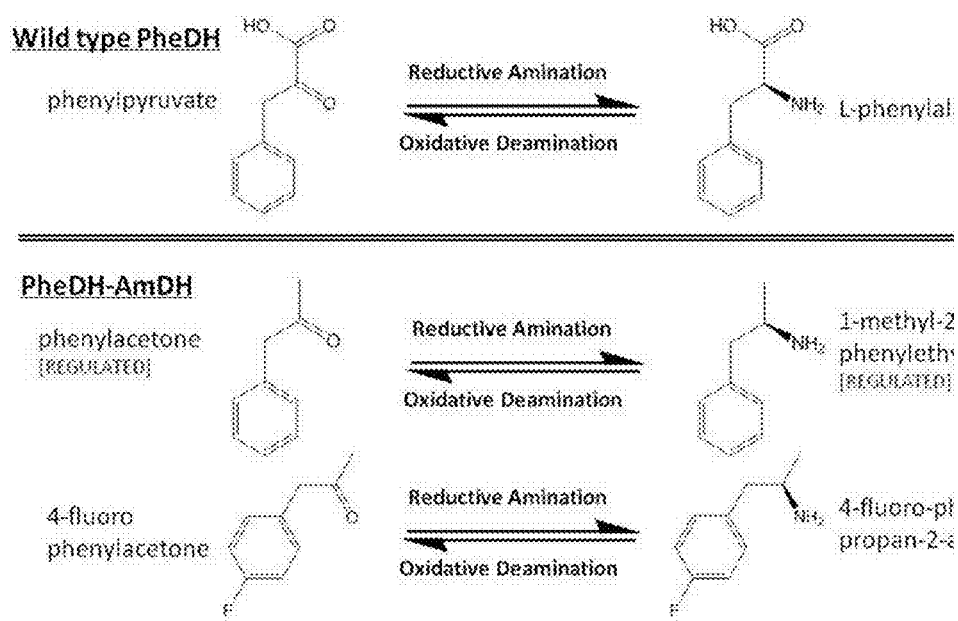
FIG. 13 are schemes showing the enzymatic reactions driven by wild type PheDH and engineered PheDH-AmDH (B).
Figure 14:
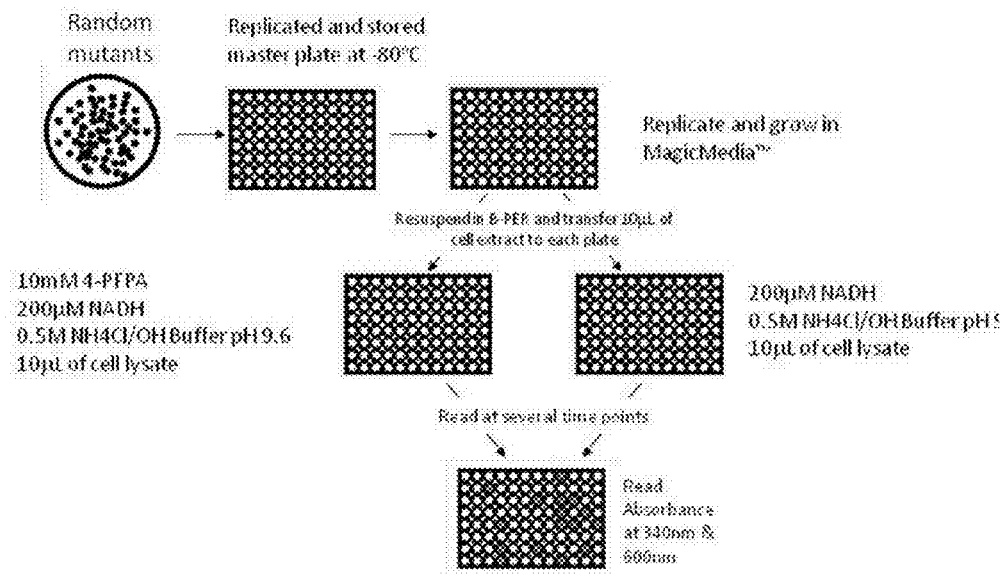
FIG. 14 is a diagram showing a forward screening assay applied to PheDH library 1 for reductive amination activity of para-fluoro phenyl acetone in 500 mM NH4Cl/NH4OH buffer pH 9.6, 200 μM NADH based upon 340 nm and 600 nm absorbance changes over multiple time points.

The best variant was further characterized for activity toward para-fluoro phenyl acetone (PFPA). PheDH's wild type keto-acid substrate is phenylpyruvate, and the equivalent AmDH ketone substrate would be phenylacetone (FIG. 13). Phenylacetone is not commercially available, because it is regulated as a Schedule 2 narcotic. This was overcome by the use of a fluorinated derivative, para-fluoro phenyl acetone (Sigma Aldrich) which is commercially available and unregulated.

Figure 15:
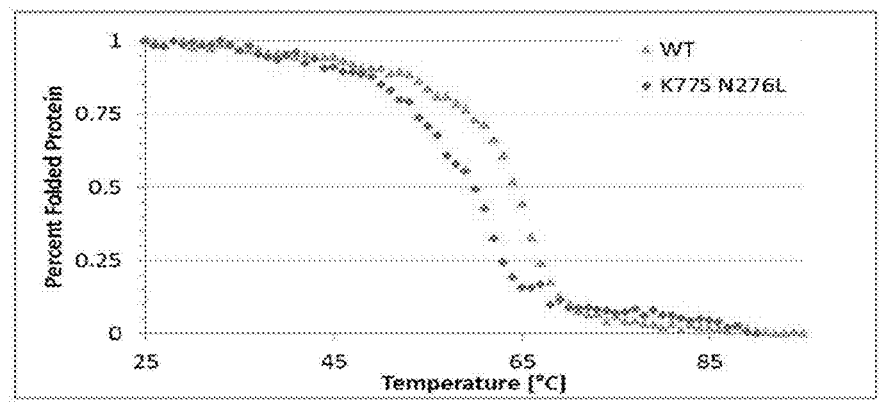
FIG. 15 is a scatter plot showing the fraction of folded PheDH/AmDH as measured by circular dichroism spectroscopy of wild type PheDH and top PheDH-AmDH variant, K77S N276L with normalized ellipticity representing the percentage of folded protein (protein concentrations 100 μg mL-1 in 50 mM sodium phosphate buffer pH 8.0) (Fraction Fold Protein vs. Temperature [° C.]).

The evaluation of the LeuDH-AmDH mutations on the PheDH scaffold identified the double variant K77M N276V as the most active, with a $k_{cat}$ value of 0.128 s$^{-1}$ and a reasonable $K_M$ value of 4.61 mM. Future variants with activity below this level were no longer considered significance. This elevated activity allowed for the application of a stringent screening assay (FIG. 15) in screening the K77DDK N276DDK library. Screening in the deamination direction to exploit the higher activity was no longer necessary. Instead, the amination activity was directly evaluated using a similar absorbance-based assay.

After mutagenesis, colonies were picked and expressed as described in Section 3.2.4. As the expression plates thawed, the cell pellets were gently vortexed with 30 μL of B-PER to uniformly resuspend and lyse the cells. The crude cell lysate was split in 10 μL aliquots into two plates; a reaction and background plate. A reaction mixture (200 μL) containing 10 mM PFPA and 200 μM NADH in 500 mM NH$_4$Cl/NH$_4$OH buffer was added to each well. The same mixture lacking PFPA was added to the background plate. Absorbance measurements at 340 nm and 600 nm began immediately unlike the previous end-point assays, and continued periodically over the course of 1.5 hours.

Active variants were identified by the rate of change in absorbance at 340 nm, corresponding to the fastest activity. The wells exhibiting the fastest rate change over that of the background plate were selected for further characterization. Some variants consumed the cofactor too quickly (<5 min) to be observed over multiple time points, and gave low absorbance in the initial time point. These variants were included for further characterization. The successful variants were sequenced (MWG Operon), and each unique sequence was expressed in pET28a/BL21 for histag purification and determination of $k_{cat}$ and $K_M$ values with PFPA.

Results

Rhodococcus Sp. M4 Phenylalanine Dehydrogenase K66M Mutants were Difficult to Express The wild-type gene sequence of phenylalanine dehydrogenase from Rhodococcus sp. M4 was attained from Brunhuber et al. (Brunhuber, et. Al., Critical Reviews in Biochemistry and Molecular Biology, 29, (6): 415-467 (1984)). The nucleic acid sequence was synthesized by an external vendor (MWG Operon) and provided in a pUC57 vector. The gene was amplified out of the host plasmid, along with the simultaneous insertion of restriction sites NdeI and HindIII (bold) using the primers; N-terminal 5'-GGGAATTCCATATGAG-TATCGACAGCGCACTGAAC-3' (SEQ ID NO:57), and C-terminal 5'-CCATGATTACGCCAAGCTTGC-3' (SEQ ID NO:58). A second amplification was performed to insert a STOP codon at the C-terminus of the protein sequence and allow for proper translation and expression. The forward and reverse primers, 5'-CGACAACGACAGCGACTGC-CTAGGGCCCGTCGACTGCAG-3' (SEQ ID NO:59) and 5'-CTGCAGTCGACGGGCCCTAG-GCAGTCGCTGTCGTTGTCG-3' (SEQ ID NO:60) respectively, were used in this amplification. The final insert was then digested and ligated into pET28a for overexpression and histag purification as described in Example 1, above. The wild-type protein was successfully purified and activity confirmed (39.5 kDa, 46 U mg$^{-1}$).

The wild-type gene was then mutated with the analogous mutations beneficial to creating AmDH in the LeuDH scaffold (Example 2, above). These residues were identified through sequence alignment.

The K66M mutation was created by applying the primers, 5'-GGGGGCGATGACGTTGATGATGGCAGT-GAGCAACCTTCC-3' (SEQ ID NO:61) and 5'-GGAAGGT-TGCTCACTGCCATCATCAACGTCATCGCCCCC-3' (SEQ ID NO:62), in the overlap extension protocol described in Sambrook et al. After sequence confirmation, overexpression of the K66M single mutant was attempted in pET28a vector and BL21 competent cells. This overexpression was unsuccessful, and the protein was not expressed. The K66M mutant DNA was then used as a template for mutation back to the parental sequence, K66. Upon mutation back to the parental sequence, successful overexpression of the protein was restored. This indicated that the Rhodococcus sp. M4 PheDH was not tolerant to mutation at this position without introducing difficulties in expression. An alternative PheDH gene from Bacillus badius was used in future experiments to circumvent these complex problems with overexpression.

Evolution of Phenylalanine Dehydrogenase from Bacillus badius Bachelor

Phenylalanine dehydrogenase from Bacillus badius Bachelor was chosen as an alternative scaffold to the Rhodococcus sp. M4 gene. The B. badius gene has been shown to be reasonably active with a $k_{cat}$ value of 39 s$^{-1}$ and has been characterized in literature (Asano, et., al., European Journal of Biochemistry, 168, (1): 153-159 (1987); Villalonga, et al., Sensors and Actuators B: Chemical, 129, (1): 195-199 (2008); Villalonga, et al., Enzyme and Microbial Technology, 40, (3): 471-475 (2007); Villalonga, et al., Biotechnology Letters, 27, (17): 1311-1317 (2005)). Another advantage of the B. badius PheDH is its increased similarity to the LeuDH scaffold (66% similarity) compared to the Rhodococcus sp.

M4 (54% similarity). This increased the chances of successful translation of AmDH mutations from the previous scaffold.

The Rhodococcus sp. M4 and B. badius PheDHs are very different from each other on a sequence level, sharing only 32% identity and 50% similarity. Coming from the same structural sub-family, they share a much stronger correlation in their folding motifs. Since there currently is no crystal structure available for the B. badius PheDH, the sequence was folded over the 1BW9 crystal structure and superimposed over the original scaffold using SuperPose. The resulting B. badius structure is nearly identical to the 1BW9 crystal structure with a backbone RMSD of only 1.69 Å, with the major deviation occurring at a loop region evident in the primary sequence. This tertiary structure similarity attests to the use of the 1BW9 crystal structure as a model of protein-substrate interactions.

Wild-Type PheDH Activity

The wild-type PheDH from B. badius was characterized to ensure proper expression and folding prior to mutation. The purified PheDH exhibited activity levels greater than 257 U mg$^{-1}$ in the amination of phenylpyruvate (500 mM NH$_4$Cl/NH$_4$OH buffer pH 9.6, 200 μM NADH, 5 mM phenylpyruvate at 25° C.), and 39.5 U mg$^{-1}$ in the deamination of L-Phe (0.1 M Glycine buffer pH 10.0, 1 mM NAD+, 20 mM L-Phe at 25° C.). $K_M$ values were determined for the substrates when possible, and corresponded well to those values found in literature (110). Additionally, the K1 value of ammonia was determined to be 5.0 M. The $K_M$ of phenylpyruvate could not be determined due to its high absorbance at the analytical wavelength. The wild-type enzyme was determined to be properly folded and active.

Comparison of Beneficial Mutations Identified in LeuDH-AmDH

To directly and easily create a basis of PheDH-AmDH activity, each of the mutations identified in LeuDH-AmDH were tested individually and in combination on the PheDH scaffold for the identification of residues which were influential in creating AmDH activity. The specific activities of the variants with 1,3-DMBA can be seen in Table 12

The PheDH double variant, K77M/N276V was the best combination of the LeuDH mutations. Both of these residues are known to interact with the wild-type substrate at the carboxyl moiety, and their synergistic effects are reflected in the large increase in AmDH activity when compared to their individual substitutions.

TABLE 14

AmDH activity on 1,3-DMBA and MIBK by PheDH variants derived from analogous LeuDH-AmDH mutations.

| LeuDH Variant | PheDH Variant | Deamination Activity 40 mM 1,3-DMBA, $k_{cat}$ (s$^{-1}$) | Amination Activity 40 mM MIBK, $k_{cat}$ (s$^{-1}$) |
|---|---|---|---|
| Wild Type | Wild Type | —No Activity— | |
| Lys67Met | Lys77Met | 0.0033 ± 0.000 | 0.0009 ± 0.000 |
| Glu113Val | Thr123Val | 0.0013 ± 0.000 | n.m. |
| Asn261Val | Asn276Val | 0.0016 ± 0.000 | n.m. |
| Lys 67Met Glu113Val | Lys77Met Thr123Val | 0.0010 ± 0.000 | n.m. |
| Lys67Met Asn261Val | Lys77Met Asn276Val | 0.0722 ± 0.004 | 0.0037 ± 0.000 |
| Lys67Met Glu113Val Asn261Val | Lys77Met Thr123Val Asn276Val | 0.0011 ± 0.000 | n.m. |

Amination: 500 mM NH$_4$Cl/NH$_4$OH buffer pH 9.6, 200 μM NADH, 40 mM MIBK at 25° C.,
Deamination: 0.1M Glycine buffer pH 10.0, 1 mM NAD+, 20 mM 1,3-DMBA at 25° C.

Screening of Library and Hits Characterization

Prior to the screening of the PheDH K77DDK N276DDK library, the diversity of the mutations were checked. Twenty colonies were sequenced to ensure the desired breadth of mutation was achieved at each position, and a large percentage of parental variants were not present.

A total of 36 wells were labeled as highly active by the assay for subsequent characterization. Sequencing of these hits yielded 21 unique pairs of mutations, each of which were transformed into a pET28a plasmid for subsequent expression and his-tag purification. These purified proteins were individually characterized for activity toward the amination of PFPA to more accurately determine which combination of mutations performed best (Table 16). All 21 pairs of mutations were active amine dehydrogenases, eight of which provided $k_{cat}$ values greater than 1 s$^{-1}$ in the amination of PFPA. The top variant 1H4 contained the mutations K77S N276L with an apparent $k_{cat}$ value of 2.8 s$^{-1}$ and $K_{M,\ PFPA}$ value of 4.37 mM in 500 mM NH$_4$Cl/NH$_4$OH buffer pH 9.6 with 200 μM NADH. The K77W N276E variant also exhibited exceptionally high levels of activity with an apparent $k_{cat}$ value of 2.63 s$^{-1}$ and a $K_{M,\ PFPA}$ value of 5.32 mM. The K77S N276L variant was selected as the top candidate for further characterization, since it had the highest apparent $k_{cat}$ value and a lower $K_M$ than the K77W N276E variant.

TABLE 15

Randomly selected colonies of PheDH library 1 confirming diversity at positions K77 and N276 by successful application of overlap extension mutagenesis

| Colony | K77 | N276 |
|---|---|---|
| 1 | Leu | Trp |
| 2 | Asn | Phe |
| 3 | Val | Phe |
| 4 | Val | Asp |
| 5 | Arg | Gly |
| 6 | Arg | Asp |
| 7 | Asn | Lys |
| 8 | Gly | Ile |
| 9 | Tyr | Cys |
| 10 | Ser | Leu |
| 11 | Gly | Gly |
| 12 | Trp | Ile |
| 13 | Glu | Arg |
| 14 | Asp | Lys |
| 15 | Trp | Met |
| 16 | Glu | Lys |
| 17 | Glu | Glu |
| 18 | Cys | Cys |
| 19 | Gly | Leu |
| 20 | Lys | Trp |

TABLE 16

Characterization of histag purified PheDH library 1 hits. Kinetic parameters $k_{cat}$ and $K_M$ determined by non-linear fit for the amination of PFPA in 500 mM NH$_4$Cl/NH$_4$OH pH 9.6, 200 μM NADH

| Hit | K77 Residue | N276 Residue | Non-Linear Michaelis Menten | |
|---|---|---|---|---|
| | | | $k_{cat}$ (s$^{-1}$) | $K_M$ (mM) |
| 1H4 | Ser | Leu | 2.802 ± 0.536 | 4.4 ± 1.6 |
| 7F10 | Trp | Glu | 2.631 ± 0.159 | 5.3 ± 0.6 |
| 4H6 | Met | Met | 1.818 ± 0.190 | 7.9 ± 1.3 |
| 7A3 | Ser | Met | 1.513 ± 1.900 | 42.4 ± 50.0 |
| 4D2 | Ser | Ser | 1.307 ± 0.364 | 14.5 ± 5.2 |
| 10F12 | Cys | Leu | 1.285 ± 0.246 | 3.5 ± 1.4 |
| 2F4 | Met | Leu | 1.283 ± 0.100 | 4.2 ± 0.6 |
| 3G7 | Ser | Val | 1.055 ± 0.185 | 4.4 ± 1.5 |

TABLE 16-continued

Characterization of histag purified PheDH library 1 hits. Kinetic parameters $k_{cat}$ and $K_M$ determined by non-linear fit for the amination of PFPA in 500 mM NH$_4$Cl/NH$_4$OH pH 9.6, 200 µM NADH

| Hit | K77 Residue | N276 Residue | Non-Linear Michaelis Menten $k_{cat}$ (s$^{-1}$) | $K_M$ (mM) |
|---|---|---|---|---|
| 5A3 | Met | Cys | 0.896 ± 0.080 | 1.5 ± 0.4 |
| 8D10 | Met | Leu | 0.858 ± 0.175 | 4.6 ± 1.8 |
| 6D12 | Ser | Phe | 0.792 ± 0.180 | 22.2 ± 0.4 |
| 9G3 | Met | Ser | 0.661 ± 0.074 | 4.9 ± 1.0 |
| 10G6 | Val | Leu | 0.558 ± 0.064 | 3.3 ± 0.8 |
| 1E11 | Cys | Ile | 0.549 ± 0.062 | 7.7 ± 1.4 |
| 4A9 | Gly | Ile | 0.339 ± 0.065 | 5.9 ± 2.0 |
| 11E1 | Ser | Gly | 0.275 ± 0.066 | 6.8 ± 2.7 |
| 9A11 | Gly | Cys | 0.029 ± 0.000 | — |
| 10A6 | Ser | Glu | 0.024 ± 0.013 | 9.0 ± 7.6 |
| 10H2 | Trp | Ile | 0.019 ± 0.010 | — |
| 12D6 | Trp | Gly | 0.017 ± 0.023 | — |
| 4C8 | Gly | Val | 0.017 ± 0.008 | — |

Example 4

Variant K77S/N276L is an Amine Dehydrogenase

The K77S N276L variant was characterized in detail for a number of properties including; pertinent kinetic parameters, the breadth of substrate specificity, thermo-stability, overall conversion, and enantioselectivity.

AmDH Activity and Substrate Specificity

Kinetic parameters, $k_{cat}$ and $K_M$, were determined for the enzyme and each of the reductive amination substrates; respectively. The original assay conditions of 500 mM NH$_4$Cl/NH$_4$OH buffer did not saturate the enzyme with respect to NH$_3$. The $k_{cat}$ value for this AmDH enzyme with all three substrates saturated in aqueous NH$_4$Cl/NH$_4$OH buffer at pH 9.6 was 6.85 s$^{-1}$ at 25° C. This represents a near 15-fold enhancement above the maximum observed $k_{cat}$ of 0.46 s$^{-1}$ of the previously developed LeuDH-AmDH. The increase in buffer concentration did have a salt effect upon the $K_M$ value of PFPA, which increased to 7.75 mM under saturated reaction conditions of 5 M NH$_4$Cl/NH$_4$OH buffer pH 9.6 with 200 µM NADH. The $K_M$ value for NADH remained low as with the wild-type enzyme with a $K_M$ value of 23.9 µM.

The significant increase in the $K_M$ of NH$_3$ ($K_{M, NH3}$=1.27 M) seen in the conversion of para-fluoro phenyl acetone amination, as compared to the amination of phenylpyruvate ($K_{M, NH3}$=64.5 mM) can be attributed to decreased activation of the alpha carbon caused by changes in electron density with the new substrate. The original phenylpyruvate structure has a carboxyl group neighboring the alpha carbon where the nucleophilic attack of ammonia occurs. This carboxyl moiety will lessen the electron density at the alpha carbon make the nucleophilic attack more favorable compared to the ketone substrate.

The breath of the substrate profile was analyzed through the amination and deamination activity toward a number of different ketones and amines, respectively. The diversity of these ketones varied in structure from small aliphatic ketones such as 3-methyl-2-butanone, to larger aromatic ketones with additional functionality, such as phenoxy-2-propanone. Several other ketone compounds were found to exhibit reasonable levels of activity (Table 17).

TABLE 17

Substrate specificity of top variant, K77S N276L PheDH. Amination in 500 mM NH$_4$Cl/NH$_4$OH, pH 9.6, 200 µM NADH, 20 mM substrate at 25° C.

| Substrate | Activity (mU/mg) | Substrate | Activity (mU/mg) |
|---|---|---|---|
| R-MBA† | 1.9 ± 1.8 | cyclopentanone | 0.9 ± 0.5 |
| S-MBA† | <1.0 | cyclohexanone | 27.5 ± 1.4 |
| R/S-MBA*,† | 0.5 ± 0.2 | ethylpyruvate | 18.4 ± 5.9 |
| MIBK | 77.0 ± 1.3 | benzaldehyde | 31.4 ± 8.7 |
| 1,3-DMBA† | 166.3 ± 0.0 | 2-methylcyclohexanone | 19.3 ± 1.1 |
| acetophenone | <1.0 | 3-methylcyclohexanone | 41.1 ± 2.1 |
| phenoxy-2-propanone | 540.8 ± 6.9 | 3-methyl-2-butanone | 72.7 ± 1.4 |
| 2-hexanone | 155.7 ± 1.4 | 1-Boc-piperidone | 7.8 ± 1.1 |
| 3-hexanone | 1.6 ± 0.5 | Benzyloxyacetic acid | 22.6 ± 0.7 |
| 3-pentanone | 1.3 ± 0.0 | | |

*40 mM, 20 mM of each enantiomer.
†Deamination in 0.1M glycine buffer, pH 10.0, 1 mM NAD+, 20 mM substrate at 25° C.

The enzyme shows increased activity toward methyl-ketones versus those which are ethyl-ketones or cyclic-ketones. The top five most active ketones; PFPA, phenoxy-2-propanone, 2-hexanone, methyl isobutyl ketone and 3-methyl-2-butanone are all methyl-ketones. This specificity is also observed in the large differences in activity toward 2-hexanone (155.7 mU/mg) versus 3-hexanone (1.6 mU/mg). Despite the structural similarities, the methyl-ketone 2-hexanone, exhibits approximately 100-fold higher activity. Similarly, the enzyme requires at least a one carbon linkage between the alpha carbon and the substrate's phenyl ring. This is reflected by the unobservable activity toward acetophenone, as well as the low deamination activity of methyl benzyl amine.

Thermostability

Figure 16:
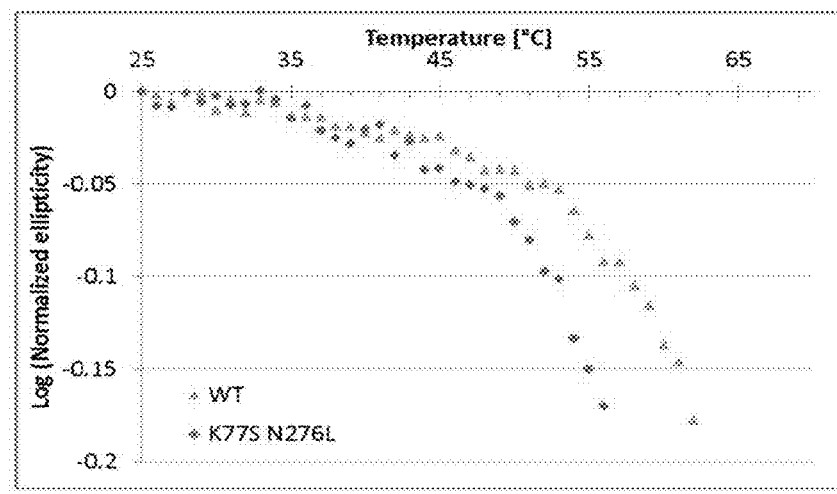
FIG. 16 is a scatter plot showing the semi-log plot of fraction of folded PheDH/AmDH as measured by circular dichroism spectroscopy of wild type PheDH and top PheDH-AmDH variant, K77S N276L with normalized ellipticity representing the percentage of folded protein (protein concentrations 100 μg mL-1 in 50 mM sodium phosphate buffer pH 8.0) (Log(Normalized Ellipticity) vs. Temperature [° C.]).

The thermostability of the AmDH was compared to its wild-type scaffold using two different methods, circular dichroism (CD) and a temperature versus activity profile. The mutation of the enzyme scaffold has affected the thermostability, in addition to the enzyme's function. Both the wild-type PheDH and the AmDH exhibit similar characteristics in the loss of secondary structure as indicated through CD. Both enzymes showed the same gradual loss of structure at temperatures up to 30 degrees Celsius (FIGS. 15 and 16), implying that the cause for the early loss of structure is inherent in the wild-type protein. Beyond 30 degrees, there is an earlier onset in the pronounced loss of structure of the double variant compared to the wild type; however, the slope folded fraction over temperature stays constant, indicative of constant enthalpy of melting. The K77S N276L mutations have slightly destabilized the protein structure, resulting in a melting point of 59.9° C., 4.4° C. less than the wild type. The specific cause for this change is difficult to determine. It likely to be either disruption of the 'ideal' packing of the wild-type enzyme's hydrophobic core or a net decrease in hydrophobicity by the amino acid substitutions which leads to a lower folding entropy.

Figure 17:
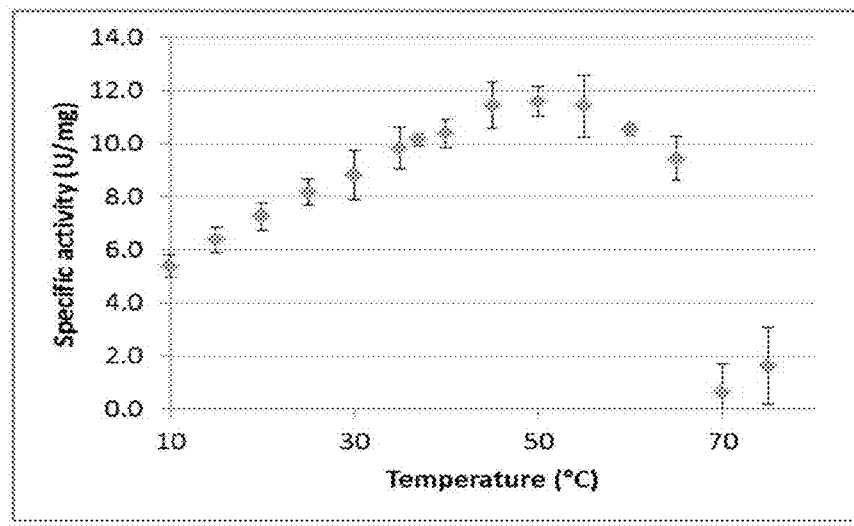
FIG. 17 is a scatter plot showing the Specific Activity (U/mg) vs. Temperature (° C.) of PheDH-AmDH K77S N276L double variant.

The thermostability of the double variant K77S N276L was additionally determined by a temperature versus activity plot, showing the results of amination activity measured in 5 M NH4Cl/NH4OH buffer pH 9.6, 200 µM NADH, 20 mM PFPA for 2 minutes (FIG. 17). This plot shows the enzyme's Arrhenius activation through the lower temperature range (10-45° C.), although this thermal activation should appear to be exponentially increasing. The near linear increase corresponds to a low activation energy of 241 J mol$^{-1}$. The maximum specific activity was 11.6 U mg$^{-1}$ at a temperature of 50° C. Above 50° C., the enzyme began to rapidly lose activity as a result of denaturation. This deactivation correlated well with the circular dichroism data, where a dramatic loss of secondary structure was observed from 50° C. to 70° C.

Conversion with Cofactor Recycle System

Figure 18:
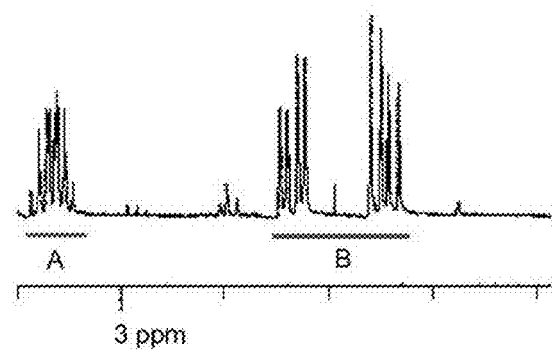
FIG. 18 is a $^1$H nuclear magnetic resonance spectrogram showing indicating the presence of chiral 1-(4-fluorophenyl)-propane-2-amine: "A" labels a sextuplet splitting representative of the proton at the chiral center, and "B" labels a pair of doublet-doublet splits from the C3 hydrogens reflecting the chiral center.

A reaction system capable of high-level conversions was demonstrated by pairing the AmDH with a GDH cofactor recycle system. The GDH consumes glucose present in solution to cheaply and efficiently regenerate the NADH cofactor, allowing conversion to continue beyond stoichiometric depletion of NADH. In a 100 mL reaction volume containing 20 mM PFPA, conversion was allowed to continue for 48 hours followed by extraction and $^1$H-NMR to confirm the product formation and conversion levels. The addition of 7.48 mg of the AmDH enzyme converted 89.4% of the 4-fluorophenyl acetone substrate to the product 1-(4-fluorophenyl)-propane-2-amine over 48 hours with an isolated yield of 66.2%. Under the same reaction conditions, 17.46 mg of the AmDH enhanced the overall conversion to 93.8% and 73.9% yield. Evidence of chirality was indicated by different NMR signals of the C3 hydrogens (δ 2.67, 2.49) which are adjacent to the C2 stereocenter (FIG. 18).

[4-fluorophenyl acetone substrate;

$^1$H NMR (400 MHz, CDCl$_3$) δ 7.26-7.00 (m, 4H), 3.68 (s, 2H), 2.16 (s, 3H).

(R)-(−)-1-(4-fluorophenyl)-propane-2-amine product;

$^1$H NMR (400 MHz, CDCl$_3$) δ 7.26-6.95 (m, 4H), 3.12 (sex, 1H, J=3.9 Hz), 2.67 (dd, 1H, 6.3 Hz, 13.2 Hz), 2.49 (dd, 1H, 6.3 Hz, 13.2 Hz), 1.10 (d, 3H, 6.4 Hz)].

Enantioselectivity

Equally important to conversion is maintaining the selectivity of the enzyme after altering the substrate specificity. Preservation of the wild type (S)-selectivity towards phenylalanine will result in the asymmetric production of (R)-1-(4-fluorophenyl)-propyl-2-amine due to a change in Cahn-Ingold-Prelaw priority. The product amine resulting from enzymatic conversion with the co-factor recycle was isolated and derivatized using trifluoroacetic anhydride for analysis via chiral gas chromatography. An enantiomeric excess of >99.8% toward (R)-1-(4-fluorophenyl)-propyl-2-amine was confirmed, however, further resolution of the selectivity was limited by the separation capability of the chiral column. Throughout all experiments, the (S)-enantiomer remained below the detection limits. Even as the enzyme approaches levels of conversion beyond 90%, the high enantioselectivity toward (R)-1-(4-fluorophenyl)-propyl-2-amine is maintained. This renders the AmDH/GDH system a viable method for the production of chiral amines.

Confirmation of the (R)-selectivity was achieved through polarimetry, since single enantiomers of (4-fluorophenyl)-propyl-2-amine are not commerically available. Suspension of the isolated product amine in methanol resulted in a negative optical rotation (−1.73°, 10 cm path length at 0.3 mM amine), confirming the (R)-(−)-enantiomer to known standards.

Summary

Previous knowledge in the evolution of an amine dehydrogenase, particularly the influence of binding pocket residues Lys77 and Asn276, allowed for a direct route to an active AmDH from PheDH. With a reasonably active starting variant, a stringent high-throughput screening of a single two-site library further enhanced the desired reductive amination activity to a k$_{cat}$ value of 6.85 s$^{-1}$ at 25° C. The high enantioselectivity was maintained throughout the evolution process. The enzyme's e.e. value of >99.8% toward the (R)-enantiomer, even after high levels of conversion, renders it an attractive candidate for the asymmetric production of chiral amines. The reaction can be simply and cheaply driven to conversions in excess of 90% when paired with a cofactor recycle system. Despite a 4.4 degree Celsius decrease in thermostability, the enzyme remains broadly activity over a large temperature range from 10 to 50° C., with a maximum observed specific activity of 11.6 U mg$^{-1}$. The novel AmDH exhibits amination activity towards a range of ketone substrates, which makes it a good starting point for further evolution to increase activity toward specific API targets.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Example 5

PheDH-AmDH K77M N276V has Activity with an Acetone Cosolvent

Figure 20:
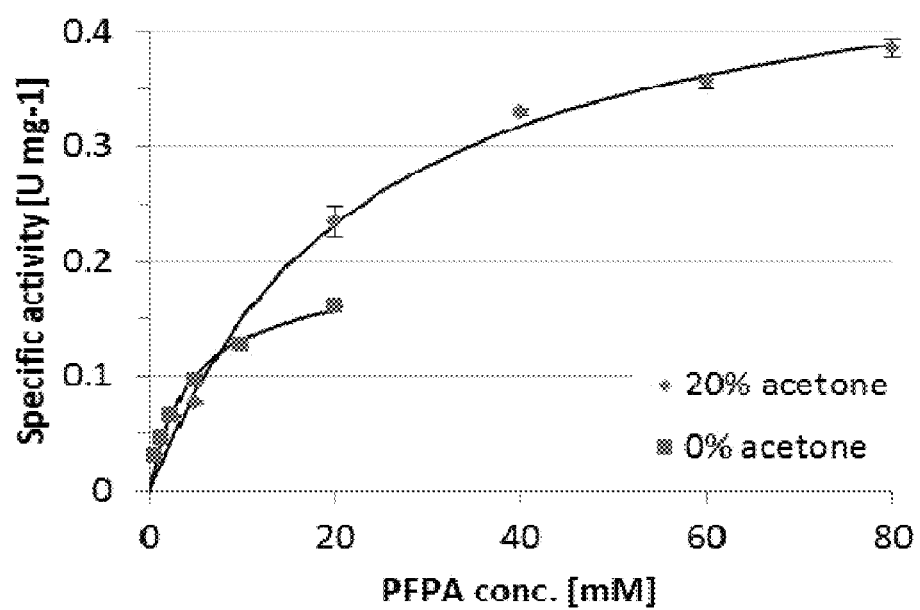
FIG. 20 is a best-fit curve showing the specific activity [U mg$^{-1}$] of PheDH-AmDH K77M/N276V in acetone as a function of substrate concentration (PFPA concentration. [mM].

The enzyme tolerates acetone concentrations as high as 20% v/v. The PFPA substrate has a limited solubility of 40 mM in aqueous media, but was increased to 60 mM with the addition of acetone. The increased substrate concentration resulted in a 40% increase in the maximum observable k$_{cat}$ (FIG. 20), from 0.11 s$^{-1}$ in aqueous solution to a value of 0.26 s$^{-1}$ with 20% acetone. The K$_M$ were affected by the addition of acetone, increasing from a value of 4.6 mM to 23.1 mM in aqueous and 20% acetone, respectively. hydrophobic substrates.

Example 6

A chimeric F-AmDH/L-AmDH Shows Amine Dehydrogenase Activity

Materials and Methods

Construction of a Chimeric Amine Dehydrogenase

Figure 21:
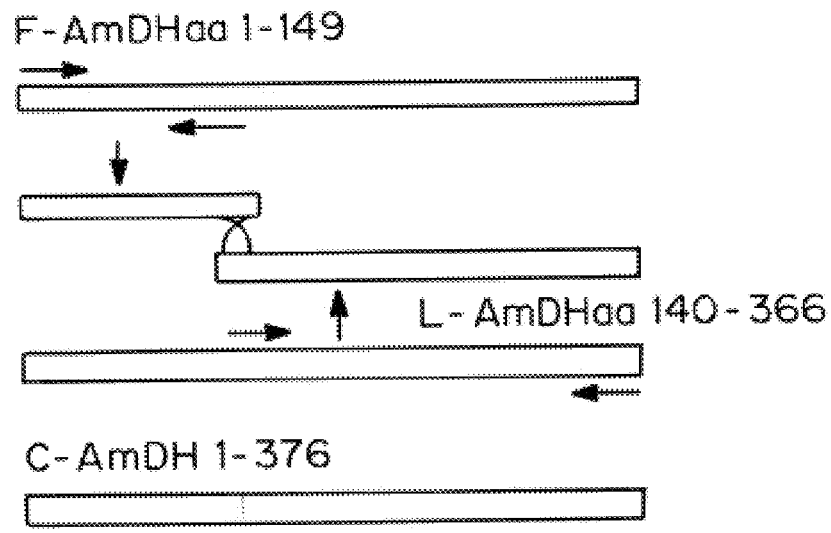
FIG. 21 is a drawing showing the design and domain structure of C1-AmDH.

FIG. 21 shows a diagram of the overall construction of the chimeric enzyme. The ligation point of the domains was constructed according to (Kataoka et al. *J. Biochem.*, 116, 931-936, 1994), but overlap PCR was used to generate the new construct.

This construct was cloned into pET2Ha and expressed in BL21plys. cells. Expression was successful and yielded between 10 mg-16 mg/100 ml culture. The enzyme was purified using affinity chromatography with Ni—Ni-NTA The histag for purification is vector-derived and is located at the N-terminus of the enzyme.

Sequences of C1-AmDH and C2-AmDH

C1-AmDH
ATGAGCTTAGTAGAAAAAACATCCAT-
CATAAAAGATTTCACTCTTTTTGAAAAA ATGTCT-
GAACATGAACAAGTTGTTTTTGCAAC-
GATCCGGCGACAGGACTAAGG
GCCATTATCGCTATTCATGACACCA-
CACTCGGACCTGCGCTCGGCGGCT GCCGCATG-
CAGCCTTATAACAGTGTGGAAGAAGCAT-
TGGAAGATGCTCTTCGCC
TTTCCAAAGGAATGACTTACAGT-
TGCGCGGCGTCCGATGTCGACTTTGGCGGCG
GAAAAGCAGTCATTATCGGTGATCCGCA-
GAAAGATAAATCTCCAGAACTGTTCC GCGCGTTTG-

GCCAATTTGTTGATTCGCTTGGCGGC-
CGTTTCTATACAGGTACTG
ATATGGGAACGAATATGGAAGATTTCAT-
TCACGCCATGAAAGAAACAAACTGCA TTGT-
TGGGGTGCCGGAAGCGTATGGCTCT-
TCTGGCAACCCGTCGCCGGCCACGG
CTTACGGCGTATATCGTGGGAT-
GAAAGCGGCGGCGAAGGAAGCATTTGGCAGTG
ATTCGCTTGAAGGAAAAGTTGTCGC-
CGTCCAAGGAGTCGGCAATGTCGCCTACC ATTTAT-
GCCGCCATTTGCACGAAGAAGGAGC-
GAAACTCATCGTTACCGACATCA
ACAAGGAAGCGGTGGCGCGCGCGGTC-
GAGGAATTTGGGGCGAAAGCAGTCGACC CGAAC-
GACATTTACGGCGTGGAGTGCGA-
CATTTTTGCTCCATGCGCGCTCGGCG
GCATCATCAACGACCAAACGATTCCG-
CAGCTGAAAGCGAAAGTGATCGCCGGCT CGGCGT-
TGAATCAGCTGAAAGAGCCGCGCCATG-
GCGACATGATCCATGAAATGG
GCATCGTCTATGCACCAGATTATGTGAT-
CAACGCCGGCGGCTGCATCAACGTCG CCGAT-
GAGCTGTACGGCTACAACCGT-
GAACGGGCGATGAAAAAAATCGAGCAAA
TTTATGACAACATCGAAAAAGTGTTTGC-
CATCGCCAAGCGTGACAACATTCCAA CGTATGTG-
GCCGCTGACCGGATGGCCGAAGAAC-
GAATTGAAACGATGCGCAAAG
CGCGCAGCCAATTTTTGCAAAACGGC-
CATCATATTTTAAGCCGCCGCCGCCC GCTAA
(SEQ ID NO:63), which is a nucleic acid sequence encoding
SEQ ID NO:20 with an N-terminal methionine.
ATGAGCTTAGTAGAAAAAACATCCAT-
CATAAAAGATTTCACTCTTTTTGAAAAA ATGTCT-
GAACATGAACAAGTTGTTTTTTGCAAC-
GATCCGGCGACAGGACTAAGG
GCCATTATCGCTATTCATGACACCA-
CACTCGGACCTGCGCTCGGCGGCT GCCGCATG-
CAGCCTTATAACAGTGTGGAAGAAGCAT-
TGGAAGATGCTCTTCGCC
TTTCCAAAGGAATGACTTACAGT-
TGCGCGGCGTCCGATGTCGACTTTGGCGGCG
GAAAAGCAGTCATTATCGGTGATCCGCA-
GAAAGATAAATCTCCAGAACTGTTCC GCGCGTTTG-
GCCAATTTGTTGATTCGCTTGGCGGC-
CGTTTCTATACAGGTACTG
ATATGGGAACGAATATGGAAGATTTCAT-
TCACGCCATGAAAGAAACAAACTGCA TTGT-
TGGGGTGCCGGAAGCGTATGGTGGT-
GCGGGTGATAGCAGCGTGCTGACCG
CGTTTGGCGTGTTTCAGGGCATGCGTGC-
GAGCGCGGAACATCTGTGGGCGATC CGAGCCT-
GCGTGGCCGTAAAGTGGGTGTGGCGGGT-
GTGGGCAAAGTGGGCCATC
ATCTGGTGGAACATCTGCTGGAAGATG-
GTGCGGATGTGGTGATTACCGATGTGC GTGAA-
GAAAGCGTGAACCGTAGCACCCATAAA-
CATCCGAGCGTGACCGCTGTGG
CGGATACCGAAGCGCTGATTCGTAC-
CGAAGGCCTGGATATTTATGCTCCGTGCG
CGCTGGGTGGTGCGCTGGATGATGAT-
AGCGTGCCGGTGCTGACCGCTAAAGTGG TGTGCG-
GTGCGGCAAACCTGCAGCTGGCGCATC-
CGGGTGTGGAAAAAGATCTGG
CGGATCGTAGCATTCTGTATGCTCCG-
GATTATGTGGTGAACGCAGGTGGCGTGA TTCAG-
GTGGCGGATGAACTGCGTG-
GCTTTGATTTTGATCGTTGCAAAGCGAAAG
CGAGCAAAATTTTTGATACCACCCTGGC-
GATTTTTGCGCGTGCGAAAGAAGATG GCATTCCTC-
CGGCTGCGGCTGCGGATCGTATTGCG-
GAACAGCGTATGAGCGATG CGCGTTAA
(SEQ ID NO:64), which is a nucleic acid sequence encoding
SEQ ID NO:24.

Substrate Specificity of C1-AmDH

All ketone substrates for the amination direction were measured at 20 mM and dissolved at 60° C. in 4 M ammonium formate buffer. Enzyme specificity was measured at 60° C. for 5 min. with NADH as the cofactor at 340 nm.

Results

Engineering a Chimeric AmDH

The template LeuDH-AmDH (L-AmDH) and PheDH-AmDH (F-AmDH) discussed in Examples 1-4 were used to generate a chimeric amine dehydrogenase via domain shuffling (referred to as C1-AmDH). domain shuffling between L-AmDH and FcAmDH. Specifically, the NAD-binding domain of the F-AmDH was exchanged with the one from the L-AmDH. This created a chimeric enzyme with new activities, a specific preference for benzylic carbonyls, a feature the F-AmDH does not display. Overall, the new chimeric AmDH has lower specific activities. It also has a much different temperature activity profile in the presence of high concentrations of formate, which is more comparable to thermophilic enzymes than mesophilic enzymes, the group amine dehydrogenases belong to. Overall, this enzyme has several properties that distinguish it from the previously reported amine dehydrogenases.

Variants were also created by combining the mutations that lead to the L-AmDH and F-DH, as well as another new enzyme by using domain shuffling between a valine based AmDH (V-AmDH) and F-AmDH, referred to as C2-AmDH.

Substrate Specificity of C1-AmDH

The results of an assay testing substrate specificity for the amination reaction driven by C1-AmDH is provide in Table 18.

TABLE 18

| Substrate specificity of C1-AmDH. | | |
|---|---|---|
| substrate | U/ml | U/mg |
| pFPA | 13.8 | 1.725 |
| Acetophenone | 1.63 | 0.301851852 |
| a-tetralone | 0.58 | 0.107407407 |
| b-tetralone | 0 | 0 |
| Benzophenone | 0 | 0 |
| Adamantylmethylketone | 0 | 0.07 |
| 1,3-phenylbutanedione | 0.3 | 0.06 |
| 3-methyl-1-phenylbutanone | 0.16 | 0.03 |
| dibenzylketone | 1.39 | 0.257407407 |
| 3-oxo-phenylbutyricacid ethylester | 0 | 0 |
| pinacolone | 0.72 | 0.133333333 |

Activities were also measured photometrically with 100 mM (+/−) methylhenzylamine (0.58 U/mg) as well as 100 mM (R)-methylbenzylamine. (0.98 U/mg), 50 mM (R,S)-adamanylethlamine (0.04 U/mg) and determined the enantioselectivity for this enzyme to be (R).

$K_m$ and $k_{cat}$ Values for C1-AmDH

The values for acetophenone, pFPA; NADH and NH3 were determined and are summarized in Table XX, all measured at 60° C.

TABLE 19

Kinetic Values for C1-AmDH

| Substrate | $K_M$ (mM) | kcat (s$^{-1}$) | kcat/$K_M$ (M$^{-1}$ s$^{-1}$) |
|---|---|---|---|
| Acetophenone | 5.2 | 0.24 | 48 |
| pFPA | 1.1 | 1.24 | 1127 |
| NH$_3$ | 350 | 1.09 | 3 |
| NADH | 0.04 | 0.92 | $2 \times 10^4$ |

The $K_m$ values show improvement over previously established amine dehydrogenases.

Temperature Vs Activity Profile for C1-AmDH

Figure 22A:
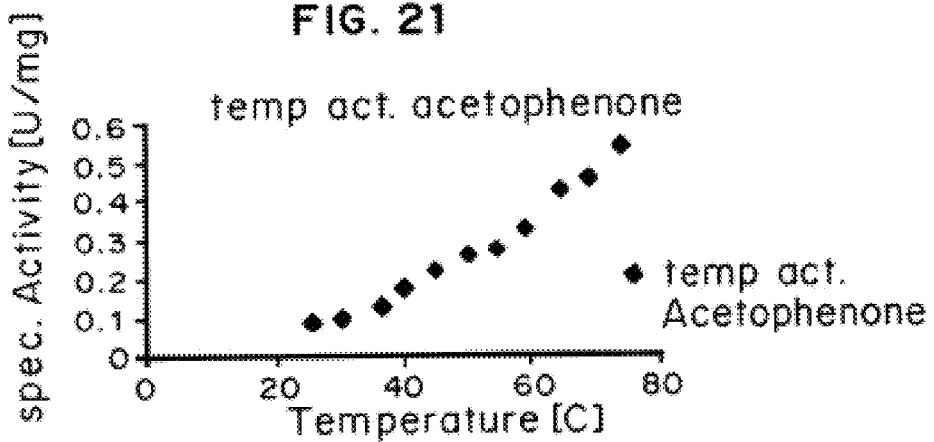
FIGS. 22A and 22B are scatter plots showing the results of a temperature (° C.) vs. specific activity (U/mg) of C1-AmDH for acetophenone (22A) and pFPA (22B).
Figure 22B:
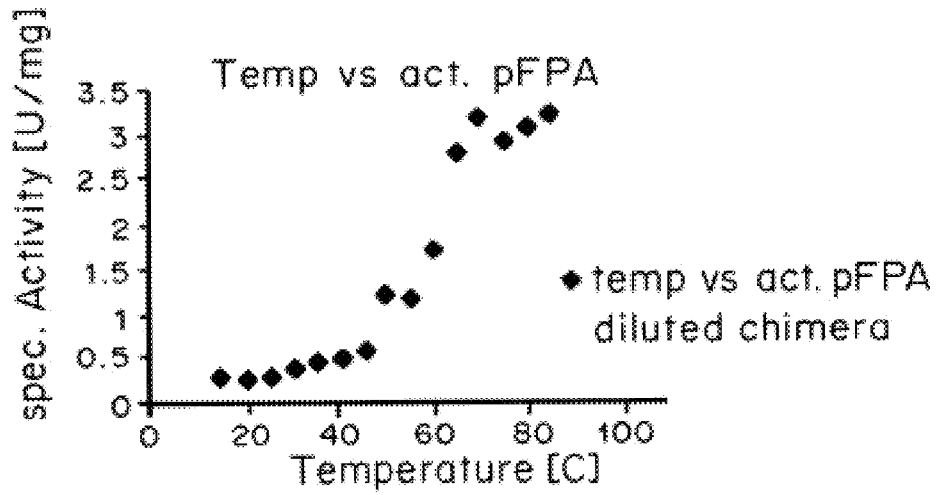

The temperature activity profile was determined over a wide range until the limits of the instrument were reached. The enzyme surprisingly is highly active above 60° C. and did not show any decline of activity up to 80° C. In contrast it is barely active between 20-30° C., so all measurements for activity were determined routinely at 60° C. Product conversions were done at 40° C. and 50° C., due to the temperature limits for regeneration enzyme, FDH. Temperature activity profiles were determined for pFPA and acetophenone (FIGS. 22A and 22B).

The T50 (after 30 min—$T_{50}^{30}$) was also determined for the C1-AmDH. The $T_{50}^{30}$ value was determined to be dependent on the buffer, in PBS, the enzyme was staple for 30 min at 50 C, at 60 C an beyond the enzyme deactivated within the timescale of the experiment. In the presence of 4M ammonium formate buffer we found the $T_{50}^{30}$ value was determined to be at 70 C.

Substrate Conversion Using C1-AmDH and cb-FDH (Formate Dehydrogenase from *Candida boidinii*)

Product formation was characterized for two substrates. The test assay utilized the C1-AmDH in 24 h conversion at 40° C. with cofactor regeneration in a biphasic solvent system with heptane as the organic layer and 5 M ammonium formate as the aqueous layer. Conversions were also carried out at 50° C., which is the upper limit for the cofactor regeneration enzyme FDH.

Figure 23:
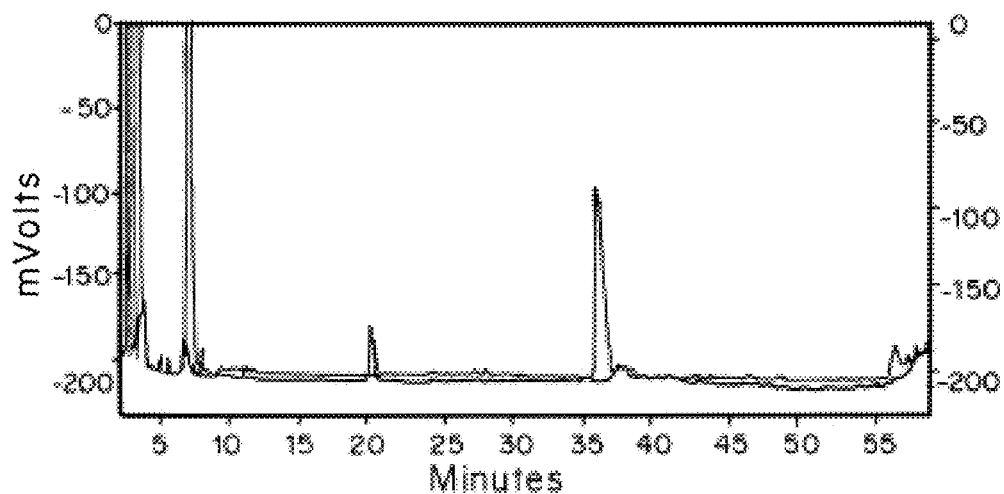
FIG. 23 is a gas chromatogram for 2 positive examples of product formation (methlybenzylamine and p-fluorophenyl-propylamine) after 24 hours of conversion.

FIG. 23 shows product formation for methylbenzylamine and p-fluorophenylproplyamin, and methylcyclohexanone, which shows no product. This is not a quantitative evaluation, since amines are more water soluble than their ketone counterparts and only the organic layer was used for chiral gas chromatography (GC). The peaks were compared to the corresponding standard amines and both determined to be R-specific (FIGS. 24A and 24B).

Figure 24A:
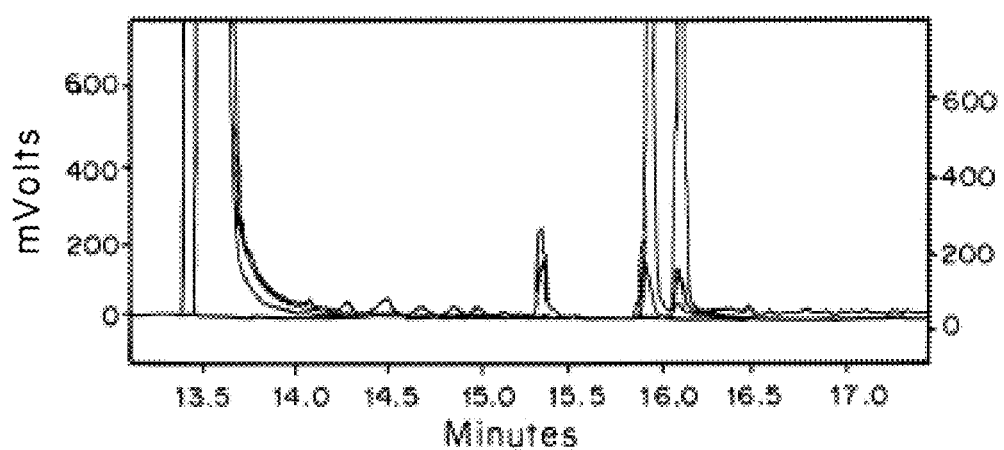
FIGS. 24A and 24B are gas chromatograms.
Figure 24B:
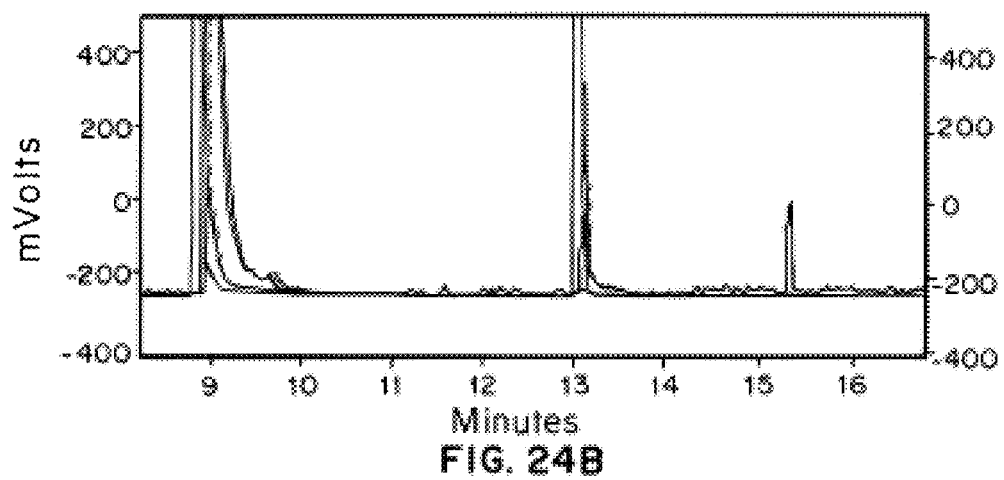

FIGS. 24A and 24B show comparison of product formation using C1-AmDH with racemic amines using chiral GC. FIG. 24A shows production of adamanthlethylamine, a 16 hr conversion with C1-AmDH/FDH system, led to one peak that overlaid with the second of the peaks from the racemic standard resolved on chiral GC, believed to be (R)-configured. FIG. 24B shows production of methylbenzylamine, a 16 hr conversion with C1-AmDH/FDH system, led to one peak overlaying with R-methylbenzylamine.

Summary

These chimeric amine dehydrogenases exhibit new properties, e.g. the C1-AmDH is active on benzylic carbonyls (carbonyl groups in α-position to aromatic rings) such as acetophenone (specific activity 0.3 U/mg) to convert them into chiral amines, a feature none of the previous AmDHs have, as well as other substrates both not active and already active with other AmDH enzymes, such as dibenzylketone (spec. act. 1.39 U/mg). 1-tetralone (0.1 U/mg); and as an example for substrates active with other AmDH enzymes, p-fluorophenylacetone (spec. act, 1.7 U/mg). Another feature of this new class of amine dehydrogenases is their temperature-activity profile. The chimertic enzymes are highly active at temperatures between 50-70° C., similar to known thermostable dehydrogenases from thermophilic bacterial sources.

We claim:

1. A recombinant amine dehydrogenase comprising an amino acid sequence with at least 90% sequence identity to SEQ ID NO:2, wherein the recombinant amine dehydrogenase catalyzes the formation of a chiral amine product.

2. The recombinant amine dehydrogenase of claim 1 comprising SEQ ID NO:2.

3. The recombinant amine dehydrogenase of claim 1 consisting of SEQ ID NO:2.

4. A method of making a chiral amine comprising reacting a substrate with an effective amount the amine dehydrogenase of claim 1 in a reaction mixture comprising a cofactor to produce a chiral amine.

5. The method of claim 4 wherein the cofactor is NADH.

6. The method of claim 5 wherein reaction mixture further comprises glucose and glucose dehydrogenase (GDH) or formate and formate dehydrogenase (FDH).

7. The method of claim 6 wherein the reaction mixture further comprises an organic solvent.

8. The method of claim 7 wherein the solvent is acetone.

9. The method of claim 4 wherein the reaction is carried out by whole cell catalysis.

10. The method of claim 4 wherein the reaction is carried out in an enzyme membrane reactor.

11. The method of any of claim 4 wherein the substrate is a methylketone.

12. The method of claim 11 wherein the methylketone is selected from the group consisting of PFPA, phenoxy-2-propanone, 2-hexanone, methyl isobutyl ketone and 3-methyl-2-butanone.

* * * * *

SEQUENCE LISTING

```
<160> NUMBER OF SEQ ID NOS: 64

<210> SEQ ID NO 1
<211> LENGTH: 379
<212> TYPE: PRT
<213> ORGANISM: Bacillus badius

<400> SEQUENCE: 1

Ser Leu Val Glu Lys Thr Ser Ile Ile Lys Asp Phe Thr Leu Phe Glu
1               5                   10                  15

Lys Met Ser Glu His Glu Gln Val Val Phe Cys Asn Asp Pro Ala Thr
            20                  25                  30

Gly Leu Arg Ala Ile Ile Ala Ile His Asp Thr Thr Leu Gly Pro Ala
        35                  40                  45

Leu Gly Gly Cys Arg Met Gln Pro Tyr Asn Ser Val Glu Glu Ala Leu
    50                  55                  60

Glu Asp Ala Leu Arg Leu Ser Lys Gly Met Thr Tyr Lys Cys Ala Ala
65                  70                  75                  80

Ser Asp Val Asp Phe Gly Gly Gly Lys Ala Val Ile Ile Gly Asp Pro
                85                  90                  95

Gln Lys Asp Lys Ser Pro Glu Leu Phe Arg Ala Phe Gly Gln Phe Val
            100                 105                 110

Asp Ser Leu Gly Gly Arg Phe Tyr Thr Gly Thr Asp Met Gly Thr Asn
        115                 120                 125

Met Glu Asp Phe Ile His Ala Met Lys Glu Thr Asn Cys Ile Val Gly
```

```
                        130                 135                 140
Val Pro Glu Ala Tyr Gly Gly Gly Asp Ser Ser Ile Pro Thr Ala
145                 150                 155                 160

Met Gly Val Leu Tyr Gly Ile Lys Ala Thr Asn Lys Met Leu Phe Gly
                165                 170                 175

Lys Asp Asp Leu Gly Gly Val Thr Tyr Ala Ile Gln Gly Leu Gly Lys
            180                 185                 190

Val Gly Tyr Lys Val Ala Glu Gly Leu Leu Glu Gly Ala His Leu
                195                 200                 205

Phe Val Thr Asp Ile Asn Glu Gln Thr Leu Glu Ala Ile Gln Glu Lys
            210                 215                 220

Ala Lys Thr Thr Ser Gly Ser Val Thr Val Ala Ser Asp Glu Ile
225                 230                 235                 240

Tyr Ser Gln Glu Ala Asp Val Phe Val Pro Cys Ala Phe Gly Gly Val
                245                 250                 255

Val Asn Asp Glu Thr Met Lys Gln Phe Lys Val Lys Ala Ile Ala Gly
            260                 265                 270

Ser Ala Asn Asn Gln Leu Leu Thr Glu Asp His Gly Arg His Leu Ala
            275                 280                 285

Asp Lys Gly Ile Leu Tyr Ala Pro Asp Tyr Ile Val Asn Ser Gly Gly
290                 295                 300

Leu Ile Gln Val Ala Asp Glu Leu Tyr Glu Val Asn Lys Glu Arg Val
305                 310                 315                 320

Leu Ala Lys Thr Lys His Ile Tyr Asp Ala Ile Leu Glu Val Tyr Gln
                325                 330                 335

Gln Ala Glu Leu Asp Gln Ile Thr Thr Met Glu Ala Ala Asn Arg Met
                340                 345                 350

Cys Glu Gln Arg Met Ala Ala Arg Gly Arg Arg Asn Ser Phe Phe Thr
                355                 360                 365

Ser Ser Val Lys Pro Lys Trp Asp Ile Arg Asn
            370                 375

<210> SEQ ID NO 2
<211> LENGTH: 379
<212> TYPE: PRT
<213> ORGANISM: Artificial Sequence
<220> FEATURE:
<223> OTHER INFORMATION: synthesized polypeptide

<400> SEQUENCE: 2

Ser Leu Val Glu Lys Thr Ser Ile Ile Lys Asp Phe Thr Leu Phe Glu
1               5                   10                  15

Lys Met Ser Glu His Glu Gln Val Val Phe Cys Asn Asp Pro Ala Thr
                20                  25                  30

Gly Leu Arg Ala Ile Ile Ala Ile His Asp Thr Thr Leu Gly Pro Ala
            35                  40                  45

Leu Gly Gly Cys Arg Met Gln Pro Tyr Asn Ser Val Glu Glu Ala Leu
        50                  55                  60

Glu Asp Ala Leu Arg Leu Ser Lys Gly Met Thr Tyr Ser Cys Ala Ala
65                  70                  75                  80

Ser Asp Val Asp Phe Gly Gly Lys Ala Val Ile Ile Gly Asp Pro
                85                  90                  95

Gln Lys Asp Lys Ser Pro Glu Leu Phe Arg Ala Phe Gly Gln Phe Val
            100                 105                 110

Asp Ser Leu Gly Gly Arg Phe Tyr Thr Gly Thr Asp Met Gly Thr Asn
```

```
              115                 120                 125
Met Glu Asp Phe Ile His Ala Met Lys Glu Thr Asn Cys Ile Val Gly
        130                 135                 140

Val Pro Glu Ala Tyr Gly Gly Gly Asp Ser Ser Ile Pro Thr Ala
145                 150                 155                 160

Met Gly Val Leu Tyr Gly Ile Lys Ala Thr Asn Lys Met Leu Phe Gly
                165                 170                 175

Lys Asp Asp Leu Gly Gly Val Thr Tyr Ala Ile Gln Gly Leu Gly Lys
            180                 185                 190

Val Gly Tyr Lys Val Ala Glu Gly Leu Leu Glu Glu Gly Ala His Leu
        195                 200                 205

Phe Val Thr Asp Ile Asn Glu Gln Thr Leu Glu Ala Ile Gln Glu Lys
    210                 215                 220

Ala Lys Thr Thr Ser Gly Ser Val Thr Val Ala Ser Asp Glu Ile
225                 230                 235                 240

Tyr Ser Gln Glu Ala Asp Val Phe Val Pro Cys Ala Phe Gly Gly Val
                245                 250                 255

Val Asn Asp Glu Thr Met Lys Gln Phe Lys Val Lys Ala Ile Ala Gly
            260                 265                 270

Ser Ala Asn Leu Gln Leu Leu Thr Glu Asp His Gly Arg His Leu Ala
        275                 280                 285

Asp Lys Gly Ile Leu Tyr Ala Pro Asp Tyr Ile Val Asn Ser Gly Gly
    290                 295                 300

Leu Ile Gln Val Ala Asp Glu Leu Tyr Glu Val Asn Lys Glu Arg Val
305                 310                 315                 320

Leu Ala Lys Thr Lys His Ile Tyr Asp Ala Ile Leu Glu Val Tyr Gln
                325                 330                 335

Gln Ala Glu Leu Asp Gln Ile Thr Thr Met Glu Ala Ala Asn Arg Met
            340                 345                 350

Cys Glu Gln Arg Met Ala Ala Arg Gly Arg Arg Asn Ser Phe Phe Thr
        355                 360                 365

Ser Ser Val Lys Pro Lys Trp Asp Ile Arg Asn
    370                 375

<210> SEQ ID NO 3
<211> LENGTH: 379
<212> TYPE: PRT
<213> ORGANISM: Artificial Sequence
<220> FEATURE:
<223> OTHER INFORMATION: synthesized polypeptide

<400> SEQUENCE: 3

Ser Leu Val Glu Lys Thr Ser Ile Ile Lys Asp Phe Thr Leu Phe Glu
1               5                   10                  15

Lys Met Ser Glu His Glu Gln Val Val Phe Cys Asn Asp Pro Ala Thr
            20                  25                  30

Gly Leu Arg Ala Ile Ile Ala Ile His Asp Thr Thr Leu Gly Pro Ala
        35                  40                  45

Leu Gly Gly Cys Arg Met Gln Pro Tyr Asn Ser Val Glu Glu Ala Leu
    50                  55                  60

Glu Asp Ala Leu Arg Leu Ser Lys Gly Met Thr Tyr Trp Cys Ala Ala
65                  70                  75                  80

Ser Asp Val Asp Phe Gly Gly Gly Lys Ala Val Ile Ile Gly Asp Pro
                85                  90                  95

Gln Lys Asp Lys Ser Pro Glu Leu Phe Arg Ala Phe Gly Gln Phe Val
```

```
            100                 105                 110
Asp Ser Leu Gly Gly Arg Phe Tyr Thr Gly Thr Asp Met Gly Thr Asn
            115                 120                 125

Met Glu Asp Phe Ile His Ala Met Lys Glu Thr Asn Cys Ile Val Gly
            130                 135             140

Val Pro Glu Ala Tyr Gly Gly Gly Asp Ser Ser Ile Pro Thr Ala
145                 150                 155                 160

Met Gly Val Leu Tyr Gly Ile Lys Ala Thr Asn Lys Met Leu Phe Gly
                165                 170                 175

Lys Asp Asp Leu Gly Gly Val Thr Tyr Ala Ile Gln Gly Leu Gly Lys
            180                 185                 190

Val Gly Tyr Lys Val Ala Glu Gly Leu Leu Glu Glu Gly Ala His Leu
            195                 200                 205

Phe Val Thr Asp Ile Asn Glu Gln Thr Leu Glu Ala Ile Gln Glu Lys
            210                 215                 220

Ala Lys Thr Thr Ser Gly Ser Val Thr Val Ala Ser Asp Glu Ile
225                 230                 235                 240

Tyr Ser Gln Glu Ala Asp Val Phe Val Pro Cys Ala Phe Gly Gly Val
                245                 250                 255

Val Asn Asp Glu Thr Met Lys Gln Phe Lys Val Lys Ala Ile Ala Gly
            260                 265                 270

Ser Ala Asn Glu Gln Leu Leu Thr Glu Asp His Gly Arg His Leu Ala
            275                 280                 285

Asp Lys Gly Ile Leu Tyr Ala Pro Asp Tyr Ile Val Asn Ser Gly Gly
            290                 295                 300

Leu Ile Gln Val Ala Asp Glu Leu Tyr Glu Val Asn Lys Glu Arg Val
305                 310                 315                 320

Leu Ala Lys Thr Lys His Ile Tyr Asp Ala Ile Leu Glu Val Tyr Gln
                325                 330                 335

Gln Ala Glu Leu Asp Gln Ile Thr Thr Met Glu Ala Ala Asn Arg Met
            340                 345                 350

Cys Glu Gln Arg Met Ala Ala Arg Gly Arg Arg Asn Ser Phe Phe Thr
            355                 360                 365

Ser Ser Val Lys Pro Lys Trp Asp Ile Arg Asn
            370                 375

<210> SEQ ID NO 4
<211> LENGTH: 366
<212> TYPE: PRT
<213> ORGANISM: Bacillus stearothermophilus

<400> SEQUENCE: 4

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Val Ile His Asp
                20                  25                  30

Thr Thr Leu Gly Pro Ala Leu Gly Gly Thr Arg Met Trp Met Tyr Asn
            35                  40                  45

Ser Glu Glu Glu Ala Leu Glu Asp Ala Leu Arg Leu Ala Arg Gly Met
        50                  55                  60

Thr Tyr Lys Asn Ala Ala Ala Gly Leu Asn Leu Gly Gly Gly Lys Thr
65              70                  75                  80

Val Ile Ile Gly Asp Pro Arg Lys Asp Lys Asn Glu Ala Met Phe Arg
                85                  90                  95
```

Ala Phe Gly Arg Phe Ile Gln Gly Leu Asn Gly Arg Tyr Ile Thr Ala
            100                 105                 110

Glu Asp Val Gly Thr Thr Val Ala Asp Met Asp Ile Ile Tyr Gln Glu
        115                 120                 125

Thr Asp Tyr Val Thr Gly Ile Ser Pro Glu Phe Gly Ser Ser Gly Asn
    130                 135                 140

Pro Ser Pro Ala Thr Ala Tyr Gly Val Tyr Arg Gly Met Lys Ala Ala
145                 150                 155                 160

Ala Lys Glu Ala Phe Gly Ser Asp Ser Leu Glu Gly Lys Val Val Ala
                165                 170                 175

Val Gln Gly Val Gly Asn Val Ala Tyr His Leu Cys Arg His Leu His
            180                 185                 190

Glu Glu Gly Ala Lys Leu Ile Val Thr Asp Ile Asn Lys Glu Ala Val
        195                 200                 205

Ala Arg Ala Val Glu Glu Phe Gly Ala Lys Ala Val Asp Pro Asn Asp
    210                 215                 220

Ile Tyr Gly Val Glu Cys Asp Ile Phe Ala Pro Cys Ala Leu Gly Gly
225                 230                 235                 240

Ile Ile Asn Asp Gln Thr Ile Pro Gln Leu Lys Ala Lys Val Ile Ala
                245                 250                 255

Gly Ser Ala Asp Asn Gln Leu Lys Glu Pro Arg His Gly Asp Met Ile
            260                 265                 270

His Glu Met Gly Ile Val Tyr Ala Pro Asp Tyr Val Ile Asn Ala Gly
        275                 280                 285

Gly Val Ile Asn Val Ala Asp Glu Leu Tyr Gly Tyr Asn Arg Glu Arg
    290                 295                 300

Ala Met Lys Lys Ile Glu Gln Ile Tyr Asp Asn Ile Glu Lys Val Phe
305                 310                 315                 320

Ala Ile Ala Lys Arg Asp Asn Ile Pro Thr Tyr Val Ala Ala Asp Arg
                325                 330                 335

Met Ala Glu Glu Arg Ile Glu Thr Met Arg Lys Ala Arg Ser Gln Phe
            340                 345                 350

Leu Gln Asn Gly His His Ile Leu Ser Arg Arg Arg Ala Arg
        355                 360                 365

<210> SEQ ID NO 5
<211> LENGTH: 366
<212> TYPE: PRT
<213> ORGANISM: Artificial Sequence
<220> FEATURE:
<223> OTHER INFORMATION: synthesized polypeptide

<400> SEQUENCE: 5

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Ile Val Ile His Asp
                20                  25                  30

Thr Thr Leu Gly Pro Ala Leu Gly Gly Thr Arg Met Trp Met Tyr Asn
            35                  40                  45

Ser Glu Glu Glu Ala Leu Glu Asp Ala Leu Arg Leu Ala Arg Gly Met
        50                  55                  60

Thr Tyr Met Asn Ala Ala Ala Gly Leu Asn Leu Gly Gly Gly Lys Thr
65                  70                  75                  80

Val Ile Ile Gly Asp Pro Arg Lys Asp Lys Asn Glu Ala Met Phe Arg
                85                  90                  95

```
Ala Phe Gly Arg Phe Ile Gln Gly Leu Asn Gly Arg Tyr Ile Thr Ala
                100                 105                 110

Val Asp Val Gly Thr Thr Val Ala Asp Met Asp Ile Ile Tyr Gln Glu
            115                 120                 125

Thr Asp Tyr Val Thr Gly Ile Ser Pro Glu Phe Gly Ser Ser Gly Asn
        130                 135                 140

Pro Ser Pro Ala Thr Ala Tyr Gly Val Tyr Arg Gly Met Lys Ala Ala
145                 150                 155                 160

Ala Lys Glu Ala Phe Gly Ser Asp Ser Leu Glu Gly Lys Val Val Ala
                165                 170                 175

Val Gln Gly Val Gly Asn Val Ala Tyr His Leu Cys Arg His Leu His
            180                 185                 190

Glu Glu Gly Ala Lys Leu Ile Val Thr Asp Ile Asn Lys Glu Ala Val
        195                 200                 205

Ala Arg Ala Val Glu Glu Phe Gly Ala Lys Ala Val Asp Pro Asn Asp
210                 215                 220

Ile Tyr Gly Val Glu Cys Asp Ile Phe Ala Pro Cys Ala Leu Gly Gly
225                 230                 235                 240

Ile Ile Asn Asp Gln Thr Ile Pro Gln Leu Lys Ala Lys Val Ile Ala
                245                 250                 255

Gly Ser Ala Asp Asn Gln Leu Lys Glu Pro Arg His Gly Asp Met Ile
            260                 265                 270

His Glu Met Gly Ile Val Tyr Ala Pro Asp Tyr Val Ile Asn Ala Gly
        275                 280                 285

Gly Val Ile Asn Val Ala Asp Glu Leu Tyr Gly Tyr Asn Arg Glu Arg
290                 295                 300

Ala Met Lys Lys Ile Glu Gln Ile Tyr Asp Asn Ile Glu Lys Val Phe
305                 310                 315                 320

Ala Ile Ala Lys Arg Asp Asn Ile Pro Thr Tyr Val Ala Ala Asp Arg
                325                 330                 335

Met Ala Glu Glu Arg Ile Glu Thr Met Arg Lys Ala Arg Ser Gln Phe
            340                 345                 350

Leu Gln Asn Gly His His Ile Leu Ser Arg Arg Arg Ala Arg
        355                 360                 365

<210> SEQ ID NO 6
<211> LENGTH: 366
<212> TYPE: PRT
<213> ORGANISM: Artificial Sequence
<220> FEATURE:
<223> OTHER INFORMATION: synthesized polypeptide

<400> SEQUENCE: 6

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Ile Val Ile His Asp
            20                  25                  30

Thr Thr Leu Gly Pro Ala Leu Gly Gly Thr Arg Met Trp Met Tyr Asn
        35                  40                  45

Ser Glu Glu Glu Ala Leu Glu Asp Ala Leu Arg Leu Ala Arg Gly Met
    50                  55                  60

Thr Tyr Met Asn Ala Ala Ala Gly Leu Asn Leu Gly Gly Gly Lys Thr
65                  70                  75                  80

Val Ile Ile Gly Asp Pro Arg Lys Asp Lys Asn Glu Ala Met Phe Arg
                85                  90                  95
```

Ala Phe Gly Arg Phe Ile Gln Gly Leu Asn Gly Arg Tyr Ile Thr Ala
            100                 105                 110

Val Asp Val Gly Thr Thr Val Ala Asp Met Asp Ile Ile Tyr Gln Glu
        115                 120                 125

Thr Asp Tyr Val Thr Gly Ile Ser Pro Glu Phe Gly Ser Ser Gly Asn
    130                 135                 140

Pro Ser Pro Ala Thr Ala Tyr Gly Val Tyr Arg Gly Met Lys Ala Ala
145                 150                 155                 160

Ala Lys Glu Ala Phe Gly Ser Asp Ser Leu Glu Gly Lys Val Val Ala
                165                 170                 175

Val Gln Gly Val Gly Asn Val Ala Tyr His Leu Cys Arg His Leu His
            180                 185                 190

Glu Glu Gly Ala Lys Leu Ile Val Thr Asp Ile Asn Lys Glu Ala Val
        195                 200                 205

Ala Arg Ala Val Glu Glu Phe Gly Ala Lys Ala Val Asp Pro Asn Asp
    210                 215                 220

Ile Tyr Gly Val Glu Cys Asp Ile Phe Ala Pro Cys Ala Leu Gly Gly
225                 230                 235                 240

Ile Ile Asn Asp Gln Thr Ile Pro Gln Leu Lys Ala Lys Val Ile Ala
                245                 250                 255

Gly Ser Ala Asp Val Gln Leu Lys Glu Pro Arg His Gly Asp Met Ile
            260                 265                 270

His Glu Met Gly Ile Val Tyr Ala Pro Asp Tyr Val Ile Asn Ala Gly
        275                 280                 285

Gly Val Ile Asn Val Ala Asp Glu Leu Tyr Gly Tyr Asn Arg Glu Arg
    290                 295                 300

Ala Met Lys Lys Ile Glu Gln Ile Tyr Asp Asn Ile Glu Lys Val Phe
305                 310                 315                 320

Ala Ile Ala Lys Arg Asp Asn Ile Pro Thr Tyr Val Ala Ala Asp Arg
                325                 330                 335

Met Ala Glu Glu Arg Ile Glu Thr Met Arg Lys Ala Arg Ser Gln Phe
            340                 345                 350

Leu Gln Asn Gly His His Ile Leu Ser Arg Arg Arg Ala Arg
    355                 360                 365

<210> SEQ ID NO 7
<211> LENGTH: 366
<212> TYPE: PRT
<213> ORGANISM: Artificial Sequence
<220> FEATURE:
<223> OTHER INFORMATION: synthesized polypeptide

<400> SEQUENCE: 7

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Val Ile His Asp
            20                  25                  30

Thr Thr Leu Gly Pro Ala Leu Gly Gly Thr Arg Met Trp Met Tyr Asn
        35                  40                  45

Ser Glu Glu Glu Ala Leu Glu Asp Ala Leu Arg Leu Ala Arg Gly Met
    50                  55                  60

Thr Tyr Met Asn Ala Ala Ala Gly Leu Asn Leu Gly Gly Gly Lys Thr
65                  70                  75                  80

Val Ile Ile Gly Asp Pro Arg Lys Asp Lys Asn Glu Ala Met Phe Arg
                85                  90                  95

Ala Phe Gly Arg Phe Ile Gln Gly Leu Asn Gly Arg Tyr Ile Thr Ala
            100                 105                 110

Val Asp Val Gly Thr Thr Val Ala Asp Met Asp Ile Ile Tyr Gln Glu
        115                 120                 125

Thr Asp Tyr Val Thr Gly Ile Ser Pro Glu Phe Gly Ser Ser Gly Asn
    130                 135                 140

Pro Ser Pro Ala Thr Ala Tyr Gly Val Tyr Arg Gly Met Lys Ala Ala
145                 150                 155                 160

Ala Lys Glu Ala Phe Gly Ser Asp Ser Leu Glu Gly Lys Val Val Ala
                165                 170                 175

Val Gln Gly Val Gly Asn Val Ala Tyr His Leu Cys Arg His Leu His
            180                 185                 190

Glu Glu Gly Ala Lys Leu Ile Val Thr Asp Ile Asn Lys Glu Ala Val
        195                 200                 205

Ala Arg Ala Val Glu Glu Phe Gly Ala Lys Ala Val Asp Pro Asn Asp
    210                 215                 220

Ile Tyr Gly Val Glu Cys Asp Ile Phe Ala Pro Cys Ala Leu Gly Gly
225                 230                 235                 240

Ile Ile Asn Asp Gln Thr Ile Pro Gln Leu Lys Ala Lys Val Ile Ala
                245                 250                 255

Gly Ser Ala Asp Cys Gln Leu Lys Glu Pro Arg His Gly Asp Met Ile
            260                 265                 270

His Glu Met Gly Ile Val Tyr Ala Pro Asp Tyr Val Ile Asn Ala Gly
        275                 280                 285

Gly Val Ile Asn Val Ala Asp Glu Leu Tyr Gly Tyr Asn Arg Glu Arg
    290                 295                 300

Ala Met Lys Lys Ile Glu Gln Ile Tyr Asp Asn Ile Glu Lys Val Phe
305                 310                 315                 320

Ala Ile Ala Lys Arg Asp Asn Ile Pro Thr Tyr Val Ala Ala Asp Arg
                325                 330                 335

Met Ala Glu Glu Arg Ile Glu Thr Met Arg Lys Ala Arg Ser Gln Phe
            340                 345                 350

Leu Gln Asn Gly His His Ile Leu Ser Arg Arg Arg Ala Arg
        355                 360                 365

<210> SEQ ID NO 8
<211> LENGTH: 366
<212> TYPE: PRT
<213> ORGANISM: Artificial Sequence
<220> FEATURE:
<223> OTHER INFORMATION: synthesized polypeptide

<400> SEQUENCE: 8

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Ile Val Ile His Asp
            20                  25                  30

Thr Thr Leu Gly Pro Ala Leu Gly Gly Thr Arg Met Trp Met Tyr Asn
        35                  40                  45

Ser Glu Glu Glu Ala Leu Glu Asp Ala Leu Arg Leu Ala Arg Gly Met
    50                  55                  60

Thr Tyr Met Asn Ala Ala Ala Gly Leu Asn Leu Gly Gly Gly Lys Thr
65                  70                  75                  80

Val Ile Ile Gly Asp Pro Arg Lys Asp Lys Asn Glu Ala Met Phe Arg
                85                  90                  95

Ala Phe Gly Arg Phe Ile Gln Gly Leu Asn Gly Arg Tyr Ile Thr Ala
            100                 105                 110

Val Asp Val Gly Thr Thr Val Ala Asp Met Asp Ile Ile Tyr Gln Glu
        115                 120                 125

Thr Asp Tyr Val Thr Gly Ile Ser Pro Glu Phe Gly Ser Ser Gly Asn
    130                 135                 140

Pro Ser Pro Ala Thr Ala Tyr Gly Val Tyr Arg Gly Met Lys Ala Ala
145                 150                 155                 160

Ala Lys Glu Ala Phe Gly Ser Asp Ser Leu Glu Gly Lys Val Val Ala
                165                 170                 175

Val Gln Gly Val Gly Asn Val Ala Tyr His Leu Cys Arg His Leu His
            180                 185                 190

Glu Glu Gly Ala Lys Leu Ile Val Thr Asp Ile Asn Lys Glu Ala Val
        195                 200                 205

Ala Arg Ala Val Glu Glu Phe Gly Ala Lys Ala Val Asp Pro Asn Asp
    210                 215                 220

Ile Tyr Gly Val Glu Cys Asp Ile Phe Ala Pro Cys Ala Leu Gly Gly
225                 230                 235                 240

Ile Ile Asn Asp Gln Thr Ile Pro Gln Leu Lys Ala Lys Val Ile Ala
                245                 250                 255

Gly Ser Ala Asp Val Gln Leu Lys Glu Pro Arg His Gly Asp Met Ile
            260                 265                 270

His Glu Met Gly Ile Val Tyr Ala Pro Asp Tyr Val Ile Asn Ala Gly
        275                 280                 285

Gly Cys Ile Asn Val Ala Asp Glu Leu Tyr Gly Tyr Asn Arg Glu Arg
    290                 295                 300

Ala Met Lys Lys Ile Glu Gln Ile Tyr Asp Asn Ile Glu Lys Val Phe
305                 310                 315                 320

Ala Ile Ala Lys Arg Asp Asn Ile Pro Thr Tyr Val Ala Ala Asp Arg
                325                 330                 335

Met Ala Glu Glu Arg Ile Glu Thr Met Arg Lys Ala Arg Ser Gln Phe
            340                 345                 350

Leu Gln Asn Gly His His Ile Leu Ser Arg Arg Arg Ala Arg
        355                 360                 365

<210> SEQ ID NO 9
<211> LENGTH: 366
<212> TYPE: PRT
<213> ORGANISM: Artificial Sequence
<220> FEATURE:
<223> OTHER INFORMATION: synthesized polypeptide

<400> SEQUENCE: 9

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Val Ile His Asp
            20                  25                  30

Thr Thr Leu Gly Pro Ala Leu Gly Gly Thr Arg Met Trp Met Tyr Asn
        35                  40                  45

Ser Glu Glu Glu Ala Leu Glu Asp Ala Leu Arg Leu Ala Arg Gly Met
    50                  55                  60

Thr Tyr Met Asn Ala Ala Ala Gly Leu Asn Leu Gly Gly Gly Lys Thr
65                  70                  75                  80

Val Ile Ile Gly Asp Pro Arg Lys Asp Lys Asn Glu Ala Met Phe Arg
                85                  90                  95

```
Ala Phe Gly Arg Phe Ile Gln Gly Leu Asn Gly Arg Tyr Ile Thr Ala
            100                 105                 110

Val Asp Val Gly Thr Thr Val Ala Asp Met Asp Ile Ile Tyr Gln Glu
            115                 120                 125

Thr Asp Tyr Val Thr Gly Ile Ser Pro Glu Phe Gly Ser Ser Gly Asn
        130                 135                 140

Pro Ser Pro Ala Thr Ala Tyr Gly Val Tyr Arg Gly Met Lys Ala Ala
145                 150                 155                 160

Ala Lys Glu Ala Phe Gly Ser Asp Ser Leu Glu Gly Lys Val Val Ala
                165                 170                 175

Val Gln Gly Val Gly Asn Val Ala Tyr His Leu Cys Arg His Leu His
            180                 185                 190

Glu Glu Gly Ala Lys Leu Ile Val Thr Asp Ile Asn Lys Glu Ala Val
            195                 200                 205

Ala Arg Ala Val Glu Glu Phe Gly Ala Lys Ala Val Asp Pro Asn Asp
        210                 215                 220

Ile Tyr Gly Val Glu Cys Asp Ile Phe Ala Pro Cys Ala Leu Gly Gly
225                 230                 235                 240

Ile Ile Asn Asp Gln Thr Ile Pro Gln Leu Lys Ala Lys Val Ile Ala
                245                 250                 255

Gly Ser Ala Asp Cys Gln Leu Lys Glu Pro Arg His Gly Asp Met Ile
            260                 265                 270

His Glu Met Gly Ile Val Tyr Ala Pro Asp Tyr Val Ile Asn Ala Gly
            275                 280                 285

Gly Cys Ile Asn Val Ala Asp Glu Leu Tyr Gly Tyr Asn Arg Glu Arg
        290                 295                 300

Ala Met Lys Lys Ile Glu Gln Ile Tyr Asp Asn Ile Glu Lys Val Phe
305                 310                 315                 320

Ala Ile Ala Lys Arg Asp Asn Ile Pro Thr Tyr Val Ala Ala Asp Arg
                325                 330                 335

Met Ala Glu Glu Arg Ile Glu Thr Met Arg Lys Ala Arg Ser Gln Phe
            340                 345                 350

Leu Gln Asn Gly His His Ile Leu Ser Arg Arg Ala Arg
        355                 360                 365

<210> SEQ ID NO 10
<211> LENGTH: 366
<212> TYPE: PRT
<213> ORGANISM: Artificial Sequence
<220> FEATURE:
<223> OTHER INFORMATION: synthesized polypeptide

<400> SEQUENCE: 10

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Val Ile His Asp
                20                  25                  30

Thr Thr Leu Gly Pro Ala Leu Gly Gly Thr Arg Met Trp Met Tyr Asn
            35                  40                  45

Ser Glu Glu Glu Ala Leu Glu Asp Ala Leu Arg Leu Ala Arg Gly Ser
    50                  55                  60

Thr Tyr Met Asn Ala Ala Ala Gly Leu Asn Leu Gly Gly Gly Lys Thr
65                  70                  75                  80

Val Ile Ile Gly Asp Pro Arg Lys Asp Lys Asn Glu Ala Met Phe Arg
                85                  90                  95
```

```
Ala Phe Gly Arg Phe Ile Gln Gly Leu Asn Gly Arg Tyr Ile Thr Ala
                100                 105                 110

Val Asp Val Gly Thr Thr Val Ala Asp Met Asp Ile Ile Tyr Gln Glu
            115                 120                 125

Thr Asp Tyr Val Thr Gly Ile Ser Pro Glu Phe Gly Ser Ser Gly Asn
        130                 135                 140

Pro Ser Pro Ala Thr Ala Tyr Gly Val Tyr Arg Gly Met Lys Ala Ala
145                 150                 155                 160

Ala Lys Glu Ala Phe Gly Ser Asp Ser Leu Glu Gly Lys Val Val Ala
                165                 170                 175

Val Gln Gly Val Gly Asn Val Ala Tyr His Leu Cys Arg His Leu His
            180                 185                 190

Glu Glu Gly Ala Lys Leu Ile Val Thr Asp Ile Asn Lys Glu Ala Val
        195                 200                 205

Ala Arg Ala Val Glu Glu Phe Gly Ala Lys Ala Val Asp Pro Asn Asp
210                 215                 220

Ile Tyr Gly Val Glu Cys Asp Ile Phe Ala Pro Cys Ala Leu Gly Gly
225                 230                 235                 240

Ile Ile Asn Asp Gln Thr Ile Pro Gln Leu Lys Ala Lys Val Ile Ala
                245                 250                 255

Gly Ser Ala Asp Leu Gln Leu Lys Glu Pro Arg His Gly Asp Met Ile
            260                 265                 270

His Glu Met Gly Ile Val Tyr Ala Pro Asp Tyr Val Ile Asn Ala Gly
        275                 280                 285

Gly Cys Ile Asn Val Ala Asp Glu Leu Tyr Gly Tyr Asn Arg Glu Arg
        290                 295                 300

Ala Met Lys Lys Ile Glu Gln Ile Tyr Asp Asn Ile Glu Lys Val Phe
305                 310                 315                 320

Ala Ile Ala Lys Arg Asp Asn Ile Pro Thr Tyr Val Ala Ala Asp Arg
                325                 330                 335

Met Ala Glu Glu Arg Ile Glu Thr Met Arg Lys Ala Arg Ser Gln Phe
            340                 345                 350

Leu Gln Asn Gly His His Ile Leu Ser Arg Arg Arg Ala Arg
        355                 360                 365

<210> SEQ ID NO 11
<211> LENGTH: 357
<212> TYPE: PRT
<213> ORGANISM: Streptomyces cinnamonensis

<400> SEQUENCE: 11

Thr Glu Ala Asp Asn Gly Val Leu His Thr Leu Phe His Ser Asp Gln
1               5                   10                  15

Gly Gly His Glu Gln Val Val Leu Cys Gln Asp Arg Ala Ser Gly Leu
            20                  25                  30

Lys Ala Val Ile Ala Ile His Ser Thr Ala Leu Gly Pro Ala Leu Gly
        35                  40                  45

Gly Thr Arg Phe Tyr Pro Tyr Ala Thr Glu Glu Ala Val Ala Asp
    50                  55                  60

Val Leu Asn Leu Ser Arg Gly Met Ser Tyr Lys Asn Ala Met Ala Gly
65                  70                  75                  80

Leu Asp His Gly Gly Gly Lys Ala Val Ile Ile Gly Asp Pro Glu Gln
                85                  90                  95

Ile Lys Ser Glu Asp Leu Leu Leu Ala Phe Gly Arg Phe Val Ala Ser
            100                 105                 110
```

Leu Gly Gly Arg Tyr Val Thr Ala Cys Asp Val Gly Thr Tyr Val Ala
        115                 120                 125

Asp Met Asp Val Val Ala Arg Glu Cys Arg Trp Thr Thr Gly Arg Ser
130                 135                 140

Pro Glu Asn Gly Gly Ala Gly Asp Ser Ser Val Leu Thr Ala Phe Gly
145                 150                 155                 160

Val Phe Gln Gly Met Arg Ala Ser Ala Glu His Leu Trp Gly Asp Pro
                165                 170                 175

Ser Leu Arg Gly Arg Lys Val Gly Val Ala Val Gly Lys Val Gly
        180                 185                 190

His His Leu Val Glu His Leu Leu Glu Asp Gly Ala Asp Val Val Ile
        195                 200                 205

Thr Asp Val Arg Glu Glu Ser Val Asn Arg Ser Thr His Lys His Pro
        210                 215                 220

Ser Val Thr Ala Val Ala Asp Thr Glu Ala Leu Ile Arg Thr Glu Gly
225                 230                 235                 240

Leu Asp Ile Tyr Ala Pro Cys Ala Leu Gly Ala Leu Asp Asp Asp
                245                 250                 255

Ser Val Pro Val Leu Thr Ala Lys Val Val Cys Gly Ala Ala Asn Asn
        260                 265                 270

Gln Leu Ala His Pro Gly Val Glu Lys Asp Leu Ala Asp Arg Ser Ile
        275                 280                 285

Leu Tyr Ala Pro Asp Tyr Val Val Asn Ala Gly Val Ile Gln Val
        290                 295                 300

Ala Asp Glu Leu Arg Gly Phe Asp Phe Asp Arg Cys Lys Ala Lys Ala
305                 310                 315                 320

Ser Lys Ile Phe Asp Thr Thr Leu Ala Ile Phe Ala Arg Ala Lys Glu
                325                 330                 335

Asp Gly Ile Pro Pro Ala Ala Ala Asp Arg Ile Ala Glu Gln Arg
                340                 345                 350

Met Ser Asp Ala Arg
        355

<210> SEQ ID NO 12
<211> LENGTH: 357
<212> TYPE: PRT
<213> ORGANISM: Artificial Sequence
<220> FEATURE:
<223> OTHER INFORMATION: synthesized polypeptide

<400> SEQUENCE: 12

Thr Glu Ala Asp Asn Gly Val Leu His Thr Leu Phe His Ser Asp Gln
1               5                   10                  15

Gly Gly His Glu Gln Val Val Leu Cys Gln Asp Arg Ala Ser Gly Leu
                20                  25                  30

Lys Ala Val Ile Ala Ile His Ser Thr Ala Leu Gly Pro Ala Leu Gly
        35                  40                  45

Gly Thr Arg Phe Tyr Pro Tyr Ala Thr Glu Glu Ala Val Ala Asp
        50                  55                  60

Val Leu Asn Leu Ser Arg Gly Met Ser Tyr Ser Asn Ala Met Ala Gly
65                  70                  75                  80

Leu Asp His Gly Gly Gly Lys Ala Val Ile Ile Gly Asp Pro Glu Gln
                85                  90                  95

Ile Lys Ser Glu Asp Leu Leu Leu Ala Phe Gly Arg Phe Val Ala Ser
                100                 105                 110

```
Leu Gly Gly Arg Tyr Val Thr Ala Cys Asp Val Gly Thr Tyr Val Ala
        115                 120                 125

Asp Met Asp Val Val Ala Arg Glu Cys Arg Trp Thr Thr Gly Arg Ser
130                 135                 140

Pro Glu Asn Gly Gly Ala Gly Asp Ser Ser Val Leu Thr Ala Phe Gly
145                 150                 155                 160

Val Phe Gln Gly Met Arg Ala Ser Ala Glu His Leu Trp Gly Asp Pro
                165                 170                 175

Ser Leu Arg Gly Arg Lys Val Gly Val Ala Gly Val Gly Lys Val Gly
            180                 185                 190

His His Leu Val Glu His Leu Leu Glu Asp Gly Ala Asp Val Val Ile
        195                 200                 205

Thr Asp Val Arg Glu Glu Ser Val Asn Arg Ser Thr His Lys His Pro
210                 215                 220

Ser Val Thr Ala Val Ala Asp Thr Glu Ala Leu Ile Arg Thr Glu Gly
225                 230                 235                 240

Leu Asp Ile Tyr Ala Pro Cys Ala Leu Gly Gly Ala Leu Asp Asp Asp
                245                 250                 255

Ser Val Pro Val Leu Thr Ala Lys Val Val Cys Gly Ala Ala Asn Leu
            260                 265                 270

Gln Leu Ala His Pro Gly Val Glu Lys Asp Leu Ala Asp Arg Ser Ile
        275                 280                 285

Leu Tyr Ala Pro Asp Tyr Val Val Asn Ala Gly Gly Val Ile Gln Val
290                 295                 300

Ala Asp Glu Leu Arg Gly Phe Asp Phe Asp Arg Cys Lys Ala Lys Ala
305                 310                 315                 320

Ser Lys Ile Phe Asp Thr Thr Leu Ala Ile Phe Ala Arg Ala Lys Glu
                325                 330                 335

Asp Gly Ile Pro Pro Ala Ala Ala Asp Arg Ile Ala Glu Gln Arg
            340                 345                 350

Met Ser Asp Ala Arg
        355

<210> SEQ ID NO 13
<211> LENGTH: 149
<212> TYPE: PRT
<213> ORGANISM: Artificial Sequence
<220> FEATURE:
<223> OTHER INFORMATION: synthesized polypeptide

<400> SEQUENCE: 13

Ser Leu Val Glu Lys Thr Ser Ile Ile Lys Asp Phe Thr Leu Phe Glu
1               5                   10                  15

Lys Met Ser Glu His Glu Gln Val Val Phe Cys Asn Asp Pro Ala Thr
                20                  25                  30

Gly Leu Arg Ala Ile Ile Ala Ile His Asp Thr Thr Leu Gly Pro Ala
            35                  40                  45

Leu Gly Gly Cys Arg Met Gln Pro Tyr Asn Ser Val Glu Glu Ala Leu
        50                  55                  60

Glu Asp Ala Leu Arg Leu Ser Lys Gly Met Thr Tyr Ser Cys Ala Ala
65                  70                  75                  80

Ser Asp Val Asp Phe Gly Gly Gly Lys Ala Val Ile Ile Gly Asp Pro
                85                  90                  95

Gln Lys Asp Lys Ser Pro Glu Leu Phe Arg Ala Phe Gly Gln Phe Val
            100                 105                 110
```

```
Asp Ser Leu Gly Gly Arg Phe Tyr Thr Gly Thr Asp Met Gly Thr Asn
            115                 120                 125

Met Glu Asp Phe Ile His Ala Met Lys Glu Thr Asn Cys Ile Val Gly
130                 135                 140

Val Pro Glu Ala Tyr
145

<210> SEQ ID NO 14
<211> LENGTH: 230
<212> TYPE: PRT
<213> ORGANISM: Artificial Sequence
<220> FEATURE:
<223> OTHER INFORMATION: synthesized polypeptide

<400> SEQUENCE: 14

Gly Gly Gly Gly Asp Ser Ser Ile Pro Thr Ala Met Gly Val Leu Tyr
1               5                   10                  15

Gly Ile Lys Ala Thr Asn Lys Met Leu Phe Gly Lys Asp Asp Leu Gly
            20                  25                  30

Gly Val Thr Tyr Ala Ile Gln Gly Leu Gly Lys Val Gly Tyr Lys Val
        35                  40                  45

Ala Glu Gly Leu Leu Glu Glu Gly Ala His Leu Phe Val Thr Asp Ile
    50                  55                  60

Asn Glu Gln Thr Leu Glu Ala Ile Gln Glu Lys Ala Lys Thr Thr Ser
65                  70                  75                  80

Gly Ser Val Thr Val Ala Ser Asp Glu Ile Tyr Ser Gln Glu Ala
            85                  90                  95

Asp Val Phe Val Pro Cys Ala Phe Gly Gly Val Val Asn Asp Glu Thr
                100                 105                 110

Met Lys Gln Phe Lys Val Lys Ala Ile Ala Gly Ser Ala Asn Leu Gln
            115                 120                 125

Leu Leu Thr Glu Asp His Gly Arg His Leu Ala Asp Lys Gly Ile Leu
        130                 135                 140

Tyr Ala Pro Asp Tyr Ile Val Asn Ser Gly Gly Leu Ile Gln Val Ala
145                 150                 155                 160

Asp Glu Leu Tyr Glu Val Asn Lys Glu Arg Val Leu Ala Lys Thr Lys
                165                 170                 175

His Ile Tyr Asp Ala Ile Leu Glu Val Tyr Gln Gln Ala Glu Leu Asp
            180                 185                 190

Gln Ile Thr Thr Met Glu Ala Ala Asn Arg Met Cys Glu Gln Arg Met
        195                 200                 205

Ala Ala Arg Gly Arg Arg Asn Ser Phe Phe Thr Ser Ser Val Lys Pro
    210                 215                 220

Lys Trp Asp Ile Arg Asn
225                 230

<210> SEQ ID NO 15
<211> LENGTH: 139
<212> TYPE: PRT
<213> ORGANISM: Artificial Sequence
<220> FEATURE:
<223> OTHER INFORMATION: synthesized polypeptide

<400> SEQUENCE: 15

Glu Leu Phe Gln Tyr Met Glu Lys Tyr Asp Tyr Glu Gln Val Leu Phe
1               5                   10                  15

Cys Gln Asp Lys Glu Ser Gly Leu Lys Ala Ile Ile Val Ile His Asp
```

```
              20                  25                  30
Thr Thr Leu Gly Pro Ala Leu Gly Gly Thr Arg Met Trp Met Tyr Asn
            35                  40                  45
Ser Glu Glu Ala Leu Glu Asp Ala Leu Arg Leu Ala Arg Gly Ser
 50                  55                  60
Thr Tyr Met Asn Ala Ala Ala Gly Leu Asn Leu Gly Gly Lys Thr
 65                  70                  75                  80
Val Ile Ile Gly Asp Pro Arg Lys Asp Lys Asn Glu Ala Met Phe Arg
                85                  90                  95
Ala Phe Gly Arg Phe Ile Gln Gly Leu Asn Gly Arg Tyr Ile Thr Ala
               100                 105                 110
Val Asp Val Gly Thr Thr Val Ala Asp Met Asp Ile Ile Tyr Gln Glu
               115                 120                 125
Thr Asp Tyr Val Thr Gly Ile Ser Pro Glu Phe
               130                 135
```

<210> SEQ ID NO 16
<211> LENGTH: 227
<212> TYPE: PRT
<213> ORGANISM: Artificial Sequence
<220> FEATURE:
<223> OTHER INFORMATION: synthesized polypeptide

<400> SEQUENCE: 16

```
Gly Ser Ser Gly Asn Pro Ser Pro Ala Thr Ala Tyr Gly Val Tyr Arg
 1               5                  10                  15
Gly Met Lys Ala Ala Lys Glu Ala Phe Gly Ser Asp Ser Leu Glu
                20                  25                  30
Gly Lys Val Val Ala Val Gln Gly Val Gly Asn Val Ala Tyr His Leu
                35                  40                  45
Cys Arg His Leu His Glu Glu Gly Ala Lys Leu Ile Val Thr Asp Ile
      50                  55                  60
Asn Lys Glu Ala Val Ala Arg Ala Val Glu Glu Phe Gly Ala Lys Ala
 65                  70                  75                  80
Val Asp Pro Asn Asp Ile Tyr Gly Val Glu Cys Asp Ile Phe Ala Pro
                85                  90                  95
Cys Ala Leu Gly Gly Ile Ile Asn Asp Gln Thr Ile Pro Gln Leu Lys
               100                 105                 110
Ala Lys Val Ile Ala Gly Ser Ala Asp Leu Gln Leu Lys Glu Pro Arg
               115                 120                 125
His Gly Asp Met Ile His Glu Met Gly Ile Val Tyr Ala Pro Asp Tyr
               130                 135                 140
Val Ile Asn Ala Gly Gly Cys Ile Asn Val Ala Asp Glu Leu Tyr Gly
145                 150                 155                 160
Tyr Asn Arg Glu Arg Ala Met Lys Lys Ile Glu Gln Ile Tyr Asp Asn
                    165                 170                 175
Ile Glu Lys Val Phe Ala Ile Ala Lys Arg Asp Asn Ile Pro Thr Tyr
                180                 185                 190
Val Ala Ala Asp Arg Met Ala Glu Glu Arg Ile Glu Thr Met Arg Lys
                195                 200                 205
Ala Arg Ser Gln Phe Leu Gln Asn Gly His His Ile Leu Ser Arg Arg
                    210                 215                 220
Arg Ala Arg
225
```

```
<210> SEQ ID NO 17
<211> LENGTH: 227
<212> TYPE: PRT
<213> ORGANISM: Artificial Sequence
<220> FEATURE:
<223> OTHER INFORMATION: synthesized polypeptide

<400> SEQUENCE: 17
```

Gly Ser Ser Gly Asn Pro Ser Pro Ala Thr Ala Tyr Gly Val Tyr Arg
1               5                   10                  15

Gly Met Lys Ala Ala Lys Glu Ala Phe Gly Ser Asp Ser Leu Glu
            20                  25                  30

Gly Lys Val Val Ala Val Gln Gly Val Gly Asn Val Ala Tyr His Leu
            35                  40                  45

Cys Arg His Leu His Glu Glu Gly Ala Lys Leu Ile Val Thr Asp Ile
50                  55                  60

Asn Lys Glu Ala Val Ala Arg Ala Val Glu Glu Phe Gly Ala Lys Ala
65                  70                  75                  80

Val Asp Pro Asn Asp Ile Tyr Gly Val Glu Cys Asp Ile Phe Ala Pro
                85                  90                  95

Cys Ala Leu Gly Gly Ile Ile Asn Asp Gln Thr Ile Pro Gln Leu Lys
            100                 105                 110

Ala Lys Val Ile Ala Gly Ser Ala Leu Asn Gln Leu Lys Glu Pro Arg
            115                 120                 125

His Gly Asp Met Ile His Glu Met Gly Ile Val Tyr Ala Pro Asp Tyr
            130                 135                 140

Val Ile Asn Ala Gly Gly Cys Ile Asn Val Ala Asp Glu Leu Tyr Gly
145                 150                 155                 160

Tyr Asn Arg Glu Arg Ala Met Lys Lys Ile Glu Gln Ile Tyr Asp Asn
                165                 170                 175

Ile Glu Lys Val Phe Ala Ile Ala Lys Arg Asp Asn Ile Pro Thr Tyr
            180                 185                 190

Val Ala Ala Asp Arg Met Ala Glu Glu Arg Ile Glu Thr Met Arg Lys
            195                 200                 205

Ala Arg Ser Gln Phe Leu Gln Asn Gly His His Ile Leu Ser Arg Arg
            210                 215                 220

Arg Ala Arg
225

```
<210> SEQ ID NO 18
<211> LENGTH: 147
<212> TYPE: PRT
<213> ORGANISM: Artificial Sequence
<220> FEATURE:
<223> OTHER INFORMATION: synthesized polypeptide

<400> SEQUENCE: 18
```

Thr Glu Ala Asp Asn Gly Val Leu His Thr Leu Phe His Ser Asp Gln
1               5                   10                  15

Gly Gly His Glu Gln Val Val Leu Cys Gln Asp Arg Ala Ser Gly Leu
            20                  25                  30

Lys Ala Val Ile Ala Ile His Ser Thr Ala Leu Gly Pro Ala Leu Gly
            35                  40                  45

Gly Thr Arg Phe Tyr Pro Tyr Ala Thr Glu Glu Glu Ala Val Ala Asp
            50                  55                  60

Val Leu Asn Leu Ser Arg Gly Met Ser Tyr Ser Asn Ala Met Ala Gly
65                  70                  75                  80

Leu Asp His Gly Gly Gly Lys Ala Val Ile Ile Gly Asp Pro Glu Gln
                85                  90                  95

Ile Lys Ser Glu Asp Leu Leu Leu Ala Phe Gly Arg Phe Val Ala Ser
            100                 105                 110

Leu Gly Gly Arg Tyr Val Thr Ala Cys Asp Val Gly Thr Tyr Val Ala
        115                 120                 125

Asp Met Asp Val Val Ala Arg Glu Cys Arg Trp Thr Thr Gly Arg Ser
    130                 135                 140

Pro Glu Asn
145

<210> SEQ ID NO 19
<211> LENGTH: 210
<212> TYPE: PRT
<213> ORGANISM: Artificial Sequence
<220> FEATURE:
<223> OTHER INFORMATION: synthesized polypeptide

<400> SEQUENCE: 19

Gly Gly Ala Gly Asp Ser Ser Val Leu Thr Ala Phe Gly Val Phe Gln
1               5                   10                  15

Gly Met Arg Ala Ser Ala Glu His Leu Trp Gly Asp Pro Ser Leu Arg
            20                  25                  30

Gly Arg Lys Val Gly Val Ala Gly Val Gly Lys Val Gly His His Leu
        35                  40                  45

Val Glu His Leu Leu Glu Asp Gly Ala Asp Val Val Ile Thr Asp Val
    50                  55                  60

Arg Glu Glu Ser Val Asn Arg Ser Thr His Lys His Pro Ser Val Thr
65                  70                  75                  80

Ala Val Ala Asp Thr Glu Ala Leu Ile Arg Thr Glu Gly Leu Asp Ile
                85                  90                  95

Tyr Ala Pro Cys Ala Leu Gly Gly Ala Leu Asp Asp Ser Val Pro
            100                 105                 110

Val Leu Thr Ala Lys Val Val Cys Gly Ala Ala Asn Leu Gln Leu Ala
        115                 120                 125

His Pro Gly Val Glu Lys Asp Leu Ala Asp Arg Ser Ile Leu Tyr Ala
    130                 135                 140

Pro Asp Tyr Val Val Asn Ala Gly Gly Val Ile Gln Val Ala Asp Glu
145                 150                 155                 160

Leu Arg Gly Phe Asp Phe Asp Arg Cys Lys Ala Lys Ala Ser Lys Ile
                165                 170                 175

Phe Asp Thr Thr Leu Ala Ile Phe Ala Arg Ala Lys Glu Asp Gly Ile
            180                 185                 190

Pro Pro Ala Ala Ala Asp Arg Ile Ala Glu Gln Arg Met Ser Asp
        195                 200                 205

Ala Arg
    210

<210> SEQ ID NO 20
<211> LENGTH: 376
<212> TYPE: PRT
<213> ORGANISM: Artificial Sequence
<220> FEATURE:
<223> OTHER INFORMATION: synthesized polypeptide

<400> SEQUENCE: 20

Ser Leu Val Glu Lys Thr Ser Ile Ile Lys Asp Phe Thr Leu Phe Glu
1               5                   10                  15

Lys Met Ser Glu His Glu Gln Val Val Phe Cys Asn Asp Pro Ala Thr
     20                  25                  30

Gly Leu Arg Ala Ile Ile Ala Ile His Asp Thr Thr Leu Gly Pro Ala
         35                  40                  45

Leu Gly Gly Cys Arg Met Gln Pro Tyr Asn Ser Val Glu Glu Ala Leu
 50                  55                  60

Glu Asp Ala Leu Arg Leu Ser Lys Gly Met Thr Tyr Ser Cys Ala Ala
 65                  70                  75                  80

Ser Asp Val Asp Phe Gly Gly Lys Ala Val Ile Ile Gly Asp Pro
                 85                  90                  95

Gln Lys Asp Lys Ser Pro Glu Leu Phe Arg Ala Phe Gln Phe Val
         100                 105                 110

Asp Ser Leu Gly Gly Arg Phe Tyr Thr Gly Thr Asp Met Gly Thr Asn
         115                 120                 125

Met Glu Asp Phe Ile His Ala Met Lys Glu Thr Asn Cys Ile Val Gly
130                 135                 140

Val Pro Glu Ala Tyr Gly Ser Ser Gly Asn Pro Ser Pro Ala Thr Ala
145                 150                 155                 160

Tyr Gly Val Tyr Arg Gly Met Lys Ala Ala Ala Lys Glu Ala Phe Gly
                165                 170                 175

Ser Asp Ser Leu Glu Gly Lys Val Val Ala Val Gln Gly Val Gly Asn
             180                 185                 190

Val Ala Tyr His Leu Cys Arg His Leu His Glu Glu Gly Ala Lys Leu
         195                 200                 205

Ile Val Thr Asp Ile Asn Lys Glu Ala Val Ala Arg Ala Val Glu Glu
         210                 215                 220

Phe Gly Ala Lys Ala Val Asp Pro Asn Asp Ile Tyr Gly Val Glu Cys
225                 230                 235                 240

Asp Ile Phe Ala Pro Cys Ala Leu Gly Gly Ile Ile Asn Asp Gln Thr
                245                 250                 255

Ile Pro Gln Leu Lys Ala Lys Val Ile Ala Gly Ser Ala Leu Asn Gln
             260                 265                 270

Leu Lys Glu Pro Arg His Gly Asp Met Ile His Glu Met Gly Ile Val
         275                 280                 285

Tyr Ala Pro Asp Tyr Val Ile Asn Ala Gly Gly Cys Ile Asn Val Ala
290                 295                 300

Asp Glu Leu Tyr Gly Tyr Asn Arg Glu Arg Ala Met Lys Lys Ile Glu
305                 310                 315                 320

Gln Ile Tyr Asp Asn Ile Glu Lys Val Phe Ala Ile Ala Lys Arg Asp
                325                 330                 335

Asn Ile Pro Thr Tyr Val Ala Ala Asp Arg Met Ala Glu Glu Arg Ile
             340                 345                 350

Glu Thr Met Arg Lys Ala Arg Ser Gln Phe Leu Gln Asn Gly His His
         355                 360                 365

Ile Leu Ser Arg Arg Arg Ala Arg
         370                 375

<210> SEQ ID NO 21
<211> LENGTH: 376
<212> TYPE: PRT
<213> ORGANISM: Artificial Sequence
<220> FEATURE:
<223> OTHER INFORMATION: synthesized polypeptide

<400> SEQUENCE: 21

Ser Leu Val Glu Lys Thr Ser Ile Ile Lys Asp Phe Thr Leu Phe Glu
1               5                   10                  15

Lys Met Ser Glu His Glu Gln Val Val Phe Cys Asn Asp Pro Ala Thr
            20                  25                  30

Gly Leu Arg Ala Ile Ala Ile His Asp Thr Thr Leu Gly Pro Ala
        35                  40                  45

Leu Gly Gly Cys Arg Met Gln Pro Tyr Asn Ser Val Glu Glu Ala Leu
    50                  55                  60

Glu Asp Ala Leu Arg Leu Ser Lys Gly Met Thr Tyr Ser Cys Ala Ala
65                  70                  75                  80

Ser Asp Val Asp Phe Gly Gly Lys Ala Val Ile Ile Gly Asp Pro
                85                  90                  95

Gln Lys Asp Lys Ser Pro Glu Leu Phe Arg Ala Phe Gly Gln Phe Val
            100                 105                 110

Asp Ser Leu Gly Gly Arg Phe Tyr Thr Gly Thr Asp Met Gly Thr Asn
            115                 120                 125

Met Glu Asp Phe Ile His Ala Met Lys Glu Thr Asn Cys Ile Val Gly
    130                 135                 140

Val Pro Glu Ala Tyr Gly Ser Ser Gly Asn Pro Ser Pro Ala Thr Ala
145                 150                 155                 160

Tyr Gly Val Tyr Arg Gly Met Lys Ala Ala Lys Glu Ala Phe Gly
                165                 170                 175

Ser Asp Ser Leu Glu Gly Lys Val Val Ala Val Gln Gly Val Gly Asn
            180                 185                 190

Val Ala Tyr His Leu Cys Arg His Leu His Glu Gly Ala Lys Leu
                195                 200                 205

Ile Val Thr Asp Ile Asn Lys Glu Ala Val Ala Arg Ala Val Glu Glu
            210                 215                 220

Phe Gly Ala Lys Ala Val Asp Pro Asn Asp Ile Tyr Gly Val Glu Cys
225                 230                 235                 240

Asp Ile Phe Ala Pro Cys Ala Leu Gly Gly Ile Ile Asn Asp Gln Thr
                245                 250                 255

Ile Pro Gln Leu Lys Ala Lys Val Ile Ala Gly Ser Ala Asp Leu Gln
            260                 265                 270

Leu Lys Glu Pro Arg His Gly Asp Met Ile His Glu Met Gly Ile Val
    275                 280                 285

Tyr Ala Pro Asp Tyr Val Ile Asn Ala Gly Gly Cys Ile Asn Val Ala
    290                 295                 300

Asp Glu Leu Tyr Gly Tyr Asn Arg Glu Arg Ala Met Lys Lys Ile Glu
305                 310                 315                 320

Gln Ile Tyr Asp Asn Ile Glu Lys Val Phe Ala Ile Ala Lys Arg Asp
                325                 330                 335

Asn Ile Pro Thr Tyr Val Ala Ala Asp Arg Met Ala Glu Glu Arg Ile
            340                 345                 350

Glu Thr Met Arg Lys Ala Arg Ser Gln Phe Leu Gln Asn Gly His His
    355                 360                 365

Ile Leu Ser Arg Arg Arg Ala Arg
    370                 375

<210> SEQ ID NO 22
<211> LENGTH: 376
<212> TYPE: PRT
<213> ORGANISM: Artificial Sequence
<220> FEATURE:

<223> OTHER INFORMATION: synthesized polypeptide

<400> SEQUENCE: 22

Ser Leu Val Glu Lys Thr Ser Ile Ile Lys Asp Phe Thr Leu Phe Glu
1               5                   10                  15

Lys Met Ser Glu His Glu Gln Val Val Phe Cys Asn Asp Pro Ala Thr
            20                  25                  30

Gly Leu Arg Ala Ile Ile Ala Ile His Asp Thr Thr Leu Gly Pro Ala
        35                  40                  45

Leu Gly Gly Cys Arg Met Gln Pro Tyr Asn Ser Val Glu Glu Ala Leu
50              55                  60

Glu Asp Ala Leu Arg Leu Ser Lys Gly Met Thr Tyr Ser Cys Ala Ala
65                  70                  75                  80

Ser Asp Val Asp Phe Gly Gly Gly Lys Ala Val Ile Ile Gly Asp Pro
                85                  90                  95

Gln Lys Asp Lys Ser Pro Glu Leu Phe Arg Ala Phe Gly Gln Phe Val
            100                 105                 110

Asp Ser Leu Gly Gly Arg Phe Tyr Thr Gly Thr Asp Met Gly Thr Asn
        115                 120                 125

Met Glu Asp Phe Ile His Ala Met Lys Glu Thr Asn Cys Ile Val Gly
130                 135                 140

Val Pro Glu Ala Tyr Gly Ser Ser Gly Asn Pro Ser Pro Ala Thr Ala
145                 150                 155                 160

Tyr Gly Val Tyr Arg Gly Met Lys Ala Ala Lys Glu Ala Phe Gly
                165                 170                 175

Ser Asp Ser Leu Glu Gly Lys Val Ala Val Gln Gly Val Gly Asn
            180                 185                 190

Val Ala Tyr His Leu Cys Arg His Leu His Glu Glu Gly Ala Lys Leu
                195                 200                 205

Ile Val Thr Asp Ile Asn Lys Glu Ala Val Ala Arg Ala Val Glu Glu
            210                 215                 220

Phe Gly Ala Lys Ala Val Asp Pro Asn Asp Ile Tyr Gly Val Glu Cys
225                 230                 235                 240

Asp Ile Phe Ala Pro Cys Ala Leu Gly Gly Ile Ile Asn Asp Gln Thr
                245                 250                 255

Ile Pro Gln Leu Lys Ala Lys Val Ile Ala Gly Ser Ala Leu Leu Gln
            260                 265                 270

Leu Lys Glu Pro Arg His Gly Asp Met Ile His Glu Met Gly Ile Val
        275                 280                 285

Tyr Ala Pro Asp Tyr Val Ile Asn Ala Gly Gly Cys Ile Asn Val Ala
290                 295                 300

Asp Glu Leu Tyr Gly Tyr Asn Arg Glu Arg Ala Met Lys Lys Ile Glu
305                 310                 315                 320

Gln Ile Tyr Asp Asn Ile Glu Lys Val Phe Ala Ile Ala Lys Arg Asp
            325                 330                 335

Asn Ile Pro Thr Tyr Val Ala Ala Asp Arg Met Ala Glu Glu Arg Ile
        340                 345                 350

Glu Thr Met Arg Lys Ala Arg Ser Gln Phe Leu Gln Asn Gly His His
    355                 360                 365

Ile Leu Ser Arg Arg Arg Ala Arg
        370                 375

<210> SEQ ID NO 23
<211> LENGTH: 359

<212> TYPE: PRT
<213> ORGANISM: Artificial Sequence
<220> FEATURE:
<223> OTHER INFORMATION: Synthesized polypeptide

<400> SEQUENCE: 23

```
Ser Leu Val Glu Lys Thr Ser Ile Ile Lys Asp Phe Thr Leu Phe Glu
1               5                   10                  15
Lys Met Ser Glu His Glu Gln Val Val Phe Cys Asn Asp Pro Ala Thr
            20                  25                  30
Gly Leu Arg Ala Ile Ile Ala Ile His Asp Thr Thr Leu Gly Pro Ala
        35                  40                  45
Leu Gly Gly Cys Arg Met Gln Pro Tyr Asn Ser Val Glu Glu Ala Leu
    50                  55                  60
Glu Asp Ala Leu Arg Leu Ser Lys Gly Met Thr Tyr Ser Cys Ala Ala
65                  70                  75                  80
Ser Asp Val Asp Phe Gly Gly Lys Ala Val Ile Ile Gly Asp Pro
                85                  90                  95
Gln Lys Asp Lys Ser Pro Glu Leu Phe Arg Ala Phe Gly Gln Phe Val
            100                 105                 110
Asp Ser Leu Gly Gly Arg Phe Tyr Thr Gly Thr Asp Met Gly Thr Asn
        115                 120                 125
Met Glu Asp Phe Ile His Ala Met Lys Glu Thr Asn Cys Ile Val Gly
130                 135                 140
Val Pro Glu Ala Tyr Gly Gly Ala Gly Asp Ser Ser Val Leu Thr Ala
145                 150                 155                 160
Phe Gly Val Phe Gln Gly Met Arg Ala Ser Ala Glu His Leu Trp Gly
                165                 170                 175
Asp Pro Ser Leu Arg Gly Arg Lys Val Gly Val Ala Gly Val Gly Lys
            180                 185                 190
Val Gly His His Leu Val Glu His Leu Leu Glu Asp Gly Ala Asp Val
        195                 200                 205
Val Ile Thr Asp Val Arg Glu Glu Ser Val Asn Arg Ser Thr His Lys
210                 215                 220
His Pro Ser Val Thr Ala Val Ala Asp Thr Glu Ala Leu Ile Arg Thr
225                 230                 235                 240
Glu Gly Leu Asp Ile Tyr Ala Pro Cys Ala Leu Gly Gly Ala Leu Asp
                245                 250                 255
Asp Asp Ser Val Pro Val Leu Thr Ala Lys Val Val Cys Gly Ala Ala
            260                 265                 270
Asn Leu Gln Leu Ala His Pro Gly Val Glu Lys Asp Leu Ala Asp Arg
        275                 280                 285
Ser Ile Leu Tyr Ala Pro Asp Tyr Val Val Asn Ala Gly Gly Val Ile
    290                 295                 300
Gln Val Ala Asp Glu Leu Arg Gly Phe Asp Phe Asp Arg Cys Lys Ala
305                 310                 315                 320
Lys Ala Ser Lys Ile Phe Asp Thr Thr Leu Ala Ile Phe Ala Arg Ala
                325                 330                 335
Lys Glu Asp Gly Ile Pro Pro Ala Ala Ala Asp Arg Ile Ala Glu
            340                 345                 350
Gln Arg Met Ser Asp Ala Arg
            355
```

<210> SEQ ID NO 24
<211> LENGTH: 360

```
<212> TYPE: PRT
<213> ORGANISM: Artificial Sequence
<220> FEATURE:
<223> OTHER INFORMATION: synthetic polypeptide

<400> SEQUENCE: 24

Met Ser Leu Val Glu Lys Thr Ser Ile Ile Lys Asp Phe Thr Leu Phe
1               5                   10                  15

Glu Lys Met Ser Glu His Glu Gln Val Val Phe Cys Asn Asp Pro Ala
            20                  25                  30

Thr Gly Leu Arg Ala Ile Ile Ala Ile His Asp Thr Thr Leu Gly Pro
        35                  40                  45

Ala Leu Gly Gly Cys Arg Met Gln Pro Tyr Asn Ser Val Glu Glu Ala
    50                  55                  60

Leu Glu Asp Ala Leu Arg Leu Ser Lys Gly Met Thr Tyr Ser Cys Ala
65                  70                  75                  80

Ala Ser Asp Val Asp Phe Gly Gly Lys Ala Val Ile Ile Gly Asp
                    85                  90                  95

Pro Gln Lys Asp Lys Ser Pro Glu Leu Phe Arg Ala Phe Gly Gln Phe
                100                 105                 110

Val Asp Ser Leu Gly Gly Arg Phe Tyr Thr Gly Thr Asp Met Gly Thr
                115                 120                 125

Asn Met Glu Asp Phe Ile His Ala Met Lys Glu Thr Asn Cys Ile Val
130                 135                 140

Gly Val Pro Glu Ala Tyr Gly Gly Ala Gly Asp Ser Ser Val Leu Thr
145                 150                 155                 160

Ala Phe Gly Val Phe Gln Gly Met Arg Ala Ser Ala Glu His Leu Trp
                165                 170                 175

Gly Asp Pro Ser Leu Arg Gly Arg Lys Val Gly Val Ala Gly Val Gly
                180                 185                 190

Lys Val Gly His His Leu Val Glu His Leu Leu Glu Asp Gly Ala Asp
            195                 200                 205

Val Val Ile Thr Asp Val Arg Glu Glu Ser Val Asn Arg Ser Thr His
210                 215                 220

Lys His Pro Ser Val Thr Ala Val Ala Asp Thr Glu Ala Leu Ile Arg
225                 230                 235                 240

Thr Glu Gly Leu Asp Ile Tyr Ala Pro Cys Ala Leu Gly Gly Ala Leu
                245                 250                 255

Asp Asp Asp Ser Val Pro Val Leu Thr Ala Lys Val Val Cys Gly Ala
                260                 265                 270

Ala Asn Leu Gln Leu Ala His Pro Gly Val Glu Lys Asp Leu Ala Asp
            275                 280                 285

Arg Ser Ile Leu Tyr Ala Pro Asp Tyr Val Val Asn Ala Gly Gly Val
        290                 295                 300

Ile Gln Val Ala Asp Glu Leu Arg Gly Phe Asp Phe Asp Arg Cys Lys
305                 310                 315                 320

Ala Lys Ala Ser Lys Ile Phe Asp Thr Thr Leu Ala Ile Phe Ala Arg
                325                 330                 335

Ala Lys Glu Asp Gly Ile Pro Pro Ala Ala Ala Asp Arg Ile Ala
            340                 345                 350

Glu Gln Arg Met Ser Asp Ala Arg
            355                 360

<210> SEQ ID NO 25
<211> LENGTH: 8
```

```
<212> TYPE: PRT
<213> ORGANISM: Artificial Sequence
<220> FEATURE:
<223> OTHER INFORMATION: synthetic polypeptide

<400> SEQUENCE: 25

Asp Tyr Lys Asp Asp Asp Asp Lys
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 26

Tyr Pro Tyr Asp Val Pro
1               5

<210> SEQ ID NO 27
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 27

Ile Leu Lys Lys Ala Thr Ala Tyr Ile Leu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 28

Glu Gln Lys Leu Ile Ser Glu Glu Asp Leu
1               5                   10

<210> SEQ ID NO 29
<211> LENGTH: 60
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (27)..(27)
<223> OTHER INFORMATION: "B" can be C, G, or T
<220> FEATURE:
<221> NAME/KEY: misc_feature
<222> LOCATION: (29)..(30)
<223> OTHER INFORMATION: "N" can be A, C, G, or T
<220> FEATURE:
<221> NAME/KEY: misc_feature
<222> LOCATION: (32)..(32)
<223> OTHER INFORMATION: "R" can be A or G
<220> FEATURE:
<221> NAME/KEY: misc_feature
<222> LOCATION: (34)..(34)
<223> OTHER INFORMATION: "B" can be C, G, or T
<220> FEATURE:
<221> NAME/KEY: misc_feature
<222> LOCATION: (35)..(35)
<223> OTHER INFORMATION: "R" can be A or G
<220> FEATURE:
<221> NAME/KEY: misc_feature
<222> LOCATION: (37)..(37)
```

<223> OTHER INFORMATION: "K" can be G or T

<400> SEQUENCE: 29
agggctgaac ggccgctaca ttacggbgnn trabrtkggc acgaccgttg ccgatatgga    60

<210> SEQ ID NO 30
<211> LENGTH: 61
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (25)..(25)
<223> OTHER INFORMATION: "M" can be A or C
<220> FEATURE:
<221> NAME/KEY: misc_feature
<222> LOCATION: (27)..(27)
<223> OTHER INFORMATION: "Y" can be C or T
<220> FEATURE:
<221> NAME/KEY: misc_feature
<222> LOCATION: (28)..(28)
<223> OTHER INFORMATION: "V" can be A, C, or G
<220> FEATURE:
<221> NAME/KEY: misc_feature
<222> LOCATION: (30)..(30)
<223> OTHER INFORMATION: "Y" can be C or T
<220> FEATURE:
<221> NAME/KEY: misc_feature
<222> LOCATION: (32)..(33)
<223> OTHER INFORMATION: "N" can be A, C, G, or T
<220> FEATURE:
<221> NAME/KEY: misc_feature
<222> LOCATION: (35)..(35)
<223> OTHER INFORMATION: "V" can be A, C, or G

<400> SEQUENCE: 30
atccatatcg gcaacggtcg tgccmayvty anncvccgta atgtagcggc cgttcagccc    60
t                                                                   61

<210> SEQ ID NO 31
<211> LENGTH: 59
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (28)..(28)
<223> OTHER INFORMATION: "D" can be A, G, or T
<220> FEATURE:
<221> NAME/KEY: misc_feature
<222> LOCATION: (29)..(29)
<223> OTHER INFORMATION: "B" can be C, G, or T
<220> FEATURE:
<221> NAME/KEY: misc_feature
<222> LOCATION: (30)..(30)
<223> OTHER INFORMATION: "W" can be A or T
<220> FEATURE:
<221> NAME/KEY: misc_feature
<222> LOCATION: (32)..(32)
<223> OTHER INFORMATION: "B" can be C, G, or T
<220> FEATURE:
<221> NAME/KEY: misc_feature
<222> LOCATION: (34)..(34)
<223> OTHER INFORMATION: "D" can be A, G, or T
<220> FEATURE:
<221> NAME/KEY: misc_feature
<222> LOCATION: (35)..(35)
<223> OTHER INFORMATION: "B" can be C, G, or T
<220> FEATURE:
<221> NAME/KEY: misc_feature
<222> LOCATION: (36)..(36)
<223> OTHER INFORMATION: "W" can be A or T

<400> SEQUENCE: 31
attcatgaca cgacgctcgg cccggcgdbw gbcdbwacgc gcatgtggat gtacaattc    59

<210> SEQ ID NO 32
<211> LENGTH: 59
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (24)..(24)
<223> OTHER INFORMATION: "W" can be A or T
<220> FEATURE:
<221> NAME/KEY: misc_feature
<222> LOCATION: (25)..(25)
<223> OTHER INFORMATION: "V" can be A, C, or G
<220> FEATURE:
<221> NAME/KEY: misc_feature
<222> LOCATION: (26)..(26)
<223> OTHER INFORMATION: "H" can be A, C, or T
<220> FEATURE:
<221> NAME/KEY: misc_feature
<222> LOCATION: (28)..(28)
<223> OTHER INFORMATION: "V" can be A, C, or G
<220> FEATURE:
<221> NAME/KEY: misc_feature
<222> LOCATION: (30)..(30)
<223> OTHER INFORMATION: "W" can be A or T
<220> FEATURE:
<221> NAME/KEY: misc_feature
<222> LOCATION: (31)..(31)
<223> OTHER INFORMATION: "V" can be A, C, or G
<220> FEATURE:
<221> NAME/KEY: misc_feature
<222> LOCATION: (32)..(32)
<223> OTHER INFORMATION: "H" can be A, C, or T

<400> SEQUENCE: 32
gaattgtaca tccacatgcg cgtwvhgvcw vhcgccgggc cgagcgtcgt gtcatgaat    59

<210> SEQ ID NO 33
<211> LENGTH: 34
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (16)..(17)
<223> OTHER INFORMATION: "N" can be A, C, G, or T
<220> FEATURE:
<221> NAME/KEY: misc_feature
<222> LOCATION: (18)..(18)
<223> OTHER INFORMATION: "K" can be G or T

<400> SEQUENCE: 33
gattatgtga tcaacnnkgg cggcgtcatc aacg    34

<210> SEQ ID NO 34
<211> LENGTH: 34
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (17)..(17)
<223> OTHER INFORMATION: "M" can be A or C
<220> FEATURE:
<221> NAME/KEY: misc_feature
<222> LOCATION: (18)..(19)

<223> OTHER INFORMATION: "N" can be A, C, G, or T

<400> SEQUENCE: 34
cgttgatgac gccgccmnng ttgatcacat aatc         34

<210> SEQ ID NO 35
<211> LENGTH: 43
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (14)..(14)
<223> OTHER INFORMATION: "D" can be A, G, or T
<220> FEATURE:
<221> NAME/KEY: misc_feature
<222> LOCATION: (15)..(15)
<223> OTHER INFORMATION: "B" can be C, G, or T
<220> FEATURE:
<221> NAME/KEY: misc_feature
<222> LOCATION: (16)..(16)
<223> OTHER INFORMATION: "S" can be C or G
<220> FEATURE:
<221> NAME/KEY: misc_feature
<222> LOCATION: (23)..(23)
<223> OTHER INFORMATION: "D" can be A, G, or T
<220> FEATURE:
<221> NAME/KEY: misc_feature
<222> LOCATION: (24)..(24)
<223> OTHER INFORMATION: "B" can be C, G, or T
<220> FEATURE:
<221> NAME/KEY: misc_feature
<222> LOCATION: (25)..(25)
<223> OTHER INFORMATION: "S" can be C or G

<400> SEQUENCE: 35
caacgccggc ggcdbsatca acdbsgccga tgagctgtac ggc         43

<210> SEQ ID NO 36
<211> LENGTH: 43
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (19)..(19)
<223> OTHER INFORMATION: "S" can be C or G
<220> FEATURE:
<221> NAME/KEY: misc_feature
<222> LOCATION: (20)..(20)
<223> OTHER INFORMATION: "V" can be A, C, or G
<220> FEATURE:
<221> NAME/KEY: misc_feature
<222> LOCATION: (28)..(28)
<223> OTHER INFORMATION: "S" can be C or G
<220> FEATURE:
<221> NAME/KEY: misc_feature
<222> LOCATION: (29)..(29)
<223> OTHER INFORMATION: "V" can be A, C, or G
<220> FEATURE:
<221> NAME/KEY: misc_feature
<222> LOCATION: (30)..(30)
<223> OTHER INFORMATION: "H" can be A, C, or T

<400> SEQUENCE: 36
gccgtacagc tcatcggcsv hgttgatsvh gccgccggcg ttg         43

<210> SEQ ID NO 37
<211> LENGTH: 43
<212> TYPE: DNA
<213> ORGANISM: Artificial Sequence

```
<220> FEATURE:
<223> OTHER INFORMATION: synthetic degenerate primer for mutagenesis
<220> FEATURE:
<221> NAME/KEY: misc_feature
<222> LOCATION: (22)..(23)
<223> OTHER INFORMATION: "N" can be A, C, G, or T
<220> FEATURE:
<221> NAME/KEY: misc_feature
<222> LOCATION: (24)..(24)
<223> OTHER INFORMATION: "K" can be G or T

<400> SEQUENCE: 37
ctgaacggcc gctacattac gnnkgttgac gttggcacga ccg          43

<210> SEQ ID NO 38
<211> LENGTH: 43
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (20)..(20)
<223> OTHER INFORMATION: "M" can be A or C
<220> FEATURE:
<221> NAME/KEY: misc_feature
<222> LOCATION: (21)..(22)
<223> OTHER INFORMATION: "N" can be A, C, G, or T

<400> SEQUENCE: 38
cggtcgtgcc aacgtcaacm nncgtaatgt agcggccgtt cag          43

<210> SEQ ID NO 39
<211> LENGTH: 36
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (14)..(15)
<223> OTHER INFORMATION: "N" can be A, C, G, or T
<220> FEATURE:
<221> NAME/KEY: misc_feature
<222> LOCATION: (16)..(16)
<223> OTHER INFORMATION: "K" can be G or T

<400> SEQUENCE: 39
cgccggcggc gtcnnkaacg tcgccgatga gctgta          36

<210> SEQ ID NO 40
<211> LENGTH: 36
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (21)..(21)
<223> OTHER INFORMATION: "M" can be A or C
<220> FEATURE:
<221> NAME/KEY: misc_feature
<222> LOCATION: (22)..(23)
<223> OTHER INFORMATION: "N" can be A, C, G, or T

<400> SEQUENCE: 40
tacagctcat cggcgacgtt mnngacgccg ccggcg          36

<210> SEQ ID NO 41
<211> LENGTH: 45
<212> TYPE: DNA
```

<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (20)..(21)
<223> OTHER INFORMATION: "N" can be A, C, G, or T
<220> FEATURE:
<221> NAME/KEY: misc_feature
<222> LOCATION: (22)..(22)
<223> OTHER INFORMATION: "K" can be G or T

<400> SEQUENCE: 41
cgtcatcaac gtcgccgatn nkctgtacgg ctacaaccgt gaacg        45

<210> SEQ ID NO 42
<211> LENGTH: 45
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (24)..(24)
<223> OTHER INFORMATION: "M" can be A or C
<220> FEATURE:
<221> NAME/KEY: misc_feature
<222> LOCATION: (25)..(26)
<223> OTHER INFORMATION: "N" can be A, C, G, or T

<400> SEQUENCE: 42
cgttcacggt tgtagccgta cagmnnatcg gcgacgttga tgacg        45

<210> SEQ ID NO 43
<211> LENGTH: 36
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (14)..(15)
<223> OTHER INFORMATION: "N" can be A, C, G, or T
<220> FEATURE:
<221> NAME/KEY: misc_feature
<222> LOCATION: (16)..(16)
<223> OTHER INFORMATION: "K" can be G or T

<400> SEQUENCE: 43
cgccggctcg gcgnnkaatc agctgaaaga gccgcg        36

<210> SEQ ID NO 44
<211> LENGTH: 36
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (21)..(21)
<223> OTHER INFORMATION: "M" can be A or C
<220> FEATURE:
<221> NAME/KEY: misc_feature
<222> LOCATION: (22)..(23)
<223> OTHER INFORMATION: "N" can be A, C, G, or T

<400> SEQUENCE: 44
cgcggctctt tcagctgatt mnncgccgag ccggcg        36

<210> SEQ ID NO 45
<211> LENGTH: 33

```
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (18)..(19)
<223> OTHER INFORMATION: "D" can be A, G, or T
<220> FEATURE:
<221> NAME/KEY: misc_feature
<222> LOCATION: (20)..(20)
<223> OTHER INFORMATION: "K" can be G or T

<400> SEQUENCE: 45
cccgcggcat gacgtacddk aacgcggccg ccg                                    33

<210> SEQ ID NO 46
<211> LENGTH: 33
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (14)..(14)
<223> OTHER INFORMATION: "M" can be A or C
<220> FEATURE:
<221> NAME/KEY: misc_feature
<222> LOCATION: (15)..(16)
<223> OTHER INFORMATION: "H" can be A, C, or T

<400> SEQUENCE: 46
cggcggccgc gttmhhgtac gtcatgccgc ggg                                    33

<210> SEQ ID NO 47
<211> LENGTH: 36
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (14)..(15)
<223> OTHER INFORMATION: "D" can be A, G, or T
<220> FEATURE:
<221> NAME/KEY: misc_feature
<222> LOCATION: (16)..(16)
<223> OTHER INFORMATION: "K" can be G or T

<400> SEQUENCE: 47
cgccggctcg gcgddkaatc agctgaaaga gccgcg                                 36

<210> SEQ ID NO 48
<211> LENGTH: 36
<212> TYPE: DNA
<213> ORGANISM: Artificial Sequence
<220> FEATURE:
<223> OTHER INFORMATION: synthetic degenerate primer for mutagenesis
<220> FEATURE:
<221> NAME/KEY: misc_feature
<222> LOCATION: (21)..(21)
<223> OTHER INFORMATION: "M" can be A or C
<220> FEATURE:
<221> NAME/KEY: misc_feature
<222> LOCATION: (22)..(23)
<223> OTHER INFORMATION: "H" can be A, C, or T

<400> SEQUENCE: 48
cgcggctctt tcagctgatt mhhcgccgag ccggcg                                 36

<210> SEQ ID NO 49
```

```
<211> LENGTH: 38
<212> TYPE: DNA
<213> ORGANISM: Artificial Sequence
<220> FEATURE:
<223> OTHER INFORMATION: synthetic primer

<400> SEQUENCE: 49
ggaattccat atgagcttag tagaaaaaac atccatca                          38

<210> SEQ ID NO 50
<211> LENGTH: 34
<212> TYPE: DNA
<213> ORGANISM: Artificial Sequence
<220> FEATURE:
<223> OTHER INFORMATION: synthetic primer

<400> SEQUENCE: 50
ccgctcgagt attagttgcg aatatcccat tttg                              34

<210> SEQ ID NO 51
<211> LENGTH: 39
<212> TYPE: DNA
<213> ORGANISM: Artificial Sequence
<220> FEATURE:
<223> OTHER INFORMATION: synthetic primer

<400> SEQUENCE: 51
gcctttccaa aggaatgact tacatgtgcg cggcgtccg                         39

<210> SEQ ID NO 52
<211> LENGTH: 39
<212> TYPE: DNA
<213> ORGANISM: Artificial Sequence
<220> FEATURE:
<223> OTHER INFORMATION: synthetic primer

<400> SEQUENCE: 52
cggacgccgc gcacatgtaa gtcattcctt tggaaaggc                         39

<210> SEQ ID NO 53
<211> LENGTH: 51
<212> TYPE: DNA
<213> ORGANISM: Artificial Sequence
<220> FEATURE:
<223> OTHER INFORMATION: synthetic primer

<400> SEQUENCE: 53
ggcggccgtt tctatacagg tgtggatatg ggaacgaata tggaagattt c           51

<210> SEQ ID NO 54
<211> LENGTH: 51
<212> TYPE: DNA
<213> ORGANISM: Artificial Sequence
<220> FEATURE:
<223> OTHER INFORMATION: synthetic primer

<400> SEQUENCE: 54
gaaatcttcc atattcgttc ccatatccac acctgtatag aaacggccgc c           51

<210> SEQ ID NO 55
<211> LENGTH: 45
<212> TYPE: DNA
<213> ORGANISM: Artificial Sequence
<220> FEATURE:
<223> OTHER INFORMATION: synthetic primer

<400> SEQUENCE: 55
```

```
gcaatcgccg gttcagccgt gaatcagctg cttacggagg atcac          45

<210> SEQ ID NO 56
<211> LENGTH: 45
<212> TYPE: DNA
<213> ORGANISM: artificial sequence
<220> FEATURE:
<223> OTHER INFORMATION: Mutational primer applied to B. badius PheDH

<400> SEQUENCE: 56
gtgatcctcc gtaagcagct gattcacggc tgaaccggcg attgc          45

<210> SEQ ID NO 57
<211> LENGTH: 35
<212> TYPE: DNA
<213> ORGANISM: Artificial Sequence
<220> FEATURE:
<223> OTHER INFORMATION: synthetic primer

<400> SEQUENCE: 57
gggaattcca tatgagtatc gacagcgcac tgaac                     35

<210> SEQ ID NO 58
<211> LENGTH: 21
<212> TYPE: DNA
<213> ORGANISM: Artificial Sequence
<220> FEATURE:
<223> OTHER INFORMATION: synthetic primer

<400> SEQUENCE: 58
ccatgattac gccaagcttg c                                    21

<210> SEQ ID NO 59
<211> LENGTH: 39
<212> TYPE: DNA
<213> ORGANISM: Artificial Sequence
<220> FEATURE:
<223> OTHER INFORMATION: synthetic primer

<400> SEQUENCE: 59
cgacaacgac agcgactgcc tagggcccgt cgactgcag                 39

<210> SEQ ID NO 60
<211> LENGTH: 39
<212> TYPE: DNA
<213> ORGANISM: Artificial Sequence
<220> FEATURE:
<223> OTHER INFORMATION: synthetic primer

<400> SEQUENCE: 60
ctgcagtcga cgggccctag gcagtcgctg tcgttgtcg                 39

<210> SEQ ID NO 61
<211> LENGTH: 39
<212> TYPE: DNA
<213> ORGANISM: Artificial Sequence
<220> FEATURE:
<223> OTHER INFORMATION: synthetic primer

<400> SEQUENCE: 61
gggggcgatg acgttgatga tggcagtgag caaccttcc                 39

<210> SEQ ID NO 62
<211> LENGTH: 39
<212> TYPE: DNA
```

<213> ORGANISM: Artificial Sequence
<220> FEATURE:
<223> OTHER INFORMATION: synthetic primer

<400> SEQUENCE: 62

```
ggaaggttgc tcactgccat catcaacgtc atcgccccc                              39
```

<210> SEQ ID NO 63
<211> LENGTH: 1134
<212> TYPE: DNA
<213> ORGANISM: Artificial Sequence
<220> FEATURE:
<223> OTHER INFORMATION: synthetic polynucleotide

<400> SEQUENCE: 63

```
atgagcttag tagaaaaaac atccatcata aaagatttca ctcttttga aaaaatgtct        60
gaacatgaac aagttgtttt tgcaacgat ccggcgacag gactaagggc cattatcgct       120
attcatgaca ccacactcgg acctgcgctc ggcggctgcc gcatgcagcc ttataacagt      180
gtggaagaag cattggaaga tgctcttcgc ctttccaaag gaatgactta cagttgcgcg     240
gcgtccgatg tcgactttgg cggcggaaaa gcagtcatta tcggtgatcc gcagaaagat    300
aaatctccag aactgttccg cgcgtttggc caatttgttg attcgcttgg cggccgtttc    360
tatacaggta ctgatatggg aacgaatatg aagatttca ttcacgccat gaaagaaaca     420
aactgcattg ttggggtgcc ggaagcgtat ggctcttctg caacccgtc gccggccacg     480
gcttacggcg tatatcgtgg gatgaaagcg gcggcgaagg aagcatttgg cagtgattcg     540
cttgaaggaa aagttgtcgc cgtccaagga gtcggcaatg tcgcctacca tttatgccgc     600
catttgcacg aagaaggagc gaaactcatc gttaccgaca tcaacaagga agcggtggcg    660
cgcgcggtcg aggaatttgg ggcgaaagca gtcgacccga acgacattta cggcgtggag   720
tgcgacattt ttgctccatg cgcgctcggc ggcatcatca acgaccaaac gattccgcag    780
ctgaaagcga aagtgatcgc cggctcggcg ttgaatcagc tgaaagagcc gcgccatggc   840
gacatgatcc atgaaatggg catcgtctat gcaccagatt atgtgatcaa cgccggcggc    900
tgcatcaacg tcgccgatga gctgtacggc tacaaccgtg aacgggcgat gaaaaaaatc    960
gagcaaattt atgacaacat cgaaaaagtg tttgccatcg ccaagcgtga caacattcca   1020
acgtatgtgg ccgctgaccg gatggccgaa gaacgaattg aaacgatgcg caaagcgcgc  1080
agccaatttt tgcaaaacgg ccatcatatt ttaagccgcc gccgcgcccg ctaa          1134
```

<210> SEQ ID NO 64
<211> LENGTH: 1083
<212> TYPE: DNA
<213> ORGANISM: Artificial Sequence
<220> FEATURE:
<223> OTHER INFORMATION: synthetic polynucleotide

<400> SEQUENCE: 64

```
atgagcttag tagaaaaaac atccatcata aaagatttca ctcttttga aaaaatgtct        60
gaacatgaac aagttgtttt tgcaacgat ccggcgacag gactaagggc cattatcgct       120
attcatgaca ccacactcgg acctgcgctc ggcggctgcc gcatgcagcc ttataacagt      180
gtggaagaag cattggaaga tgctcttcgc ctttccaaag gaatgactta cagttgcgcg     240
gcgtccgatg tcgactttgg cggcggaaaa gcagtcatta tcggtgatcc gcagaaagat    300
aaatctccag aactgttccg cgcgtttggc caatttgttg attcgcttgg cggccgtttc    360
tatacaggta ctgatatggg aacgaatatg aagatttca ttcacgccat gaaagaaaca     420
```

```
aactgcattg ttggggtgcc ggaagcgtat ggtggtgcgg gtgatagcag cgtgctgacc      480
gcgtttggcg tgtttcaggg catgcgtgcg agcgcggaac atctgtgggg cgatccgagc      540
ctgcgtggcc gtaaagtggg tgtggcgggt gtgggcaaag tgggccatca tctggtggaa      600
catctgctgg aagatggtgc ggatgtggtg attaccgatg tgcgtgaaga aagcgtgaac      660
cgtagcaccc ataaacatcc gagcgtgacc gctgtggcgg ataccgaagc gctgattcgt      720
accgaaggcc tggatattta tgctccgtgc gcgctgggtg gtgcgctgga tgatgatagc      780
gtgccggtgc tgaccgctaa agtggtgtgc ggtgcggcaa acctgcagct ggcgcatccg      840
ggtgtggaaa aagatctggc ggatcgtagc attctgtatg ctccggatta tgtggtgaac      900
gcaggtggcg tgattcaggt ggcggatgaa ctgcgtggct ttgattttga tcgttgcaaa      960
gcgaaagcga gcaaaatttt tgataccacc ctggcgattt ttgcgcgtgc gaaagaagat     1020
ggcattcctc cggctgcggc tgcggatcgt attgcggaac agcgtatgag cgatgcgcgt     1080
taa                                                                   1083
```